United States Patent
Rao et al.

(10) Patent No.: US 9,909,188 B2
(45) Date of Patent: Mar. 6, 2018

(54) METHODS AND COMPOSITIONS INVOLVING LINCRNA AND LEUKEMIA

(71) Applicant: THE REGENTS OF THE UNIVERSITY OF CALIFORNIA, Oakland, CA (US)

(72) Inventors: Dinesh S. Rao, Culver City, CA (US); Ella Waters, Berkeley, CA (US); Norma I. Rodriguez-Malave, Los Angeles, CA (US); Thilini Fernando, Torrance, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/776,458

(22) PCT Filed: Mar. 14, 2014

(86) PCT No.: PCT/US2014/027313
§ 371 (c)(1),
(2) Date: Sep. 14, 2015

(87) PCT Pub. No.: WO2014/152411
PCT Pub. Date: Sep. 25, 2014

(65) Prior Publication Data
US 2016/0145692 A1 May 26, 2016

Related U.S. Application Data

(60) Provisional application No. 61/783,266, filed on Mar. 14, 2013.

(51) Int. Cl.
| | |
|---|---|
| *C12Q 1/68* | (2006.01) |
| *C12N 15/113* | (2010.01) |
| *A61K 31/573* | (2006.01) |
| *G01N 33/50* | (2006.01) |

(52) U.S. Cl.
CPC .......... *C12Q 1/6886* (2013.01); *A61K 31/573* (2013.01); *C12N 15/1135* (2013.01); *G01N 33/5005* (2013.01); *C12N 2310/11* (2013.01); *C12N 2310/113* (2013.01); *C12N 2310/14* (2013.01); *C12N 2310/531* (2013.01); *C12N 2330/51* (2013.01); *C12Q 2600/158* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

2012/0004278 A1  1/2012  Chang et al. .......... 514/44 A

OTHER PUBLICATIONS

Bassan et al., Crit. Rev. Onc/Hem, 50: 223-261, 2004.*
Chessells et al., Arch. Dis. Chil 85: 321-325, 2001.*
Affymetrix/Cold Spring Harbor Laboratory, Nature. 457:1028-1032, 2009.
Borowitz, M.J., and Chan, J.K.C. WHO Classification of Tumours of Haematopoietic and Lymphoid Tissues. 168-175, 2008.
Carrieri, C., et al., "Long non-coding antisense RNA controls Uchl1 translation through an embedded SINEB2 repeat." Nature. advance online publication, 2012.
Cesana, M., et al., Cell. 147:358-369, 2011.
Dinger, M.E., et al., Genome Research. 18:1433-1445, 2008.
Dordelmann et al., "Prednisone response is the strongest predictor of treatment outcome in infant acute lymphoblastic leukemia" Blood. 94:(4) 209-17. Aug. 1999.
Golub, T.R., et al., Science. 286:531-537, 1999.
Gong, C., et al., Nature. 470:284-288, 2011.
Guttman, M., et al., Nature. 458:223-227, 2009.
Guttman, M., et al., Nature. 477:295-300, 2011.
Hu, W., et al., Genes & Development. 25:2573-2578, 2011.
Huarte, M., et al., Cell. 142:409-419, 2010.
International Search Report and Written Opinion issued in PCT/US2014/027313, dated Jul. 10, 2014.
Khalil, A.M., et al., Proc Natl Acad Sci U S A. 106:11667-11672, 2009.
Lu, J., et al., Nature. 435:834-838, 2005.
NCBI, National Center for Biotechnology Information, GenBank [online], Bethesda, MD: National Library of Medicine, [retrieved on Jun. 18, 2014]. Submitted on Sep. 9, 2003.
Ng, S.-Y., et al., EMBO J. 31:522-533, 2012.
Niazi, F., and Valadkhan, S. RNA. 18:825-843, 2012.
Nordlund, J., et al., Leukemia. 26:1218-1227, 2012.
O'Connell, R.M., et al., PLoS ONE. 5:e12009, 2010.
Paralkar, V.R., and Weiss, M.J. Genes & Development. 25:2555-2558, 2011.
Prensner, J.R., et al., Nat Biotech. 29:742-749, 2011.
Rao, D.S., et al., Immunity. 33:48-59, 2010.
Rinn, J.L., et al., Cell. 129:1311-1323, 2007.
Sheik Mohamed, J., et al., RNA. 16:324-337, 2011.
Takagaki et al., "cDNA microarray analysis of altered gene expression in Ara-C-treated leukemia cells" Biochem Biophys Res Commun. 309 (2): 351-8. Sep. 2003.
Tibshirani, R., et al., Proc Natl Acad Sci U S A. 99:6567-6572, 2002.
Tibshirani, R., et al., Statistical Science. 18:104-117, 2003.
Tissing, W.J.E., et al., Blood. 109:3929-3935, 2007.
Tripathi, V., et al., Mol Cell. 39:925-938, 2010.
Ulitsky, I., et al., Cell. 147:1537-1550, 2011.
Vangipuram, S.D., et al., Tumour Biol. 33:2173-2183, 2012.

* cited by examiner

*Primary Examiner* — Nancy Treptow
(74) *Attorney, Agent, or Firm* — Norton Rose Fulbright US LLP

(57) ABSTRACT

The instant disclosure relates to the finding that lincRNA expression is associated with particular cytogenetic abnormalities and is related to disease pathogenesis of certain cancers. Long intergenic non-coding RNAs (lincRNAs) have been found to play a role in gene regulation, but their expression has not been described in B acute lymphoblastic leukemia (B-ALL). Methods and compositions are provided regarding B-ALL associated long intergenic RNAs (BA-LIRs).

20 Claims, 30 Drawing Sheets

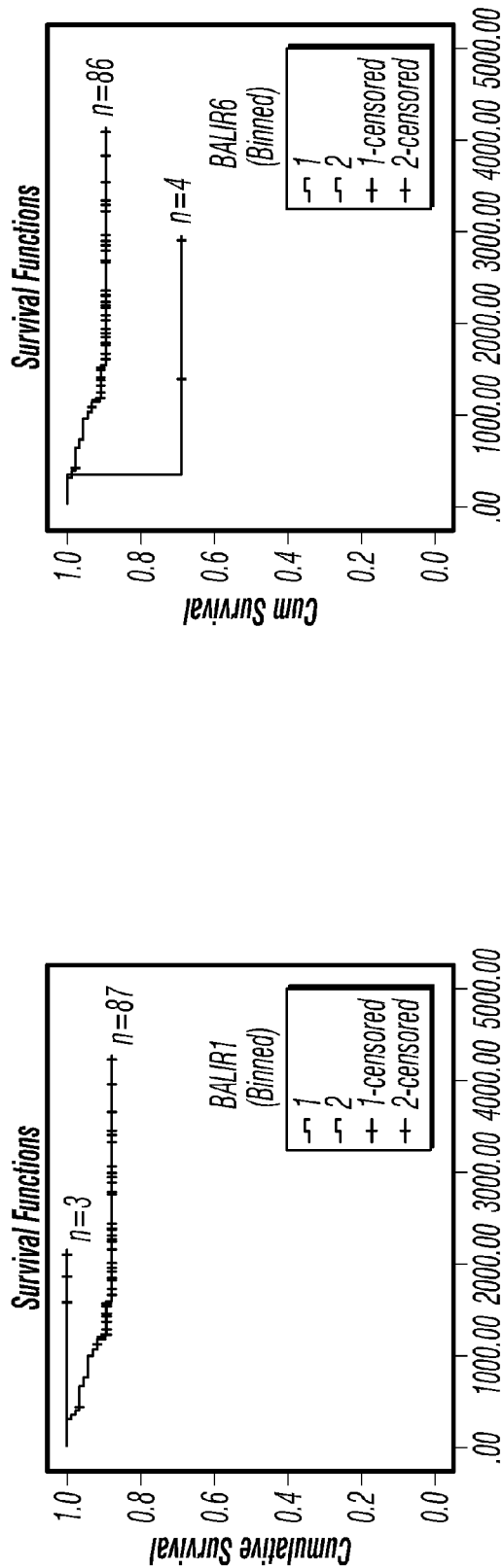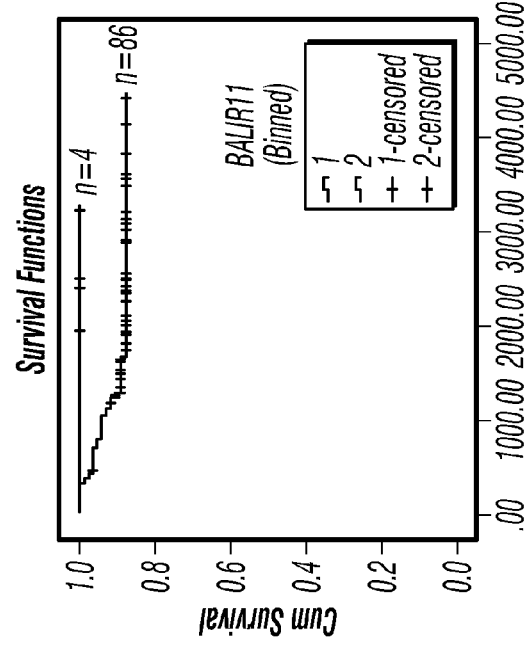
FIG. 8E
FIG. 8F
FIG. 8G

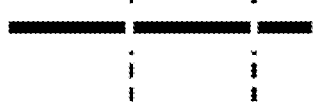
FIG. 12A-12B

SEQUENCE LISTING

<160> NUMBER OF SEQ ID NOS: 90

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gggacctggc ccctcaccaa                    20

<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

```
<400> SEQUENCE: 2
aggactgggc acatggaaaa aggt                                          24

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
agcagcaaag caaagcctgg ga                                            22

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
cacggcgtgg cagctttcag                                               20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
cgtgtgctgg ggaaggcact g                                             21

<210> SEQ ID NO 6
<211> LENGTH: 23
<212> TYPE: DNA
<213> ORGANISM: Artificial Sequence
<220> FEATURE:
<223> OTHER INFORMATION: Synthetic Primer

<400> SEQUENCE: 6
ccaggctcag agcaacacag gga                                           23

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
gctggagtgt gtgtgagtga acca                                          24

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
gctgagtctc tccactcagg ggg                                           23
```

```
<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
catgtacgtt gctatccagg c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
ctccttaatg tcacgcacga t                                              21

<210> SEQ ID NO 11
<211> LENGTH: 40
<212> TYPE: DNA
<213> ORGANISM: Artificial Sequence
<220> FEATURE:
<223> OTHER INFORMATION: Synthetic Primer

<400> SEQUENCE: 11
gatccacctc gagtatctag aatgctagct tgggcccact                          40

<210> SEQ ID NO 12
<211> LENGTH: 40
<212> TYPE: DNA
<213> ORGANISM: Artificial Sequence
<220> FEATURE:
<223> OTHER INFORMATION: Synthetic Primer

<400> SEQUENCE: 12
gatcagtggg cccaagctag cattctagat actcgaggtg                          40

<210> SEQ ID NO 13
<211> LENGTH: 49
<212> TYPE: DNA
<213> ORGANISM: Artificial Sequence
<220> FEATURE:
<223> OTHER INFORMATION: Synthetic Primer

<400> SEQUENCE: 13
atcggctgag tcgacggatc cctggaggct tgctgaaggc tgtatgctg                49

<210> SEQ ID NO 14
<211> LENGTH: 49
<212> TYPE: DNA
<213> ORGANISM: Artificial Sequence
<220> FEATURE:
<223> OTHER INFORMATION: Synthetic Primer

<400> SEQUENCE: 14
atcggctgag tcgacctcga gctggaggct tgctgaaggc tgtatgctg                49

<210> SEQ ID NO 15
<211> LENGTH: 60
<212> TYPE: DNA
<213> ORGANISM: Artificial Sequence
<220> FEATURE:
<223> OTHER INFORMATION: Synthetic Primer
```

```
<400> SEQUENCE: 15
atcgcaattg ctcgagtggg ccatttgttc catgtgagtg ctagtaacag gccttgtgtc    60

<210> SEQ ID NO 16
<211> LENGTH: 49
<212> TYPE: DNA
<213> ORGANISM: Artificial Sequence
<220> FEATURE:
<223> OTHER INFORMATION: Synthetic Primer

<400> SEQUENCE: 16
atcggctgag tcgactctag actggaggct tgctgaaggc tgtatgctg                49

<210> SEQ ID NO 17
<211> LENGTH: 60
<212> TYPE: DNA
<213> ORGANISM: Artificial Sequence
<220> FEATURE:
<223> OTHER INFORMATION: Synthetic Primer

<400> SEQUENCE: 17
atcgcaattg tctagatggg ccatttgttc catgtgagtg ctagtaacag gccttgtgtc    60

<210> SEQ ID NO 18
<211> LENGTH: 60
<212> TYPE: DNA
<213> ORGANISM: Artificial Sequence
<220> FEATURE:
<223> OTHER INFORMATION: Synthetic Primer

<400> SEQUENCE: 18
atcgcaattg gctagctggg ccatttgttc catgtgagtg ctagtaacag gccttgtgtc    60

<210> SEQ ID NO 19
<211> LENGTH: 60
<212> TYPE: DNA
<213> ORGANISM: Artificial Sequence
<220> FEATURE:
<223> OTHER INFORMATION: Synthetic Primer

<400> SEQUENCE: 19
atcgcaattg gggccctggg ccatttgttc catgtgagtg ctagtaacag gccttgtgtc    60

<210> SEQ ID NO 20
<211> LENGTH: 19
<212> TYPE: DNA
<213> ORGANISM: Artificial Sequence
<220> FEATURE:
<223> OTHER INFORMATION: Synthetic Primer

<400> SEQUENCE: 20
tggcacctga ccgagcacg                                                 19

<210> SEQ ID NO 21
<211> LENGTH: 17
<212> TYPE: DNA
<213> ORGANISM: Artificial Sequence
<220> FEATURE:
<223> OTHER INFORMATION: Synthetic Primer

<400> SEQUENCE: 21
tgacccgcga ggaccgc                                                   17
```

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
agcagcaaag caaagcctgg ga                                       22

<210> SEQ ID NO 23
<211> LENGTH: 21
<212> TYPE: DNA
<213> ORGANISM: Artificial Sequence
<220> FEATURE:
<223> OTHER INFORMATION: Synthetic Primer

<400> SEQUENCE: 23
gcagcaaagc aaagcctggg a                                        21

<210> SEQ ID NO 24
<211> LENGTH: 28
<212> TYPE: DNA
<213> ORGANISM: Artificial Sequence
<220> FEATURE:
<223> OTHER INFORMATION: Synthetic Primer

<400> SEQUENCE: 24
catgccaacc taatctgtgt taaaatgc                                 28

<210> SEQ ID NO 25
<211> LENGTH: 29
<212> TYPE: DNA
<213> ORGANISM: Artificial Sequence
<220> FEATURE:
<223> OTHER INFORMATION: Synthetic Primer

<400> SEQUENCE: 25
gcatatgaag gtcttgacct gagaaaacc                                29

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
cacggcgtgg cagctttcag                                          20

<210> SEQ ID NO 27
<211> LENGTH: 21
<212> TYPE: DNA
<213> ORGANISM: Artificial Sequence
<220> FEATURE:
<223> OTHER INFORMATION: Synthetic Primer

<400> SEQUENCE: 27
tcacggcgtg gcagctttca g                                        21

<210> SEQ ID NO 28
<211> LENGTH: 25
<212> TYPE: DNA
<213> ORGANISM: Artificial Sequence
<220> FEATURE:
<223> OTHER INFORMATION: Synthetic Primer

```
<400> SEQUENCE: 28
gatcaattta aggtaagtgg caggc                                          25

<210> SEQ ID NO 29
<211> LENGTH: 90
<212> TYPE: DNA
<213> ORGANISM: Artificial Sequence
<220> FEATURE:
<223> OTHER INFORMATION: Synthetic Primer

<400> SEQUENCE: 29
gaaggctgta tgctgagatt aggttggcat gattctgttt tggccactga ctgacagaat    60
catcaaccta atctcaggac acaaggcctg                                     90

<210> SEQ ID NO 30
<211> LENGTH: 90
<212> TYPE: DNA
<213> ORGANISM: Artificial Sequence
<220> FEATURE:
<223> OTHER INFORMATION: Synthetic Primer

<400> SEQUENCE: 30
gaaggctgta tgctgtttac tgaaatctcc taggtggttt tggccactga ctgaccacct    60
aggatttcag taaacaggac acaaggcctg                                     90

<210> SEQ ID NO 31
<211> LENGTH: 87
<212> TYPE: DNA
<213> ORGANISM: Artificial Sequence
<220> FEATURE:
<223> OTHER INFORMATION: Synthetic Primer

<400> SEQUENCE: 31
gtaggctgta tgctgtaagg taagtggcag gcatttgttt tggccactga ctgacaaatg    60
cctcacttac cttatgtatg atgcctg                                        87

<210> SEQ ID NO 32
<211> LENGTH: 85
<212> TYPE: DNA
<213> ORGANISM: Artificial Sequence
<220> FEATURE:
<223> OTHER INFORMATION: Synthetic Primer

<400> SEQUENCE: 32
gtaggctgta tgctgtttca cggtgtggca gctttcgttt tgcctccaac tgagaaagct    60
gacaccgtga aatgtatgat gcctg                                          85

<210> SEQ ID NO 33
<211> LENGTH: 87
<212> TYPE: DNA
<213> ORGANISM: Artificial Sequence
<220> FEATURE:
<223> OTHER INFORMATION: Synthetic Primer

<400> SEQUENCE: 33
gtaggctgta tgctgagatt aggttggcat gattctgttt tggccactga ctgacagaat    60
catcaaccta atcttgtatg atgcctg                                        87

<210> SEQ ID NO 34
<211> LENGTH: 87
<212> TYPE: DNA
<213> ORGANISM: Artificial Sequence
```

```
<220> FEATURE:
<223> OTHER INFORMATION: Synthetic Primer

<400> SEQUENCE: 34
gtaggctgta tgctgtttac tgaaatctcc taggtggttt tggccactga ctgaccacct    60
aggatttcag taaatgtatg atgcctg                                        87

<210> SEQ ID NO 35
<211> LENGTH: 90
<212> TYPE: DNA
<213> ORGANISM: Artificial Sequence
<220> FEATURE:
<223> OTHER INFORMATION: Synthetic Primer

<400> SEQUENCE: 35
gaaggctgta tgctgcagag tctgattacc tgctccgttt tggccactga ctgacggagc    60
aggatcagac tctgcaggac acaaggcctg                                     90

<210> SEQ ID NO 36
<211> LENGTH: 90
<212> TYPE: DNA
<213> ORGANISM: Artificial Sequence
<220> FEATURE:
<223> OTHER INFORMATION: Synthetic Primer

<400> SEQUENCE: 36
gaaggctgta tgctgccaaa tagcttgcag tgctgtgttt tggccactga ctgacacagc    60
actaagctat ttggcaggac acaaggcctg                                     90

<210> SEQ ID NO 37
<211> LENGTH: 90
<212> TYPE: DNA
<213> ORGANISM: Artificial Sequence
<220> FEATURE:
<223> OTHER INFORMATION: Synthetic Primer

<400> SEQUENCE: 37
gaaggctgta tgctgatatg ccaaatagct tgcagtgttt tggccactga ctgacactgc    60
aagatttggc atatcaggac acaaggcctg                                     90

<210> SEQ ID NO 38
<211> LENGTH: 475
<212> TYPE: DNA
<213> ORGANISM: Artificial Sequence
<220> FEATURE:
<223> OTHER INFORMATION: Synthetic Primer

<400> SEQUENCE: 38
agtcgcgtcg ggcctcccga gggggctgcg agtgtcagtc ggctctccgc acgtgtccgc    60
ggcctcgcgg agcagcactg caagctattt ggcatatgaa ggtcttgacc tgagaaaacc   120
atcttggata actgcagcaa ggaaaaggaa aaatgcaaca cctaggagat ttcagtaaac   180
agtagaatca tgccaaccta atctgtgtta aatgcttgg aatgtgggag ccgctgatga    240
tgcctcttgt ctgtgtgtct gactgaatcc tttcttttct cagagcagca agcaaagcc    300 tgggaaccag gccaaatgcc tgccacttac cttaaattga tcagccactt tgagattaaa   360 accccctgaaa gctgccacgc cgtgaaaaca aggcctcctt cacattaaag gcaaattgcg   420
actttgaaaa aaaaaaaaaa gaaaaaaaaa aaaaagtact ctgcgttgtt accac         475
```

```
<210> SEQ ID NO 39
<211> LENGTH: 21
<212> TYPE: DNA
<213> ORGANISM: Artificial Sequence
<220> FEATURE:
<223> OTHER INFORMATION: Synthetic Primer

<400> SEQUENCE: 39
agattaggtt ggcatgattc t                                      21

<210> SEQ ID NO 40
<211> LENGTH: 21
<212> TYPE: DNA
<213> ORGANISM: Artificial Sequence
<220> FEATURE:
<223> OTHER INFORMATION: Synthetic Primer

<400> SEQUENCE: 40
tttactgaaa tctcctaggt g                                      21

<210> SEQ ID NO 41
<211> LENGTH: 21
<212> TYPE: DNA
<213> ORGANISM: Artificial Sequence
<220> FEATURE:
<223> OTHER INFORMATION: Synthetic Primer

<400> SEQUENCE: 41
taaggtaagt ggcaggcatt t                                      21

<210> SEQ ID NO 42
<211> LENGTH: 21
<212> TYPE: DNA
<213> ORGANISM: Artificial Sequence
<220> FEATURE:
<223> OTHER INFORMATION: Synthetic Primer

<400> SEQUENCE: 42
tttcacggtg tggcagcttt c                                      21

<210> SEQ ID NO 43
<211> LENGTH: 21
<212> TYPE: DNA
<213> ORGANISM: Artificial Sequence
<220> FEATURE:
<223> OTHER INFORMATION: Synthetic Primer

<400> SEQUENCE: 43
agattaggtt ggcatgattc t                                      21

<210> SEQ ID NO 44
<211> LENGTH: 21
<212> TYPE: DNA
<213> ORGANISM: Artificial Sequence
<220> FEATURE:
<223> OTHER INFORMATION: Synthetic Primer

<400> SEQUENCE: 44
tttactgaaa tctcctaggt g                                      21

<210> SEQ ID NO 45
<211> LENGTH: 21
<212> TYPE: DNA
<213> ORGANISM: Artificial Sequence
<220> FEATURE:
<223> OTHER INFORMATION: Synthetic Primer
```

<400> SEQUENCE: 45
cagagtctga ttacctgctc c    21

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
ccaaatagct tgcagtgctg t    21

<210> SEQ ID NO 47
<211> LENGTH: 21
<212> TYPE: DNA
<213> ORGANISM: Artificial Sequence
<220> FEATURE:
<223> OTHER INFORMATION: Synthetic Primer

<400> SEQUENCE: 47
atatgccaaa tagcttgcag t    21

<210> SEQ ID NO 48
<211> LENGTH: 24
<212> TYPE: DNA
<213> ORGANISM: Artificial Sequence
<220> FEATURE:
<223> OTHER INFORMATION: Synthetic Primer

<400> SEQUENCE: 48
gctggagtgt gtgtgagtga acca    24

<210> SEQ ID NO 49
<211> LENGTH: 23
<212> TYPE: DNA
<213> ORGANISM: Artificial Sequence
<220> FEATURE:
<223> OTHER INFORMATION: Synthetic Primer

<400> SEQUENCE: 49
gctgagtctc tccactcagg ggg    23

<210> SEQ ID NO 50
<211> LENGTH: 21
<212> TYPE: DNA
<213> ORGANISM: Artificial Sequence
<220> FEATURE:
<223> OTHER INFORMATION: Synthetic Primer

<400> SEQUENCE: 50
ggggcaaggt ggaacagtta t    21

<210> SEQ ID NO 51
<211> LENGTH: 21
<212> TYPE: DNA
<213> ORGANISM: Artificial Sequence
<220> FEATURE:
<223> OTHER INFORMATION: Synthetic Primer

<400> SEQUENCE: 51
aggtcatcag ggatcttgca g    21

```
<210> SEQ ID NO 52
<211> LENGTH: 21
<212> TYPE: DNA
<213> ORGANISM: Artificial Sequence
<220> FEATURE:
<223> OTHER INFORMATION: Synthetic Primer

<400> SEQUENCE: 52
tccaagtgcc gaaaaaggaa g                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetic Primer

<400> SEQUENCE: 53
cgagttctga gctttcaagg t                                              21

<210> SEQ ID NO 54
<211> LENGTH: 22
<212> TYPE: DNA
<213> ORGANISM: Artificial Sequence
<220> FEATURE:
<223> OTHER INFORMATION: Synthetic Primer

<400> SEQUENCE: 54
taagttctga gtgtgaccga ga                                             22

<210> SEQ ID NO 55
<211> LENGTH: 22
<212> TYPE: DNA
<213> ORGANISM: Artificial Sequence
<220> FEATURE:
<223> OTHER INFORMATION: Synthetic Primer

<400> SEQUENCE: 55
gctctgtctg tagggaggta gg                                             22

<210> SEQ ID NO 56
<211> LENGTH: 22
<212> TYPE: DNA
<213> ORGANISM: Artificial Sequence
<220> FEATURE:
<223> OTHER INFORMATION: Synthetic Primer

<400> SEQUENCE: 56
taagttctga gtgtgaccga ga                                             22

<210> SEQ ID NO 57
<211> LENGTH: 22
<212> TYPE: DNA
<213> ORGANISM: Artificial Sequence
<220> FEATURE:
<223> OTHER INFORMATION: Synthetic Primer

<400> SEQUENCE: 57
gcacacatca aacaacctga cc                                             22

<210> SEQ ID NO 58
<211> LENGTH: 23
<212> TYPE: DNA
<213> ORGANISM: Artificial Sequence
<220> FEATURE:
<223> OTHER INFORMATION: Synthetic Primer
```

<400> SEQUENCE: 58
atggcaaagc aacttaacct tcc                                                23

<210> SEQ ID NO 59
<211> LENGTH: 22
<212> TYPE: DNA
<213> ORGANISM: Artificial Sequence
<220> FEATURE:
<223> OTHER INFORMATION: Synthetic Primer

<400> SEQUENCE: 59
ccattcacgt cttgttcagt ca                                                 22

<210> SEQ ID NO 60
<211> LENGTH: 23
<212> TYPE: DNA
<213> ORGANISM: Artificial Sequence
<220> FEATURE:
<223> OTHER INFORMATION: Synthetic Primer

<400> SEQUENCE: 60
catattatgt cggagcggaa tgt                                                23

<210> SEQ ID NO 61
<211> LENGTH: 21
<212> TYPE: DNA
<213> ORGANISM: Artificial Sequence
<220> FEATURE:
<223> OTHER INFORMATION: Synthetic Primer

<400> SEQUENCE: 61
tgtcagcagt ctggaaagag a                                                  21

<210> SEQ ID NO 62
<211> LENGTH: 20
<212> TYPE: DNA
<213> ORGANISM: Artificial Sequence
<220> FEATURE:
<223> OTHER INFORMATION: Synthetic Primer

<400> SEQUENCE: 62
accgcaacgt ggttttctca                                                    20

<210> SEQ ID NO 63
<211> LENGTH: 23
<212> TYPE: DNA
<213> ORGANISM: Artificial Sequence
<220> FEATURE:
<223> OTHER INFORMATION: Synthetic Primer

<400> SEQUENCE: 63
ttgaatccca tagctgcttg aat                                                23

<210> SEQ ID NO 64
<211> LENGTH: 20
<212> TYPE: DNA
<213> ORGANISM: Artificial Sequence
<220> FEATURE:
<223> OTHER INFORMATION: Synthetic Primer

<400> SEQUENCE: 64
cgctggtgat gtctgttgtc                                                    20

-continued

```
<210> SEQ ID NO 65
<211> LENGTH: 20
<212> TYPE: DNA
<213> ORGANISM: Artificial Sequence
<220> FEATURE:
<223> OTHER INFORMATION: Synthetic Primer

<400> SEQUENCE: 65
gaggccttgc tttcactgag                                                  20

<210> SEQ ID NO 66
<211> LENGTH: 19
<212> TYPE: DNA
<213> ORGANISM: Artificial Sequence
<220> FEATURE:
<223> OTHER INFORMATION: Synthetic Primer

<400> SEQUENCE: 66
aagcgaaact ggcggaaac                                                   19

<210> SEQ ID NO 67
<211> LENGTH: 20
<212> TYPE: DNA
<213> ORGANISM: Artificial Sequence
<220> FEATURE:
<223> OTHER INFORMATION: Synthetic Primer

<400> SEQUENCE: 67
taaccgatgt tgggcatcag                                                  20

<210> SEQ ID NO 68
<211> LENGTH: 19
<212> TYPE: DNA
<213> ORGANISM: Artificial Sequence
<220> FEATURE:
<223> OTHER INFORMATION: Synthetic Primer

<400> SEQUENCE: 68
cgggtttcaa cgccgacta                                                   19

<210> SEQ ID NO 69
<211> LENGTH: 21
<212> TYPE: DNA
<213> ORGANISM: Artificial Sequence
<220> FEATURE:
<223> OTHER INFORMATION: Synthetic Primer

<400> SEQUENCE: 69
tggcactaga gacggacaga t                                                21

<210> SEQ ID NO 70
<211> LENGTH: 19
<212> TYPE: DNA
<213> ORGANISM: Artificial Sequence
<220> FEATURE:
<223> OTHER INFORMATION: Synthetic Primer

<400> SEQUENCE: 70
ttcctccagt ccgagagcg                                                   19

<210> SEQ ID NO 71
<211> LENGTH: 21
<212> TYPE: DNA
<213> ORGANISM: Artificial Sequence
<220> FEATURE:
<223> OTHER INFORMATION: Synthetic Primer
```

```
<400> SEQUENCE: 71
tgagaaggtc cgagttcttg g                                      21

<210> SEQ ID NO 72
<211> LENGTH: 20
<212> TYPE: DNA
<213> ORGANISM: Artificial Sequence
<220> FEATURE:
<223> OTHER INFORMATION: Synthetic Primer

<400> SEQUENCE: 72
cgacagtctc aggaggaacc                                        20

<210> SEQ ID NO 73
<211> LENGTH: 20
<212> TYPE: DNA
<213> ORGANISM: Artificial Sequence
<220> FEATURE:
<223> OTHER INFORMATION: Synthetic Primer

<400> SEQUENCE: 73
ccttctccat accagacgga                                        20

<210> SEQ ID NO 74
<211> LENGTH: 21
<212> TYPE: DNA
<213> ORGANISM: Artificial Sequence
<220> FEATURE:
<223> OTHER INFORMATION: Synthetic Primer

<400> SEQUENCE: 74
tctcacagag tagtgcatcg t                                      21

<210> SEQ ID NO 75
<211> LENGTH: 22
<212> TYPE: DNA
<213> ORGANISM: Artificial Sequence
<220> FEATURE:
<223> OTHER INFORMATION: Synthetic Primer

<400> SEQUENCE: 75
cgaggtaagg gccatctgaa aa                                     22

<210> SEQ ID NO 76
<211> LENGTH: 24
<212> TYPE: DNA
<213> ORGANISM: Artificial Sequence
<220> FEATURE:
<223> OTHER INFORMATION: Synthetic Primer

<400> SEQUENCE: 76
ggtaaccagg gcaaggaaat gcaa                                   24

<210> SEQ ID NO 77
<211> LENGTH: 25
<212> TYPE: DNA
<213> ORGANISM: Artificial Sequence
<220> FEATURE:
<223> OTHER INFORMATION: Synthetic Primer

<400> SEQUENCE: 77
gcaaacagta gaatcatgcc aacgt                                  25
```

```
<210> SEQ ID NO 78
<211> LENGTH: 90
<212> TYPE: DNA
<213> ORGANISM: Artificial Sequence
<220> FEATURE:
<223> OTHER INFORMATION: Synthetic Primer

<400> SEQUENCE: 78
gaaggctgta tgctgaaatg gtttcctcag gtcaaggttt tggccactga ctgaccttga    60
cctggaaacc atttcaggac acaaggcctg                                     90

<210> SEQ ID NO 79
<211> LENGTH: 21
<212> TYPE: DNA
<213> ORGANISM: Artificial Sequence
<220> FEATURE:
<223> OTHER INFORMATION: Synthetic Primer

<400> SEQUENCE: 79
aaatggtttc ctcaggtcaa g                                              21

<210> SEQ ID NO 80
<211> LENGTH: 90
<212> TYPE: DNA
<213> ORGANISM: Artificial Sequence
<220> FEATURE:
<223> OTHER INFORMATION: Synthetic Primer

<400> SEQUENCE: 80
gaaggctgta tgctgtaagg taagtggcag gcgcttgttt tggccactga ctgacaagcg    60
cctcacttac cttacaggac acaaggcctg                                     90

<210> SEQ ID NO 81
<211> LENGTH: 21
<212> TYPE: DNA
<213> ORGANISM: Artificial Sequence
<220> FEATURE:
<223> OTHER INFORMATION: Synthetic Primer

<400> SEQUENCE: 81
taaggtaagt ggcaggcgct t                                              21

<210> SEQ ID NO 82
<211> LENGTH: 90
<212> TYPE: DNA
<213> ORGANISM: Artificial Sequence
<220> FEATURE:
<223> OTHER INFORMATION: Synthetic Primer

<400> SEQUENCE: 82
gaaggctgta tgctgattta aggtaagtgg caggcggttt tggccactga ctgaccgcct    60
gccttacctt aaatcaggac acaaggcctg                                     90

<210> SEQ ID NO 83
<211> LENGTH: 21
<212> TYPE: DNA
<213> ORGANISM: Artificial Sequence
<220> FEATURE:
<223> OTHER INFORMATION: Synthetic Primer

<400> SEQUENCE: 83
atttaaggta agtggcaggc g                                              21
```

```
<210> SEQ ID NO 84
<211> LENGTH: 374
<212> TYPE: DNA
<213> ORGANISM: Artificial Sequence
<220> FEATURE:
<223> OTHER INFORMATION: Synthetic Primer

<400> SEQUENCE: 84
cgcagcaaag ccaagcctgg gaaccaggcc aagcgcctgc cacttacctt aaaattgatca    60 gccactttga gattaaaacc cctgaaagct gccgctcagt gaaagcaagg cctctttcac   120
attaaaggca aattgcgact gtgggtttgc tgtgatcgcc ctctctctct ctctctcctt   180
ttttccccct attttacccg ttttttttcag tgtggacttt tttctctctc ctctttccat   240
ttatgcttcc atgtagaagc caatagttat agcatcttag ccaagcattc attaaggttt   300
ataagaacaa aatttatggt tatttagaag ttggcacaga gatcaattgt tgctagaaaa   360
aaaaaagaaa gaaa                                                     374

<210> SEQ ID NO 85
<211> LENGTH: 7484
<212> TYPE: DNA
<213> ORGANISM: Artificial Sequence
<220> FEATURE:
<223> OTHER INFORMATION: Synthetic Primer

<400> SEQUENCE: 85
gcctagtaga gatctggagc cagaagccca gagacagccg agtgcgccgt gcggtctccg    60
gacgctcgct gctcagcccg atccccgcca actgtgcagg cggctgaccc gcagcggcag   120
cggcagcagc gaggactcga gcgctggctg cagcgacacc atggatctct cctttatggc   180
cgcgcagctg cccatgatgg ggggagcttt catggactcg cccaacgagg acttcagcac   240
cgagtactcc ctgtttaact cctctgccaa tgtccacgcg gctgccaatg ccagggcca   300 gccggaagat cctcctcggt cctccaacga cgccgtcttg ctatggattg ccatcatagc   360
tacgctgggg aacatcgtgg tggtgggcgt ggtgtatgcc ttcaccttct gaggacggca   420
caccctgcac caccatgggg tgaggcttgg cacgtagctc tgacttgctg tcggcctttg   480
gcttctcctg tgttctagaa ccaggagttt tgaccagggg cggcggccgt ccttctggaa   540
tttctcccca gcagccctga tttcaaatat cccatgttgt ggtcaagctg agtcagaaga   600
catggaagta tgggcctcct gccctagag gcatgacggg gcaaggcctt cagagggcag   660
attggggatc cttgaaacta cattccagga acatgggacc agatgagaca gctagttaag   720
tttaaaacat agacatgatt tgatgatcgc ttgctggtgg taaataatca ctcgtgtgac   780 ttgttttat gcaaacttat cgaacctagg gcgtggggtg ctggggcaag agcagccctc   840
agaacttcag tgttcctgac ccaattctgg tttcacattc agtcccttgg ccatctagta   900
gggccattgg atgttcctag tttgactttg aaatggcacc tttgccacca gacacctggt   960
cccttccaag acccaagtgc attgggagac ccagggatgg ggggttactg gtaataggtg  1020
gggtttctgg gggtgttgtt ggtggttttt atctcctggt cggactttct cttctttta   1080 agaagaggag aggatgtctt taagagctag atgtgccagg cagtggactc ttcaggccac  1140
ccacgtgaga atgctgtttc ttctctgagg aatcgtggaa ttttaaagat gaacaagatt  1200
cacatccact gaattattca acggatgggt cagaaagggg ggtgatttgc ctgtggtcac  1260
caggcaggtt tgtggaggag tcggaacaga agatgtgtc ctcactctca gctcactgag  1320
ctctctgccc caactaagca cttccctgag gaggttgctg agaagctgcc ctcaggagaa  1380
```

-continued

| | |
|---|---|
| tgtccaggca tcttgaaggt gggtgcgaga ttggcaggct gctcagatac ccgtcccttta | 1440 |
| cattcagtgt ggataccgtg cattctcctg aagctgtgaa agtgcttctg cccaagccac | 1500 |
| ttccttaaat tctgaaatat cagcatctgg ggtcctggca agcaaggaag cttccaagta | 1560 |
| aaaaccagag agaagggcac acttttcttt cttcattagg aaatcttatt gcacaggaac | 1620 |
| caccccacc cccaccccc acaccttccc aaggcagcat cccagtgcag atagagtggg | 1680 |
| aaaggtccca gaagggggct cactcacctc taggcccaga gaggctttct cctcacttta | 1740 |
| tacactgcaa aaacagaaga attgtgtcaa taacaccctc tgtagtggag aaacttaaaa | 1800 |
| agctggttag gaagctctcg tgtatattta gagacaatta caagaaagct ggacttgccg | 1860 |
| ctgtggtctc aggagaaatg agtgttcttg atgacaggca aagggacatc ttagttgtcc | 1920 |
| agaagcggca ctcttccctg gaagccgcca tgttaatagg attactagcc tggctccaga | 1980 |
| cagtgcctgc tcatggctgc cagttcttac cgatcacatc tgtcactgcc accgtatatc | 2040 |
| atctgccagt gcatcagctt aaggggaggt cacgagtgca aaagaacctg acccttgaca | 2100 |
| atgagggaga agggacatgg accacctgtc tggaattcct ggaatcactg gcagggtgga | 2160 |
| ggctgggctg gggagttagc cgcggtgtgc gtgaatggct ctgtctccag caagtctctc | 2220 |
| tccatcaaac cccaggtctg ccccataagc aagatcttta acagatggat gtctccatga | 2280 |
| gaaaacccaa ggcgagaagc ccagagccat ggcggggttg cttgacgtcc tcatggagtc | 2340 |
| actctgcccc acatgctcaa atcttccctc tggccccaca tccctaggag ggcctgaccc | 2400 |
| ctgtaaagat acaggaggca gctccctggc ctccaaatgg cccatggaga tggcagtcgg | 2460 |
| gagacagggt tctgtgtttg ctgcggtgaa gggaggagaa ggcaggagga aaaaggatgg | 2520 |
| cttctagccc tgaagaggac tccagcatcc caggcacccg gtgcttctgg ctgcagtttt | 2580 |
| ccctatggag gcccctcagc ctccagccct aacataaatg tcggttaaat tcagttttca | 2640 |
| agcctctctc ccttttcagt gtcagagcag tagatggtcc agggcattgg aggcctcgac | 2700 |
| cactctgcat tgcagattac agtgacttcc tcggggttgc cccatcttgg tctcctgtgg | 2760 |
| tttcttcatc agcttttttt ttaccagcat ctctcaaata caatgaaga tagatatgcc | 2820 |
| cattagtgtc tgattaagga gcaaaggctg gatttctggc cacagcgagc tgcactctcc | 2880 |
| ctcctgcctc agccggggtc cgtcttagca gtttggaaag gggaaaaaga tgccggtcct | 2940 |
| cactgcttaa gttttgtgtc caggtgccac tagacttgca tgcacactaa ctccttacaa | 3000 |
| tcaccacaca gcatcatcgc cccagtgcac agatgaggaa ccagaggctc agaggagtga | 3060 |
| agttgccttc ctgaggtcac acagcatgaa agtgatgagc taggatttga atctgggaag | 3120 |
| ttgggctcta gagccagact gtactgcctt ctgccacact gtactgcctt ctgtgactgg | 3180 |
| gtggcacctc cagggcacat ttacacaagg ccctgaatct gcagaggctg tttctcaaga | 3240 |
| tgcccgtcat ggtgtggcct gggccagctc tggcttccac aggtccctga ctgtcctcag | 3300 |
| agtggaacat gctcaacctc ccgcccactg ctctctctct gcccagattt caggggtgcc | 3360 |
| ggtccccaag gcctgccccc ttctttaaga ctgaactcaa gtctccttgg aaggccccgg | 3420 |
| tgaagctccc agagactggt tttcttggga tgcaggcaga aggggaccct ccctggccaa | 3480 |
| cacccaggag cccagcagaa gcacccacac gtagaaagag gctcactaca gccagaagtg | 3540 |
| cagagtcaga gtcctgggac catcttgttc tgcaaggtga cccaggctc cccaggacag | 3600 |
| gggagaggga tcgtcctcat tcagactcta gctggggcct ctgtactggc ttctccttgg | 3660 |
| gtggggttgc ctgttacata gctgtgcctc agagaaaggg tcctgcattt tctgaatgt | 3720 |
| tctctgtgct taccctctg tgtgcccctc cattgctcct ctacaagcaa ttaggtgatt | 3780 |

| | |
|---|---|
| caaaagagca acttaggctg ggtgcagtga ctcacacccg taatcccggc actttgggag | 3840 |
| gccgaggcgg gcagggacag gagttcaaga ccagcctggc caacatggtg aaaccctgtc | 3900 |
| tctacaaaaa atacaaaaat taaccagaca ttgtggcatg tgcctgtaat cccagctact | 3960 |
| caggaggctg acacaggaga attgcttgaa ccaggaggcg gaggctgcag tgagctgaga | 4020 |
| ttgtgccact gcactccagc ctgggcaaca caacgagact ctgtctcaaa aaaaaaaaaa | 4080 |
| agaaaagaaa aaaaaagag caacttactg ctttgtgagg ttgtgagtgg ccaccactga | 4140 |
| aggtctttga gaagaggcca gacgccgctg tagccaggcc tgtcttaaga ggacttgtgc | 4200 |
| ttccagggac ccaggcagga tgatggcgca gctcttccta ctccaagcca acgctgtcct | 4260 |
| tccccttttcc catgaaatca aggtcaagag gcaaataaga ctccctgctc cactctaccc | 4320 |
| cccagagaga aatgattctc gctcctttca gatcccccag gatctgaggg agaaaggatg | 4380 |
| ggaggagggg cagcagcatt tcgctggaaa ggcagcagat gcttttccag ccccggttca | 4440 |
| gctggaaggc ttggaggccg gccagaccac tctggcgtct cctgaagtgg gtccctggag | 4500 |
| accgaagagg ctcagtggag tctgtctgtt gtcagcactg ctgcctgatc cctgcaagac | 4560 |
| aaatggcact ttccttcttc agaagcatca tctgccttca ttattagcag taatattatt | 4620 |
| cccagttatt attcttaccg gtgccagttt tgcacatctt tttgttgctc tatttgtgtc | 4680 |
| tcatttactt ctcaaattgc ccctgggggc aggaatgagg atgcagagag atgcacgtta | 4740 |
| attactgtcg cattttttctg tggagaaaac tgaggcaggg gctgaacgct cacagctaag | 4800 |
| gagctgtgat tcagacccag ttctgtcagc tctagaggca ccctgcatca tgcccaccag | 4860 |
| ggtgatcccc ctgggatgga ccatctcggg atatgaggcc tcggaggctg gggttgagat | 4920 |
| ttggtcctga agagcttata gccagattgc cacattcaag tgtaagtcca ggaaaggggc | 4980 |
| aggcggcagt gcacagggat ttatcagttc cagaacctca cagtgataag aggctttaga | 5040 |
| gagcatctaa tcgagacctt taattttttcg gggagagcag ctgaggccgt gtggaaaatt | 5100 |
| agtggagagc tgacaagtgt ctgggctcct ggcccagggg tccgtggtcc agcacgttgt | 5160 |
| gcgttcagtg ggaagcaaag ggcttgcccg ggattacctg ccccagcccc gaggtgggtt | 5220 |
| gtgctccctg cagctgccat cggcccgctt tgcttcgtcc tggcagatgc ccagtgattg | 5280 |
| tccccgagca agtgccaggg ttgggctgag ctgctatgac agggaggccc agggagttct | 5340 |
| gctcagggag ccaaagggaa cagccagatc ctgaatgttc tatgttcacc tgccccagcc | 5400 |
| ccacccaccc tggcccactc cacaggcccc tgaccatggt cactcacgga gagggatgga | 5460 |
| ggagaaggtg gttgaactga gtactgagaa cccagaggac agagcccaca gcttccaagc | 5520 |
| aggaaaaggg acctctctga aaaatctgga taaccagaat tatcacagca ccctctcatt | 5580 |
| cccagcgcgt ccttctgagc tcagaccttg agcattact gggtttcttt ttgaggaaga | 5640 |
| gggaaagtga caaaggacaa aacaatgcaa atcttcatga ctgaagacga tcaaagactc | 5700 |
| cctggagcga gaaacagtt actgccagaa gcagaatgga agagccaaaa agtacacaaa | 5760 |
| atggacgcca taaattctga aataaaagtg tatgatgtgt tctgagtcac tgtagaagtc | 5820 |
| atgcatttat tatcaagata gaaagagca gagaatgacg tggacattgg tcctcggaga | 5880 |
| ggctgcatag gtggtgcggt ccccggggga ttctggatgc tggtcttttg accgtggcgg | 5940 |
| cagcctcgcg cctgcccgga tggctccatc cagacatttg gcaaggctgt catctgctct | 6000 |
| tgggtccttt ttcaagctga tttcctgcct ccccaagagg aggtttgagc ccattctgc | 6060 |
| cttggaaata aatcctgaca gatgtgcaca gcatatttgc agggaatttg caggcctcga | 6120 |
| ttattggggg aatcagagcc cattccacac cgagcccccat ccacgtggct gagcaacacc | 6180 |

```
cctgtgtccc ctgtatctgt ctcactggct gtctttctgc cagtttctta aagaaccaca    6240
ccattactgc atttgccgtt cgaagcgttg tcccaacaat gcagatggtt ctgacaaggg    6300
tctatatgct ggcagaaggg agcttccaac cttttaactt gaggaaaatg aatctctgac    6360
aggcttgaga gtgttgccag gtggagcttt tcaggagaca ggggtcttga gcccaggaca    6420
cctaactatc gagttttcac taggagactt agtggtggct ttcatgaggc cagtcgttct    6480
caaggaaggg ctgggggcca tcagcaatgt ctggagacat ttttgattct cacagcttgg    6540
tggggactgc tattggtatc tcatgggtgg aggccaggga tgccaccgaa catcctacaa    6600
tgcacagggc agccccccac aaataagaat tatccagccc caaatgcca atagtgccga     6660 ggtcagggga ccctgtgctg gccatcctat ctctgattct gaaactatgc atgctttcca    6720
cttttcccca tttgtgagtc attgagtaaa ttaaagctct tctgagcagc agcagtgatc    6780
atggtcactg ccctgcgttc aaataatgcg agctgaggac agtgatctgc aactcccagc    6840
atgtcatgtg gtctcttaga aatccatgtg actgtttcca ccatcttggg catttgtggg    6900 gaccccaga ctgagggag aaagcccctac aaagtggatg ggagtgtggg gctgaacttt      6960
tccctaccct taactttgtg tctctgggac ctccagggac ctggcccctc accaatgcat    7020
atgaagagta tgcttgggga agagcttagg aatggggtgg gcatgggagt gctgggtagc    7080
agcctttgag caaatctgca tcttctctta tttctgacct ttttccatgt gcccagtcct    7140
atttctgcca gttgaaggca tactaatatt ctttatacta tttaatcttt tgcagaaacc    7200
ttactattat aacttgctac tctccagata ccaattcttc atgccgagag catcggaaat    7260 gttttgtgt cttactgatg ttttcatgat caacttgtaa tgtaagcagt tgacttcata     7320
aaaggtattt taactattct tggagtcctt tgctacccaa gcacctggtt tcaccatgcg    7380
atcactgact tctctacagt gaagactctt tcttaataaa ggatttcgct gtgctctttt    7440
gattaaaaat atctaacctt aaaagacgta aaaaaaaaa aaaa                      7484

<210> SEQ ID NO 86
<211> LENGTH: 2352
<212> TYPE: DNA
<213> ORGANISM: Artificial Sequence
<220> FEATURE:
<223> OTHER INFORMATION: Synthetic Primer

<400> SEQUENCE: 86
ccacgcgtcc gggactgagc actgggagac tccaatgggg agaaggggag gaacaagcaa      60
aaagatggag aaaaagctac caccagtgac ctaggagaac caggggggctg gcatcctgca    120 gccacatgca catggaagat cactttgatt gccatgtgga gagtgaactg tgggaggacc     180
ccagtggagg caggaagact aaaccagaag acagtcaccg tagtccagat aagagatgca    240
tatgttatca atcgccatgt gaagaagatg cttgcttccc ctttgccttc tgccatgatt    300
gtgagtttcg cgaggcctcc acagccatgc ttcctgtact gcagaactgt cttcgattag    360
atattacttc ttctgaacaa tcttccttga tgacccagct actttacatc tctggatgga    420
atcctcctct ttgctctaat ggcatggtgt gcagaagtca gctgtgaaaa ggaggaatga    480
aagcaagtga aggatgccct tcataaggaa caagcgatcc tctaaaaacc aatcctagag    540
tatggcttca gattctgctc ccatttctca atgattatga gttttgtgcc acatcttctc    600 ccccttttatc cctacaatat ttgcatttca tgttttttatt ctcttactgc ctgagcaatt   660
tgaaactctc atatttaggc aattcccaga tctcgttctt aaagcattgt gattcccttt    720
cagcttttca gaggcacgtg tgctggggaa ggcactgagt cctccctgtc aatccaattt    780
```

```
gtgataagga tttccccagg tgcacccatt ccatagtccc tgtgttgctc tgagcctggt    840
tggcatcctt tgggaagca tttgtattgc ttttcatct cagaaaagat actctagtca      900
caaaccagtc atctgcctgt taagctgtat ttagaacaaa tcactccgaa gcaaaacaac    960
gatgacaaca acaaaagagc cacacttatt tctttctaga cttttaacaa atgtttgat   1020 gttgtggaga tttccaaaca attaatgtga aattgggtac tgttgttcac atgatttatt  1080
taccatatat agagaattca gctggagtgc tactgtcaat gatgctccca atgaaatttc   1140
agcagagagt tggaaaatca gcaaattgtt tatttccaaa gaggaattac attttcaaag   1200
gataaaagtt aataggagtc atagtgctca aaaaccacac gatataggaa aacctacccc   1260
actccaccaa agggcacatc ttgctttgaa cacttgattt catattaaca gttcatgagt   1320
tattcaaagc aggggaatcc ctgcaggttg ggaaatatcc tagtgctttt catagccttc   1380
catgtcatgg atcagggaca cacacttgtg cacatgtgtg cacagacaca aaacagagag  1440
aatgcttaac aggagcacat tttacaaaag tgagatccca ggcctggaaa atcccaaact   1500
cttataaatt ttacaaatcc aaaatggaat attcaaaaag aactcaacct gtttctcttg   1560
agtaactttt cagactctca ttacaggccc catgaggtca gtcagatttc tgttctacag   1620
gatactgcaa aaagagacca gaaatttaaa aaggagtgat ggtaccacac aaaatagtaa   1680
aaatgaaata gagaaggtgt gaagttagat ccttgattta tgtgtggaaa gctagtgcca   1740
agaatattgt tatgggcctg gctcctagag gcaagatttg ttagcaaact gtctctaaat  1800
atttatgctc agctaaataa ttgctaaata attccggatc ccagctggaa atctaggatc   1860
aggactagcc taaattagta gatctatgtg atagtatatt ggtattttat ccagaaagta   1920
cttgctcaat gataggttca acttcagcat ataattcata tacttttata aaagcctttt   1980
catggcatta catagaaggc cttttccttgg aaatatttcc ataaaataaa caaagcactt   2040
aaatcagtcc attcaatagc atttgttta ggattatta agaaatacag agttttgact     2100
tccgcagtgt gctaacatgg attattcttt catttgctga tccttgtatg tgcagtagga   2160
tgttgaaagt gggggtggtg gcagcatatt tctacatcac cttggactttt accttttctga  2220 gaatcaacat aggtttctaa ctttttttat ggccctgact ggtgcttcag taaacccacg   2280
aataaaagca gtactccaat ctgcagagac tctagaagaa aatactttct atgaaccaaa    2340
aaaaaaaaaa aa                                                        2352

<210> SEQ ID NO 87
<211> LENGTH: 638
<212> TYPE: DNA
<213> ORGANISM: Artificial Sequence
<220> FEATURE:
<223> OTHER INFORMATION: Synthetic Primer

<400> SEQUENCE: 87
tttcttcata ctatccagag ctccaaactt tgtaggaagc cagaagcgtc tcctttgttg     60
aacagtgcca aaatagcagc tctatccttt cctctctcct ctttctgatt ccagtcaata    120
tgtgttatgg agtctgtggt ctccacaagg ccttgggata ggcatccaaa ggaagatcac    180
tttgattgcc atgtggagag tgaactgtgg gaggacccca gtggaggcag gaagactaaa    240
ccagaagaca gtcacagtag tccagataag agatgcatat gttatcaatc gccatgtgaa    300
gaagatgctt gcttcccctt tgccttctgc catgattgtg agtttcgcga ggcctccaca    360
gccatgcttc ctgtactgca gaactgtgag tcaattaaac ctcttttctt cataaattac    420
ccagtctctg gtagttcttt atagcagtgc aagatggact aatacaccac ctaagtgatg    480
```

```
tatttgttgc tccagctcta tatataccta atttgtacat cacctgggac cttgcttttc    540
tttgagttaa atgattttat atgttaacta ctctactta atgatcacaa tttatcatat    600
actttttcag catctcaata aagaaattt tttcgaaa                             638

<210> SEQ ID NO 88
<211> LENGTH: 551
<212> TYPE: DNA
<213> ORGANISM: Artificial Sequence
<220> FEATURE:
<223> OTHER INFORMATION: Synthetic Primer

<400> SEQUENCE: 88
ctttcttcat actatccaga gctccaaact ttgtaggaag ccagaagcgt ctcctttgtt     60
gaacagtgcc aaaatagcag ctctgaagat cactttgatt gccatgtgga gagtgaactg   120
tgggaggacc ccagtggagg caggaagact aaaccagaag acagtcacag tagtccagat   180
aagagatgca tatgttatca atcgccatgt gaagaagatg cttgcttccc ctttgccttc   240
tgccatgatt gtgagtttcg cgaggcctcc acagccatgc ttcctgtact gcagaactgt   300
gagtcaatta aacctctttt cttcataaat tacccagtct ctggtagttc tttatagcag   360
tgcaagatgg actaatacac cacctaagtg atgtatttgt tgctccagct ctatatatac   420
ctaatttgta catcacctgg gaccttgctt ttctttgagt taaatgattt tatatgttaa   480
ctactctact ttaatgatca caatttatca tatactttt cagcatctca ataaaagaaa    540
ttttttcgaa a                                                        551

<210> SEQ ID NO 89
<211> LENGTH: 1557
<212> TYPE: DNA
<213> ORGANISM: Artificial Sequence
<220> FEATURE:
<223> OTHER INFORMATION: Synthetic Primer

<400> SEQUENCE: 89
ctctctctct ctcctgct gcattgtgaa gaaactgctt gcttccctct caccctctgc      60
agtttcctga ggcctcccca gccatgcgga acgctgtaga ccaagacctg gaattaacac   120
atcagaagat tctatgggga aacccattta aaaataggat gcatttttt cttttctgca    180 cagggagaaa gttaagctc tcctcactat gagttttcaa gtataaaga ctttttcttc     240 cacgattttg agaacaactg aggactcttg tgaccaggac aacagggaag cttgcagcaa   300
gatagctcca ggttggattc atgcttcgca ccccaagggc tgccagccag agaggaggag   360
aagcaatcac tcctgcagtt tctgaacact acacagacgc caggtagctt cttcaggaga   420
acagccctct gaggaggcag gaagaggagg cttatctttc agcagccgga gctgctgaga   480
tctctgggca gattaagctc tctctaatgg atgggctcca gcctggcaca ttcagtggag   540
agggatccac tcatccatca tcaacataat atggtcctcc ctgcacttca cagtgtcctc   600
ttgctattga aaaggctttt ttgccttctc aagtttcttt gtcaacagtc tacaggaaga   660
agctcaggcc gccaccggca gaggtgaatg caagctcacg ttttatttct gactgcttaa   720
tcattgcctc gatcactgct caagctctgc ctttgtttcc aaaggttacc tgtgggaaaa   780
cttctttttc tatgctgaaa ttaataggga ggcaaagatg agtccactga taagcagagc   840
cttaaaactc acatagagaa acaactttgc tggagtgtgt gtgagtgaac cactaaggaa   900
tcagatagtg tgatggcagt tatcattgca ggttaagaca tttctacaaa tatttcgaca   960
tctccatata ctcactcctt tcccccctga gtggagagac tcagctaccc agagaggaag  1020
```

-continued

```
ctcaaaaaaa acagaagctt caaacaaaca accaaccaaa aaaaaaaaaa actgtgggtt    1080
catcagaggt ggtagggaag acaaaaacat gggaggagca gctgggcacg gtggctcaag    1140
cctgtaatcc cagcactttg cgaggctgag gtgggtggat cacctgaggt caggagttcg    1200
agaccagcct ggccaacatg gtgaaacccc atctctacta aaaatacaaa aaattagccg    1260
ggcgttgtgg tacgcacctg taatcccagc tactccggag gctgaggcag cagaatcgct    1320
tgaacccagg aggcagaggt tgcaacgagc caagatcgca ccattgcact ccagcctggg    1380
caacaagagc gaaactccat ctaaaaaaaa caaacaagca aacaaacaaa aaacacggga    1440
ggagcaataa aaaggaatcc atgctttgat ttttttttt agtgagagga agggaaggct    1500
gctgcctctc acttctccct gttttgttgt tcttttaagt agcatgtgtc actctgt      1557
```

<210> SEQ ID NO 90
<211> LENGTH: 323
<212> TYPE: DNA
<213> ORGANISM: Artificial Sequence
<220> FEATURE:
<223> OTHER INFORMATION: Synthetic Primer

<400> SEQUENCE: 90

```
cctttgtttc caaaggttac ctgtgggaaa acttcttttt ctatgctgaa attaataggg     60
aggcaaagat gagtccactg ataagcagag ccttaaaact cacatagaga aacaactttg    120
ctggagtgtg tgtgagtgaa ccactaagga atcagatagt gtgatggcag ttatcattgc    180
aggttaagac atttctacaa atatttcgac atctccatat actcactcct ttccccctg    240 agtggagaga ctcagctacc cagagaggaa gctcaaaaaa aacagaagct tcaaacaaac    300
aaccaaccaa aaaaaaaaaa aac                                            323
```

METHODS AND COMPOSITIONS INVOLVING LINCRNA AND LEUKEMIA

CROSS-REFERENCE TO RELATED APPLICATIONS

This application is a national phase application under 35 U.S.C. § 371 of International Application No. PCT/US2014/027313, filed Mar. 14, 2014, which claims the benefit of priority to U.S. Provisional Patent Application Ser. No. 61/783,266, filed Mar. 14, 2013. The entire contents of each of the above-referenced disclosures are specifically incorporated herein by reference without disclaimer.

STATEMENT OF GOVERNMENT RIGHTS

This invention was made with Government support under CA133521, awarded by the National Institutes of Health. The government has certain rights in the invention.

BACKGROUND OF THE INVENTION

1. Field of the Invention

The present invention relates generally to the field of molecular biology and medicine. More specifically, it concerns diagnostic, prognostic, and therapeutic applications for cancer involving lincRNA.

2. Description of Related Art

Acute lymphoblastic leukemia (ALL) is a form of leukemia, or cancer of the white blood cells characterized by excess lymphoblasts.

Malignant, immature white blood cells continuously multiply and are overproduced in the bone marrow. ALL causes damage and death by crowding out normal cells in the bone marrow, and by spreading (infiltrating) to other organs. ALL is most common in childhood with a peak incidence at 2-5 years of age, and another peak in old age.

"Acute" refers to the relatively short time course of the disease (being fatal in as little as a few weeks if left untreated) to differentiate it from the very different disease of chronic lymphocytic leukemia, which has a potential time course of many years. It is interchangeably referred to as lymphocytic or lymphoblastic. This refers to the cells that are involved, which if they were normal would be referred to as lymphocytes but are seen in this disease in a relatively immature (also termed "blast") state.

Four decades ago, the survival rate for ALL was zero. The survival rate has improved since then due to development of therapies such as chemotherapies, radiation, steroids, and bone marrow transplants. However, such therapies can have devastating side effects or, in the case of bone marrow therapy, not be possible due to lack of a suitable donor. The earlier ALL is detected, the more effective the treatment. There is a need in the art for methods of detecting ALL at earlier stages and for therapies that are non-toxic, effective, and don't require donor tissue.

SUMMARY OF THE INVENTION

The instant disclosure relates to the finding that lincRNA expression is associated with particular cytogenetic abnormalities and is related to disease pathogenesis of certain cancers. Long intergenic non-coding RNAs (lincRNAs) have been found to play a role in gene regulation, but their expression has not been described in B acute lymphoblastic leukemia (B-ALL). It was found that certain lincRNAs correlated with poor survival and diminished response to prednisone treatment in patients. For example, in B-ALL cell lines, the lincRNA, BALIR-2 (B-ALL associated long intergenic RNA-2), was downregulated in response to prednisone treatment. When BALIR-2 was knocked down, an increase in apoptotic activity and a reduction in proliferation was observed. These data, taken together, suggest that BALIR-2 plays a functional role in the pathogenesis of B-ALL.

Methods and compositions are provided involving lincRNAs, particularly those differentially expressed in B-ALL. The claims set forth herein provide a description of the invention.

In some embodiments, a nucleic acid comprises all or part of any of SEQ ID NOs:1-90, which provide sequences as DNA. It is specifically contemplated that nucleic acids may be RNA using any of the sequences in SEQ ID NOs:1-90 except that a uracil (U) is substituted for a thymine (T). It is noted that the human BALIR-2 sequence provided in SEQ ID NO:38 is a cDNA sequence for BALIR-2 and that as an RNA molecule, BALIR-2 has uracil instead of thymine in SEQ ID NO:38.

Aspects of the disclosure related to isolated nucleic acid molecules and fragments thereof that comprise a sequence that is at least 70% identical or complementary to a region of at least 15 contiguous nucleotides in SEQ ID NO:38 (BALIR-2), SEQ ID NO:1 (BALIR-1), SEQ ID NO:2 (BALIR-1), SEQ ID NO:3 (BALIR-2), SEQ ID NO:4 (BALIR-2), SEQ ID NO:5 (BALIR-6), SEQ ID NO:6 (BALIR-6), SEQ ID NO:7 (BALIR-11), SEQ ID NO:8 (BALIR-11), SEQ ID NO:84 (mouse Balir-2), or SEQ ID NOs: 85-90. Further aspects relate to an isolated nucleic acid molecule that comprises a sequence that is at least 60% identical or complementary to any of SEQ ID NO:38, SEQ ID NOs:85-90, SEQ ID NOs: 1-8, SEQ ID NOs:22-28, SEQ ID NOs:76-77, SEQ ID NOs:39-47, SEQ ID NO:79, SEQ ID NO:81, and SEQ ID NO:83, along the length of the SEQ ID NO. In the BALIR sequences disclosed in Table 1, an "m" preceding the name of the sequence refers to a mouse sequence. Other BALIR sequences refer to the human sequence.

Yet further aspects relate to expression vectors, conjugates, and compositions comprising a nucleic acid of Table 1.

In Table 1, the siRNA sequences contain a targeting sequence and a miR-155 framework. The targeting sequence in the siRNA that is complementary to BALIR-2 is underlined and is the second SEQ ID NO. The first SEQ ID NO for a particular siRNA is the sequence for the entire molecule. For example, with "BALIR2-siRNA1," SEQ ID NO:29 is the entire sequence shown, while SEQ ID NO:39 is the targeting sequence. Moreover, BALIR2 siRNA-conserved refers to a targeting sequence that is complementary to a sequence conserved in human and mouse BALIR-2.

Described herein are also methods of making the nucleic acids of Table 1 and methods using the nucleic acids of Table 1. Provided is a method for evaluating blood or bone marrow cells from a patient with leukemia or suspected of having leukemia comprising measuring expression in blood or bone marrow cells of at least one B-lymphoblastic leukemia lincRNA (BALIR) molecule and comparing the expression to a control or reference level(s) of expression in blood or bone marrow cells.

The phrase "comparing the expression to a control or reference level(s) of expression" refers to the use of a level of expression that can be used for comparison, particularly a level that represents a level in a normal or noncancerous cell or a cancer cell of a particular subtype that is consistent with the differential expression observed herein.

The phrase "relative to the control or reference level" in the context of expression refers to the use of a level of expression that can be used for comparison, particularly a level that represents a level in a normal or noncancerous cell or a cancer cell of a particular subtype that is consistent with the differential expression observed herein.

A further aspect relates to a method of treating a patient determined to have or suspected of having B-lymphoblastic leukemia comprising administering prednisone to the patient after the patient is determined not to have an elevated level of BALIR-2 expression compared to the level in a control or reference sample, wherein the sample includes non-leukemic B-cells.

Another method relates to a method for increasing apoptosis in an apoptotic-resistant cell comprising administering to the cell a composition comprising a BALIR inhibitor. A further method refers to a method for treating a lymphoblastic leukemia in a subject in need thereof comprising administering a BALIR inhibitor to the subject.

The term "BALIR inhibitor" refers to a nucleic acid, small molecule, or polypeptide that may either inhibit the expression of the BALIR lincRNA or inhibit the mechanism of action of the BALIR lincRNA by, for example, direct binding. Another example of a BALIR inhibitor is one that inhibits the mechanism of action of BALIR lincRNA indirectly, by, for example, inducing an inhibitor of BALIR or suppressing an activator of BALIR.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention. It is particularly contemplated that any embodiment specifically recited may also be excluded in other aspects.

A "subject," "individual" or "patient" is used interchangeably herein and refers to a vertebrate, for example a primate, a mammal or a human. Mammals include, but are not limited to equines, canines, bovines, ovines, murines, rats, simians, humans, farm animals, sport animals and pets.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8A-8G—Two step cluster analysis identified two clusters of expressors. (A-D) Histogram showing distribution of BALIR-1 (A) BALIR-2 (B), BALIR-6 (C) and BALIR-11 (D) expression. Two step clustering analysis identified two clusters (high and low expression) of data within the distribution. Bars indicate the frequency of cases within each bin (n=90) (E-F): Kaplan Meier survival analysis for the high and low expression groups of BALIR-1 (E, overall survival (OS) high=100%, OS low=88.5%), BALIR-6 (F, OS high=66.7%, OS low=89.7%) and BALIR-11 (G, OS high=100%, OS low=88.4%).

FIGS. 12A-12J—BALIR-2 shows a functional role in human B-ALL cell lines. (A) Map showing the position of BALIR-2 in the genome, including the locations of neighboring genes (exons shown in green), corresponding annotated mRNA, RACE product confirmation, probe set on microarray, qPCR primers and siRNAs targeting the lincRNA. (B) The Vertebrate PhastCons plot from the UCSC whole-genome alignments to mouse and zebrafish shows conserved regions within the terminal exon, including a region highly conserved among 91 vertebrates. (C) siRNA-mediated knockdown of BALIR-2 in RS4;11 cell line, shown by RT-qPCR (normalized to Actin). (D) Reduction of cell proliferation in RS;411 cells stably transduced with siRNA1 against BALIR-2, measured by MTS assay. (E-H) Increased apoptosis in RS4;11 cells stably transduced with siRNA2 against BALIR-2, measured by caspase-3 activity. Treatment groups include no treatment (E), 100 mg/mL doxorubicin (F), DMSO control (G) and 250 mg/mL prednisolone in DMSO (H). (I-J) Expression of genes immediately adjacent to BALIR-2, CDK6 and SAMD9, respectively, following siRNA mediated knockdown of the lincRNA. All experiments were repeated at least three times and similar results were obtained.

DESCRIPTION OF ILLUSTRATIVE EMBODIMENTS

Figures 1A, 1B, 1C, 1D, 1E, 1F:
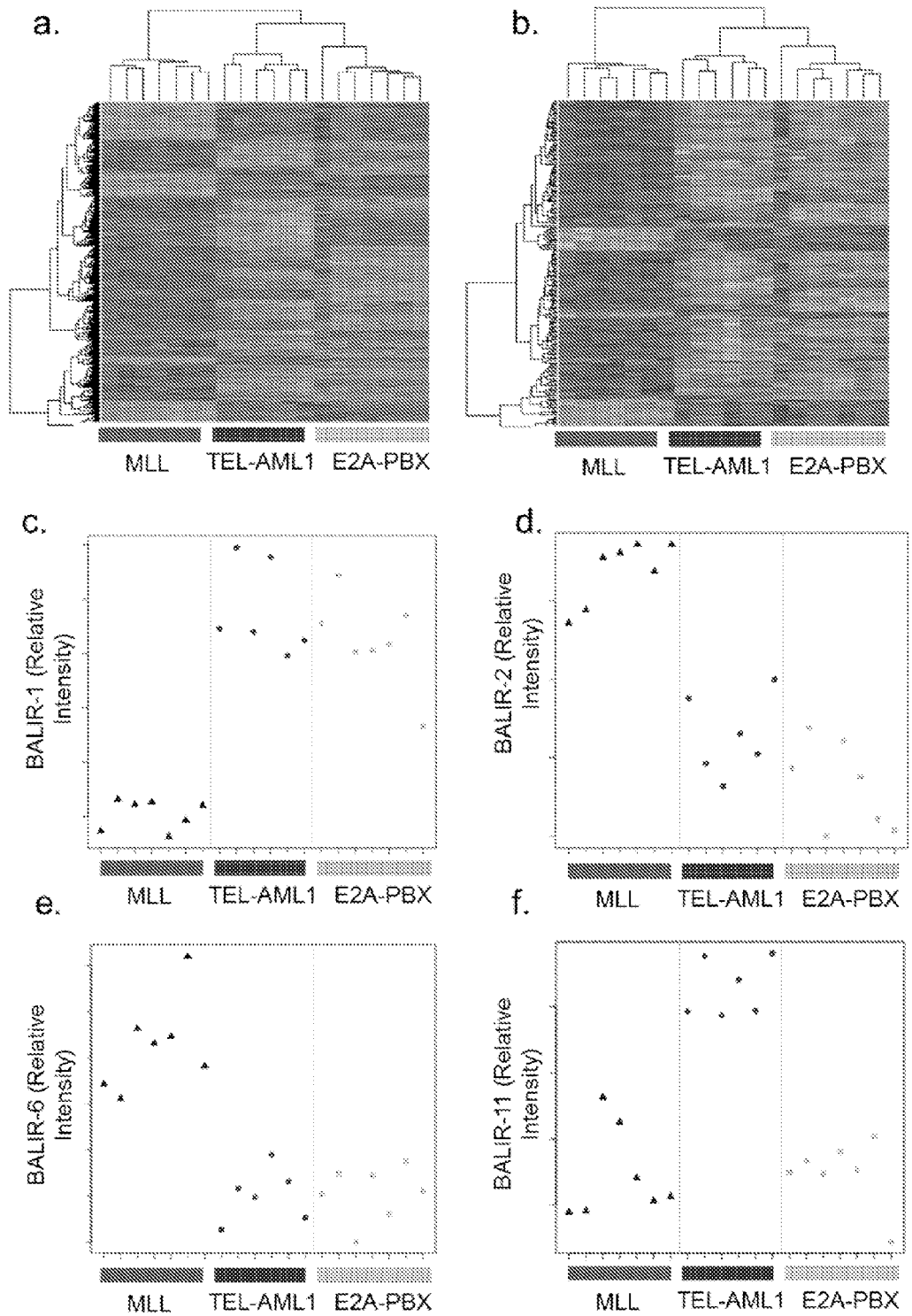
FIGS. 1A-1F—LincRNA expression segregates with ALL cytogenic subtypes. (A) Hierarchical clustering of significantly regulated protein-coding gene expression data in 20 B-ALL samples. Samples with similar patterns of expression of the genes clustered together, as indicated by the dendrogram. (B) Hierarchical clustering of lincRNAs that were differentially expressed with an adjusted p-value of less than 0.01 showed distinct separation into three subsets of B-ALL. Genes that are relatively upregulated appear in green, and those that are relatively downregulated appear in red (C-F) Plots of normalized intensity ratios for the three cytogenetic subtypes of ALL when looking at expression of BALIR-1, BALIR-2, BALIR-6, and BALIR-11, respectively. TEL-AML1 translocated n=6, E2A-PBX translocated n=7 and MLL rearranged n=7. (the class label for heatmap is not aligned)

Long intergenic non-coding RNAs (lincRNAs) have been found to play a role in gene regulation with dysregulated expression in various cancers, but their expression has not been described in B acute lymphoblastic leukemia (B-ALL).

The advent of high-throughput techniques to study gene expression has led to the recognition that almost 30-50% of the human genome is transcribed (Kapranov, 2007; Cheng, 2005, Kapranov, 2002). Of this, only about 3% (or 1% of the total genome) consists of genes that encode proteins. Once thought to be transcriptional "garbage", it is now clear that a significant subset of non-coding RNAs represent functional molecules that regulate cellular processes (Caminci, 2005). Perhaps the clearest example of functional non-coding RNA is microRNA (miRNA). These small non-coding RNAs have emerged as significant modulators of gene expression, and regulate diverse physiologic processes including hematopoietic development and immune cell activation. miRNAs are dysregulated in pathologic conditions of the hematopoietic and immune systems, including autoimmunity and cancer (reviewed in Baltimore, 2008). In oncogenesis, individual miRNAs have been found to act as either tumor suppressor genes or oncogenes, based on our work and that of others (O'Connell, 2008; Costinean, 2006, Klein, 2010).

A new addition to the repertoire of non-coding RNA is so-called long intergenic non-coding RNA (lincRNA) (Guttman, 2009). These RNAs, as the name implies, are found in intergenic regions, and approximately 2,000 have been detected in the transcriptome by a combination of sophisticated high-throughput technologies. Powerful computational methods confirm the absence of an open reading frame in these lincRNAs (Guttman, 2009). Although several other classes of non-coding RNA species are being described, lincRNAs are unique in that there are epigenetic marks in their promoter region (H3K4me3) and along the body of the transcribed region (H3K36me3), confirming their status as unique gene structures (Affymetrix, 2009). LincRNAs have now been described as regulating various molecular processes within the cell, including transcriptional repression, repression of microRNA activity by competitive binding, splicing regulation and translational repression (Rinn, 2007; Huarte, 2010; Cesana, 2011; Tripathi, 2010; Carrieri, 2012; Gong, 2011). In addition, lincRNAs have been implicated in physiological processes, such as in the growth and maintenance of embryonic stem cells, and in regulating erythroid development during hematopoiesis (Ng, 2012; Dinger, 2008; Sheik Mohamed, 2010; Guttman, 2011; Hu, 2011; Paralkar, 2011).

Prior studies have examined lincRNA expression in cell lines of various types as well as in a select few epithelial malignancies (Presner, 2011). However, no profile of lincRNA expression has been described in the hematopoietic malignancies. Given that many hematopoietic malignancies result from mutations that cause dysregulation of gene expression, we reasoned that lincRNAs may play a role in pathogenesis of these malignancies. In particular, B-lymphoblastic leukemia (B-ALL), which is a malignancy of precursor B-cells, has previously been shown to harbor mutations and translocations resulting in dysregulated gene expression (Nordlund, 2012; Borowitz, 2008). To date, there has not been a comprehensive description of lincRNA expression in B-ALL. Hence, Applicants undertook a study examining lincRNA expression in B-ALL, examining correlations with clinicopathologic parameters, and querying the functional consequences of lincRNA expression.

Here, Applicants present the first study of lincRNA expression in pediatric B-lymphoblastic leukemia (B-ALL) and find that overall lincRNA expression corresponds with specific cytogenetic abnormalities and that a subset of lincRNAs can correctly predict the cytogenetic subtype of B-ALL amongst the three most common abnormalities. However, it was also found that in a large set of unselected cases that includes those without a cytogenetically detected abnormality, lincRNA expression is heterogeneous, and the expression of one lincRNA, BALIR-2, is correlated with a poor patient response to prednisone and worse overall survival. Interestingly, BALIR-2 was repressed when human B-ALL cell lines were treated with prednisolone (the active metabolite of prednisone), suggesting that it may have a cellular role in the response of B-ALL cells. Applicants then developed knockdown vectors to target BALIR-2 and found that knockdown causes a modest increase in apoptosis of the B-ALL cell lines both at steady state and when coupled with treatment with either doxorubicin or prednisolone, which are part of most chemotherapeutic regimens against B-ALL. These data represent the first insights into long non-coding RNA expression in B-ALL and reveal that they may play a role in pathogenesis, disease severity, and measurement/alteration of their levels may be useful in prognosis and/or treatment of this disease, respectively.

I. Nucleic Acids

Embodiments concern polynucleotides or nucleic acid molecules relating to BALIR sequences in diagnostic, therapeutic and preventative applications. The terms "polynucleotide", "oligonucleotide" and "nucleic acid" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, lincRNA, shRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

In certain embodiments, nucleic acid molecules serve as an inhibitor to a BALIR RNA for the prevention or treatment of cancer, particularly B-lymphoblastic leukemia. In certain embodiments the nucleic acid of the invention is has a certain level of sequence identity to a nucleic acid of Table 1 or is one that hybridizes under stringent or highly stringent hybridization conditions to a nucleic acid of Table 1.

"Hybridization" refers to a reaction in which one or more polynucleotides react to form a hybridization complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 91%, 92%, 93%, 94%, 95%, 96%, 97%, 98% or 99%—or any range derivable therein) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology.

Embodiments of the disclosure include nucleic acids that are at least 60%, 65%, 70%, 75%, 80%, 85%, 90%, 91%, 92%, 93%, 94%, 95%, 96%, 97%, 98%, 99% or 100% identical or complementary to a region of at least or at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, or 470 contiguous nucleotides of a sequence of Table 1. Particular embodiments include a sequence of a BALIR lincRNA such as SEQ ID NOs:1-8, 48-49, 38-47, 79, 81, 83, and 84-90.

In further embodiments, the isolated nucleic acid comprises a sequence that is at least 60%, 65%, 70%, 75%, 80%, 85%, 90%, 91%, 92%, 93%, 94%, 95%, 96%, 97%, 98%, 99% or 100% identical or complementary (or any range derivable therein) to any of SEQ ID NOs: 1-90, along the length of the SEQ ID NO.

Specific embodiments include nucleic acids that are 1, 10, 15, 20, 25, 30, 35, 40, 45, 50, 55, 60, 65, 70, 75, 80, 85, 90, 95, 100, 110, 115, 120, 130, 135, 140, 145, 150, 155, 160, 165, 170, 175, 180, 185, 190, 195, 200, 205, 210, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, or 465 nucleotides fewer than the full length sequence of a sequence of Table 1 (or any range derivable therein). A further specific embodiment refers to SEQ ID NO: 38 or SEQ ID NOs: 84-90.

Also included in the disclosure is a nucleic acid molecule as described herein wherein the nucleic acid molecule is either 1) not composed entirely of ribonucleotides or 2) does not consist of SEQ ID NO: 38 or SEQ ID NOs: 84-90.

A further embodiment includes a nucleic acid molecule as described herein, wherein the region comprises SEQ ID NO: 38 or SEQ ID NOs: 84-90 and contiguous nucleotides from at least two exons of a BALIR gene.

A further embodiment includes a nucleic acid molecule as described herein, wherein the nucleic acid molecule comprises deoxyribonucleotides or is cDNA. Nucleic acids of the disclosure may be synthetic or recombinant.

A further embodiment includes a nucleic acid molecule as described herein, wherein the nucleic acid molecule is from 5, 10, 20, 30, 40, 50, 60, 70, 80, 90, 100 to 15, 20, 30, 40, 50, 60, 70, 80, 90, 100, 110, 120, 125, 130, 135, 140, 145, 150, 155, 160, 165, 170, 175, 180, 185, 190, 195, 200, 225, 250, 275, 300, 350, 400, or 450 nucleotides in length (or any range derivable therein) and is at least 60, 70, 80, 85, 90, 95, 96, 97, 98, or 99% complementary (or any range derivable therein) to any of SEQ ID NO:38 or SEQ ID NOs:84-90 along the length of the nucleic acid molecule. A specific embodiment includes a nucleic acid molecule as described herein, wherein the nucleic acid molecule is 12 to 100 nucleotides in length and is at least 90% complementary to any of SEQ ID NO:38 or SEQ ID NOs:84-90 along the length of the nucleic acid molecule.

Sequences that have or have at least or at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any range derivable therein, of nucleic acids that are identical or complementary to a nucleic acid sequence of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, or 480 contiguous bases (or any range derivable therein) of SEQ ID NOs:1-90 are contemplated as embodiments.

Also part of the disclosure are biologically equivalent polynucleotides of the polynucleotides disclosed in Table 1. Biologically equivalent polynucleotides are those having the specified percent homology and the same or similar biological activity.

Nucleic acids or polynucleotides may be DNA or RNA, and they may be recombinantly produced or synthetically produced. These polynucleotides or nucleic acid molecules may be isolatable and/or purifiable from cells or they may be synthetically produced. In some embodiments, a nucleic acid of the disclosure is an inhibitor of BALIR, such as an siRNA that reduces the level of BALIR expression.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 2001; Ausubel, 1996). Alternatively, cDNAs may be advantageous because it represents coding regions of a polypeptide and eliminates introns and other regulatory regions. In certain embodiments, nucleic acids are complementary or identical to human cDNA encoding sequences, such as a human BALIR sequence (SEQ ID NO:38).

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells.

The nucleic acid molecules can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A. Inhibiting Nucleic Acid Molecules

Also provided are antisense nucleic acid molecules. The term "antisense" refers to a nucleic acid complementary to the coding region of the DNA. The term "antisense" as used herein may also mean a nucleic acid that is complementary to a BALIR lincRNA such as the BALIR lincRNAs disclosed as SEQ ID NO:38 and SEQ ID NOs:84-90 and reduces expression of the BALIR lincRNA. Specific embodiments include an antisense nucleic acid molecule targeting BALIR 1, BALIR-2, BALIR-6 or BALIR-11 comprising the isolated nucleic acid molecule as described herein, wherein the isolated nucleic acid molecule has a sequence that is complementary to BALIR 1, BALIR-2, BALIR-6 or BALIR-11. A particular embodiment of the disclosure includes an antisense molecule comprising a nucleic acid having a sequence corresponding to a sequence of SEQ ID NOs:39-47, 79, 81, or 83. The antisense molecule may include a backbone of, for example, a micro RNA. In certain embodiments, the antisense molecule includes a miR-155 backbone and comprises the sequence of SEQ ID NOs:29-37, 78, 80, or 82.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription, non-coding RNA transcription, translation or both within a host cell, either in vitro or in vivo, such as within a host animal, including a human subject. Antisense constructs may be designed to bind to the promoter and other control regions, exons, introns or even exon-intron boundaries of a gene.

Complementary or antisense nucleic acid sequences may also refer to sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

In certain embodiments, the nucleic acid encodes an interfering RNA or siRNA. RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery, 1999; Montgomery et al., 1998; Sharp and Zamore, 2000; Tabara et al., 1999). Activation of these mechanisms targets mature, dsRNA-complementary mRNA for destruction. Advantages of RNAi include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs are designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; or through an in vitro system derived from S2 cells. Chemical synthesis proceeds by making two single stranded RNA-oligomers followed by the annealing of the two single stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

In some embodiments, there is an siRNA that is capable of triggering RNA interference. siRNA are dsRNA molecules that are 100 bases or fewer in length (or have 100 basepairs or fewer in its complementarity region). In some cases, it has a 2 nucleotide 3' overhang and a 5' phosphate. It will be understood that dsRNA or siRNA can effect at least a 20, 30, 40, 50, 60, 70, 80, 90 percent or more reduction of expression of a targeted RNA in a cell. dsRNA (the term "dsRNA" will be understood to include "siRNA") is distinct and distinguishable from ribozyme molecules by virtue of the ability to trigger RNAi. Structurally, dsRNA molecules for RNAi differ from ribozyme molecules in that dsRNA has at least one region of complementarity within the RNA molecule. The complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, to sequences (or their complements) disclosed herein. In some embodiments, the sequence is SEQ ID NO:38 or SEQ ID NOs:84-90.

In some embodiments, long dsRNA are employed in which "long" refers to dsRNA that are 1000 bases or longer (or 1000 basepairs or longer in complementarity region). The term "dsRNA" includes "long dsRNA" and "intermediate dsRNA" unless otherwise indicated. In some embodiments, dsRNA can exclude the use of siRNA, long dsRNA, and/or "intermediate" dsRNA (lengths of 100 to 1000 bases or basepairs in complementarity region). It is contemplated that a dsRNA may be a molecule comprising two separate RNA strands in which one strand has at least one region complementary to a region on the other strand. Alternatively, a dsRNA includes a molecule that is single stranded yet has at least one complementarity region as described above (see Sui et al., 2002 and Brummelkamp et al., 2002 in which a single strand with a hairpin loop is used as a dsRNA for RNAi). For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

The single RNA strand or two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more (including the full-length of a particular's gene's mRNA without the poly-A tail) bases or basepairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer. In some cases, a dsRNA may be processed in the cell into siRNA.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

PCT publications WO 99/32619 and WO 01/68836 suggest that RNA for use in siRNA may be chemically or enzymatically synthesized. Both of these texts are incorporated herein in their entirety by reference. The contemplated constructs provide templates that produce RNAs that contain nucleotide sequences identical to a portion of the target gene. Typically the length of identical sequences provided is at least 25 bases, and may be as many as 400 or more bases in length. Longer dsRNAs may be digested to 21-25mer lengths with endogenous nuclease complex that converts long dsRNAs to siRNAs in vivo. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. U.S. Pat. No. 5,795,715 reports the simultaneous transcription of two complementary DNA sequence strands in a single reaction mixture, wherein the two transcripts are immediately hybridized.

A nucleic acid molecule may be used to regulate the expression of one or more cellular proteins or the expression of one or more RNAs. For example, the nucleic acid molecule of this disclosure may function to reduce the expression of one or more lincRNAs such as BALIR. In an embodiment, the nucleic acid molecules comprise RNA and introduction of the RNA into a cell results in reduced expression of at least one RNA transcript. The present disclosure provides for such RNA molecules, the DNA molecules encoding such RNA molecules, the polypeptide encoded by such nucleic acid molecules, antibodies raised to said polypeptides; or combinations thereof. The RNA molecules of this disclosure can be used in a variety of forms; nonlimiting examples of which include antisense RNAi and shRNA.

The disclosed methodologies utilize the RNA interference (RNAi) mechanism to reduce the expression of one or more RNA transcripts. The term "RNA interference or silencing" is broadly defined to include all posttranscriptional and transcriptional mechanisms of RNA mediated inhibition of gene expression, such as those described in P. D. Zamore Science 296, 1265 (2002) which is incorporated by reference herein in its entirety. The discussion that follows focuses on the proposed mechanism of RNA interference mediated by short interfering RNA as is presently known, and is not meant to be limiting and is not an admission of prior art.

RNAi is a conserved biological response that is present in many, if not most, eukaryotic organisms. RNAi results in transcript silencing that is both systemic and heritable, permitting the consequences of altering gene expression to be examined throughout the development and life of an animal.

In the RNAi process, long double-stranded RNA molecules (dsRNA) can induce sequence-specific silencing of gene expression in primitive and multicellular organisms. These long dsRNAs are processed by a ribonuclease called Dicer into 21 to 23 nucleotide (nt) guide RNA duplexes termed short interfering RNA (siRNA). The siRNA is subsequently used by an RNA-induced silencing complex (RISC), a protein-RNA effector nuclease complex that uses siRNA as a template to recognize and cleave RNA targets with similar nucleotide sequences. The composition of RISC is not completely defined, but includes argonaute family proteins. The RISC unwinds siRNAs and associates stably with the (antisense) strand that is complementary to the target mRNA. Depending on the degree of homology between a siRNA and its target mRNA, siRNA-RISC complexes inhibit gene function by two distinct pathways. Most siRNAs pair imperfectly with their targets and silence gene expression by translational repression. This RNAi mechanism appears to operate most efficiently when multiple siRNA-binding sites are present in the 3'-untranslated region of the target mRNAs. In some other cases, siRNAs exhibit perfect sequence identity with the target mRNA and inhibit gene function by triggering mRNA degradation. The reduction in transcript level results in lowered levels of the target protein, resulting in phenotypic changes.

The compositions of this disclosure comprise one or more nucleic acid molecules. In an embodiment, the nucleic acid molecule comprises a double stranded ribonucleic acid (dsRNA) molecule that inhibits the expression of a target gene wherein the dsRNA molecule comprises two strands of nucleotides wherein the first strand is substantially identical to the nucleotide sequence of SEQ ID NOs:39-47, 79, 81, or 83 and wherein the second strand is substantially complementary to the first strand. Herein substantially identical refers to greater than about 50% homology while substantially complementary refers to a complementarity sufficient to permit the annealing of the second strand to the first strand under biological conditions such as within the cytoplasm of a eukaryotic cell.

In an embodiment, the first strand is greater than about 55% identical, alternatively greater than about 60%, 65%, 70%, 75%, 80%, 90%, 95% identical to a complementary region of SEQ ID NO:38 or SEQ ID NOs:84-90. The first strand may be of sufficient length such that it is processed by Dicer to produce an siRNA. Either strand may serve as a substrate for Dicer.

The length of each strand generally is from about 19 to about 25 nt in length (e.g., 19, 20, 21, 22, 23, 24, or 25 nucleotides). In some embodiments, the length of each strand is from about 19 to about 28 nucleotides in length. In one embodiment, the length of the sequence in the first strand is identical to the length of the sequence in the second strand and the dsRNA formed is blunt ended. In an alternative embodiment, the ends of the dsRNA formed has overhangs. In one embodiment, the length of each strand is greater than 23 nt.

In an embodiment, an dsRNA for use in reducing the level of expression of a lincRNA such as BALIR or LINC00958 comprises a first strand which includes the RNA equivalent of the sequence and of SEQ ID NOs: 39-47, 79, 81, or 83. In an embodiment, the complementary first and second strands of the dsRNA molecule are the "stem" of a hairpin structure. The two dsRNA strands can be joined by a binding moiety, which can form the "loop" in the hairpin structure of shRNA. In an embodiment the binding moiety comprises a polynucleotide linker which can vary in length. In some embodiments, the binding moiety can be 5, 6, 7, 8, 9, 10, 11, 12 or 13 nucleotides in length, alternatively the binding moiety is 9 nucleotides in length.

B. Preparation of Nucleic Acids

The disclosure provides for methods of making the nucleic acids, including the antisense nucleic acids comprising synthesizing the nucleic acid molecule using synthetic nucleotides. A further method provides for making the nucleic acid or antisense nucleic acid molecule comprising incubating an expression vector comprising the nucleic acid of the disclosure under conditions to provide expression of the nucleic acid molecule.

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotides may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

Nucleic acid molecules (e.g., dsRNA, shRNA, and DNAs) as described herein can be obtained using techniques known to one of ordinary skill in the art such as for example, recombinant nucleic acid technology; chemical synthesis, either as a single nucleic acid molecule or as a series of oligonucleotides; mutagenesis using common molecular cloning techniques (e.g., site-directed mutagenesis); and the polymerase chain reaction (PCR). General PCR techniques are described, for example in PCR Primer: A Laboratory Manual, Dieffenbach & Dveksler, Eds., Cold Spring Harbor Laboratory Press, 1995 which is incorporated by reference herein in its entirety. Possible mutations include, without limitation, deletions, insertions, substitutions, and combinations thereof. Additionally, suitable molecular biology techniques may be employed for isolation of these molecules such as for example and without limitation restriction enzyme digestion and ligation.

As is known in the art, a nucleoside is a base-sugar combination. The base (or nucleobase) portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the unmodified oligonucleotide structure, the phosphate groups are commonly referred to as forming the internucleoside linkages of the oligonucleotide. The unmodified internucleoside linkage of RNA and DNA is a 3' to 5' phosphodiester linkage.

C. Nucleic Acid Modifications

In the context of this disclosure, the term "unmodified oligonucleotide" refers generally to an oligomer or polymer of ribonucleic acid (RNA) or deoxyribonucleic acid (DNA). In some embodiments a nucleic acid molecule is an unmodified oligonucleotide. This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases. The term "oligonucleotide" can be used to refer to unmodified oligonucleotides or oligonucleotide analogs.

Specific examples of nucleic acid molecules include nucleic acid molecules containing modified, i.e., non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases. In a specific embodiment, the modification comprises a methyl group.

Nucleic acid molecules can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Modifications to nucleic acid molecules can include modifications wherein one or both terminal nucleotides is modified.

One suitable phosphorus-containing modified internucleoside linkage is the phosphorothioate internucleoside linkage. A number of other modified oligonucleotide backbones (internucleoside linkages) are known in the art and may be useful in the context of this embodiment.

Representative U.S. patents that teach the preparation of phosphorus-containing internucleoside linkages include, but are not limited to, U.S. Pat. Nos. 3,687,808; 4,469,863; 4,476,301; 5,023,243, 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 5,625,050, 5,489,677, and 5,602,240 each of which is herein incorporated by reference.

Modified oligonucleoside backbones (internucleoside linkages) that do not include a phosphorus atom therein have internucleoside linkages that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having amide backbones; and others, including those having mixed N, O, S and CH2 component parts.

Representative U.S. patents that teach the preparation of the above non-phosphorous-containing oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Oligomeric compounds can also include oligonucleotide mimetics. The term mimetic as it is applied to oligonucleotides is intended to include oligomeric compounds wherein only the furanose ring or both the furanose ring and the internucleoside linkage are replaced with novel groups, replacement of only the furanose ring with for example a morpholino ring, is also referred to in the art as being a sugar surrogate. The heterocyclic base moiety or a modified heterocyclic base moiety is maintained for hybridization with an appropriate target nucleic acid.

Oligonucleotide mimetics can include oligomeric compounds such as peptide nucleic acids (PNA) and cyclohexenyl nucleic acids (known as CeNA, see Wang et al., J. Am. Chem. Soc., 2000, 122, 8595-8602) Representative U.S. patents that teach the preparation of oligonucleotide mimetics include, but are not limited to, U.S. Pat. Nos. 5,539,082; 5,714,331; and 5,719,262, each of which is herein incorporated by reference. Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Another oligonucleotide mimetic has been reported wherein the furanosyl ring has been replaced by a cyclobutyl moiety.

Nucleic acid molecules can also contain one or more modified or substituted sugar moieties. The base moieties are maintained for hybridization with an appropriate nucleic acid target compound. Sugar modifications can impart nuclease stability, binding affinity or some other beneficial biological property to the oligomeric compounds.

Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. A large number of sugar modifications are known in the art, sugars modified at the 2' position and those which have a bridge between any 2 atoms of the sugar (such that the sugar is bicyclic) are particularly useful in this embodiment. Examples of sugar modifications useful in this embodiment include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted C1 to C10 alkyl or C2 to C10 alkenyl and alkynyl. Particularly suitable are: 2-methoxyethoxy (also known as 2'-O-methoxyethyl, 2'-MOE, or 2'-OCH2CH2OCH3), 2'-O-methyl (2'-O—CH3), 2'-fluoro (2'-F), or bicyclic sugar modified nucleosides having a bridging group connecting the 4' carbon atom to the 2' carbon atom wherein example bridge groups include —CH2-O—, —(CH2)2-O— or —CH2-N(R3)-O wherein R3 is H or C1-C12 alkyl.

One modification that imparts increased nuclease resistance and a very high binding affinity to nucleotides is the 2'-MOE side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

2'-Sugar substituent groups may be in the arabino (up) position or ribo (down) position. One 2'-arabino modification is 2'-F. Similar modifications can also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative sugar substituents groups are disclosed in U.S. Pat. No. 6,172,209 entitled "Capped 2'-Oxyethoxy Oligonucleotides," hereby incorporated by reference in its entirety.

Representative cyclic sugar substituent groups are disclosed in U.S. Pat. No. 6,271,358 entitled "RNA Targeted 2'-Oligomeric compounds that are Conformationally Preorganized," hereby incorporated by reference in its entirety.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Nucleic acid molecules can also contain one or more nucleobase (often referred to in the art simply as "base") modifications or substitutions which are structurally distinguishable from, yet functionally interchangeable with, naturally occurring or synthetic unmodified nucleobases. Such nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds. These include 5-substituted pyrimidines, 6-azapyrimidines and N-2, N-6 and O-6 substituted purines, including 2 aminopropyladenine, 5-propynyluracil and 5-propynylcytosine.

Additional modifications to nucleic acid molecules are disclosed in U.S. Patent Publication 2009/0221685, which is hereby incorporated by reference. Also disclosed herein are additional suitable conjugates to the nucleic acid molecules.

II. Expression Systems

Also provided by the disclosure are expression vectors encoding a nucleic acid molecule as described herein. In specific embodiments, the expression vector is a viral vector or bacterial vector. In a further embodiment, the expression vector is a mammalian expression vector.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome (such as an adenoviral vector, a lentiviral vector, etc.). A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors").

In aspects where the vector is a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA;

however, once the virus infects a cell, the RNA is reverse-transcribed into the DNA form which integrates into the genomic DNA of the infected cell. The integrated DNA form is called a provirus. As used herein, retroviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

In aspects where the vector is a a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

The nucleic acid molecules disclosed herein may be introduced to a cell directly using techniques such as for example encapsulation in a nanoparticle or a liposome; electroporation; calcium phosphate precipitation and the like. In some embodiments, one or more nucleic acid molecules may be introduced to a cell as an element of a vector and thus comprise a DNA vector-based siRNA.

Vectors, including expression vectors, suitable for use in the present disclosure are commercially available and/or produced by recombinant DNA technology methods routine in the art. A vector containing a nucleic acid of this disclosure may have elements necessary for expression operably linked to such a molecule, and further can include sequences such as those encoding a selectable marker (e.g., a sequence encoding antibiotic resistance). Vectors suitable for use in this disclosure can integrate into the cellular genome or exist extrachromosomally (e.g., an autonomous replicating plasmid with an origin of replication).

In an embodiment, the vector is an expression vector and comprises additional elements that are useful for the expression of the nucleic acid molecules of this disclosure. Elements useful for expression include nucleic acid sequences that direct and regulate expression of nucleic acid coding sequences. One example of an element useful for expression is a promoter sequence. Examples of promoters suitable for use include the mouse U6 RNA promoters, synthetic human H1 RNA promoters, SV40, CMV, RSV, RNA polymerase II, RNA polymerase III promoters, derivatives thereof, or combinations thereof. Elements useful for expression also can include ribosome-binding sites, introns, enhancer sequences, response elements, or inducible elements that modulate expression of a nucleic acid. Elements necessary for expression can be of bacterial, yeast, insect, mammalian, or viral origin and the vectors may contain a combination of elements from different origins. Elements necessary for expression are known to one of ordinary skill in the art and are described, for example, in Goeddel, 1990, Gene Expression Technology: Methods in Enzymology, 185, Academic Press, San Diego, Calif., the relevant portions of which are incorporated by reference herein. As used herein, operably linked means that a promoter and/or other regulatory element(s) are positioned in a vector relative to the shRNA in such a way as to direct or regulate expression of the molecule. A siRNA can be operably-linked to regulatory sequences in a sense or antisense orientation. In addition, expression can refer to the transcription of sense mRNA and may also refer to the production of protein. The disclosure further provides the nucleic acids of this invention operatively linked to a promoter of RNA transcription. In one embodiment, the promoter is a RNA pol III promoter such as U6 or H1.

Expression vectors containing these nucleic acids are useful to obtain host vector systems. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells as described above and constructed using well known methods. See Sambrook and Russell (2001), supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection. See Sambrook and Russell (2001), supra for this methodology.

Also provided are delivery vehicles suitable for delivery of a nucleic acid into cells (whether in vivo, ex vivo, or in vitro). A nucleic acid of the invention can be contained within a gene delivery vehicle, a cloning vector or an expression vector. These vectors (especially expression vectors) can in turn be manipulated to assume any of a number of forms which may, for example, facilitate delivery to and/or entry into a cell.

III. Diagnostic Assays, Methods, and Nucleic Acids

A. Diagnostic Assays and Methods

The disclosure also provides for methods for evaluating or screening a subject and/or biological sample for the expression of one or more lincRNAs described herein. One aspect relates to a method of evaluating blood or bone marrow cells from a patient with leukemia or suspected of having leukemia comprising measuring expression in blood or bone marrow cells of at least one B-lymphoblastic leukemia lincRNA (BALIR) molecule or LINC00958 and comparing the expression to a control or reference level(s) of expression in blood or bone marrow cells.

Biological samples are a sample of tissues taken from a patient diagnosed with a leukemia or one suspected of having a leukemia. Non-limiting examples of biological samples include blood, bone marrow, cerebrospinal fluid, lymph node, a biopsy (e.g. bone marrow or lymph node biopsy), and the like. A patient suspected of having leukemia may be one that exhibits symptoms of the disease such as low blood platelets, high white blood cell counts, frequent infections, ranging from infected tonsils, sores in the mouth, or diarrhea to life-threatening pneumonia or opportunistic infections, anemia, dyspnea, pallor, flu-like symptoms, nausea, unintentional weight loss, headaches, migraines, seizures, coma, and the like.

The term "blood" refers to blood which includes all components of blood circulating in a subject including, but not limited to, red blood cells, white blood cells, plasma, clotting factors, small proteins, platelets and/or cryoprecipitate. This is typically the type of blood which is donated when a human patent gives blood.

The expression level of the lincRNA can be measured by techniques known in the art and described herein. Typically, the nucleic acid mixture is isolated from a biological sample taken from the individual using standard techniques known in the art. The nucleic acid mixture may be comprised of genomic DNA, mRNA, or cDNA. Methods of determining expression levels are known in the art. For the purpose of illustration only, such methods can include determining the amount of a lincRNA using, for example, a method comprising one or more of in situ hybridization, PCR, real-time PCR, quantitative PCR, or microarray. The methods can be performed on at least one of a fixed tissue, a frozen tissue, a biopsy tissue, a resection tissue, a microdissected tissue, or combinations thereof.

Knowledge of the expression level of a lincRNA in an individual (i.e. genetic profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. The identity of the expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Detection of the lincRNAs described herein may allow for more effective therapeutic methods and may predict whether a patient will respond to certain drugs such as prednisone or prednisolone.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing disease such as leukemia.

Diagnostic procedures can also be performed in situ directly upon tissue sections (fixed and/or frozen) of primary tissue such as biopsies obtained from biopsies or resections, such that no nucleic acid purification is necessary. Nucleic acid reagents can be used as probes and/or primers for such in situ procedures (see, for example, Nuovo, G. J. (1992) PCR IN SITU HYBRIDIZATION: PROTOCOLS AND APPLICATIONS, RAVEN PRESS, NY).

In one embodiment, the method further comprises measuring expression of at least or at most 2, 3, or 4 additional BALIR molecules and comparing the expression to a control or reference level(s) of expression. The control or reference level of expression may be the level of expression of the BALIR molecule in non-leukemic blood or bone marrow cells.

In specific embodiments, the BALIR molecules are BALIR-1, BALIR-2, BALIR-6, BALIR-11, or LINC00958. In a further specific embodiment of the methods disclosed herein, the BALIR molecule is BALIR-1 and the measured expression level of BALIR-1 is determined to be increased compared to a control or reference level of BALIR-1. In a further specific embodiment, the BALIR molecule is BALIR-2 and the measured expression level of BALIR-2 is determined to be increased compared to a control or reference level of BALIR-2. In a further specific embodiment, the BALIR molecule is BALIR-6 and the measured expression level of BALIR-6 is determined to be increased compared to a control or reference level of BALIR-6. In a further specific embodiment, the BALIR molecule is BALIR-11 and the measured expression level of BALIR-11 is determined to be increased compared to a control or reference level of BALIR-11. In a further specific embodiment, the molecule evaluated is LINC00958, and the measured expression level of LINC00958 is determined to be increased compared to a control or reference level of LINC00958.

The expression level of the BALIR or LINC00958 molecule may be at least 1.5, 2, 3, 4, 5, 6, 7, 8, 9, 10, 20, 30, 50, 100, 200, or 1000 fold greater than the reference or control level of the BALIR or LINC00958 molecule.

In certain embodiments, measuring expression comprises one or more of generating complementary DNA (cDNA) of the BALIR molecule or any other lincRNA; an assay involving amplification and/or hybridization of a nucleic acid molecule; polymerase chain reaction (PCR); and real time quantitative polymerase chain reaction (RT-qPCR).

In certain embodiments, control or reference level is the level of expression in B-cells that are not leukemic. In further embodiments, the control or reference level is the level of expression in B-cells that are not B-ALL cells.

The control or reference level may be a pre-determined level obtained from the expression level of a non-leukemic cell (e.g. non-B-ALL cell). The reference level may also be a pre-determined level obtained from the average of a multitude of non-leukemic cells.

In the methods described herein, the method may further comprise determining that the level of expression of one or more measured lincRNAs in Table 1 is increased relative to the control or reference level of the lincRNA.

In another embodiment, the methods described herein further comprise generating a cDNA of the BALIR molecules or any other lincRNAs to be measured (e.g. LINC00958) and incubating the cDNA with primers under conditions to provide amplification of the BALIR molecules, any other lincRNA, and/or their complements.

In specific embodiments, the method further comprises obtaining the blood or bone marrow cells from the patient. In another specific embodiment, the method further comprises isolating nucleic acid molecules from the blood or bone marrow cells, wherein the nucleic acid molecules include lincRNA.

In certain embodiments, the expression is measured in situ.

In certain embodiments, the method further comprises reporting the level of expression measured. In another embodiment, the method comprises evaluating the blood or bone marrow cells. In a further embodiment, the method further comprises evaluating the cytology of blood or bone marrow cells.

In another embodiment, the method further comprises evaluating cells obtained from the patient's spinal fluid to identify leukemia cells. In a specific embodiment, the cells are obtained from a spinal tap or lumbar puncture.

In another embodiment, the method is practiced in a patient which has had one or more tumors evaluated for T-cell infiltration. In one embodiment, evaluating the cells comprised one or more of evaluating the size and number of leukemic cells, evaluating the type of lymphocytes are affected, or evaluating whether changes appear in the chromosomes of leukemic cells.

In further embodiments, the method includes one or more of identifying the patient's bone marrow cells as B-ALL cells; categorizing the cytogenetic subtype of B-ALL cells; identifying the patient as having subtype t(12;21) TEL-AML1 translocation; t(1;19) E2A-PBX translocation; or 11q23 (MLL) rearrangement; or categorizing the cells as early pre-B ALL, common ALL, pre-B-cell ALL, or mature B-cell ALL.

In certain embodiments, the method further comprises treating a patient with B-ALL with prednisone, prednisolone, chemotherapy, radiation, or a bone marrow or cord blood transplant, or a combination thereof. In one embodiment, the patient has previously been administered prednisone, chemotherapy, radiation, or a bone marrow or cord blood transplant, or a combination thereof, prior to measuring expression a BALIR molecule. In a further embodiment, the patient is one that has relapsed.

B. Diagnostic Nucleic Acids and Kits

The disclosure also provides for the use of the nucleic acids described herein as probes or primers in methods for detecting the expression level of lincRNAs of interest.

1. Nucleic Acids for Use in the Detection of BALIR Expression

In one aspect, the nucleic acid sequences of the lincRNA of interest, or portions thereof, can be the basis for probes or primers, e.g., in methods for determining expression level of the gene of interest identified in the experimental section below. Thus, they can be used in the methods of the disclosure to determine which therapy is most likely to treat an individual's cancer. Accordingly, certain embodiments of the disclosure are directed to probes comprising a nucleic acid described in Table 1.

This disclosure provides for a prognostic panel of genetic markers selected from, but not limited to the probes and/or primers listed in TABLE 1 to determine lincRNA expression as identified herein. Also included are probes or primers that comprise the sequence of SEQ ID NOs: 38 and 84 or a fragment thereof. The probes or primers can be attached or supported by a solid phase support such as, but not limited to a gene chip or microarray. The probes or primers can be detectably labeled. In one aspect, provided is a panel of probes and/or primers to determine the expression level of one or more BALIR RNA is a tumor cell, tumor tissue sample, or biological sample.

In one aspect, the panel contains the herein identified probes or primers as wells as other probes or primers. In an alternative aspect, the panel includes one or more of the above noted probes or primers and others. In a further aspect, the panel consist only of the above-noted probes or primers.

Primers or probes can be affixed to surfaces for use as "gene chips" or "microarray." Such gene chips or microarrays can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the disclosure also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarray" and similar technologies are know in the art. Examples of such include, but are not limited to LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarraying system that can dispense from 12 to 64 spots onto multiple glass slides (Intelligent Bio-Instruments); Molecular Biology Workstation and Nano-Chip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and Chip-Maker 3 (TeleChem International, Inc.); and GenoSensor (Vysis, Inc.) as identified and described in Heller (2002) Annu Rev. Biomed. Eng. 4:129-153. Examples of "Gene chips" or a "microarray" are also described in U.S. Patent Publ. Nos.: 2007/0111322, 2007/0099198, 2007/0084997, 2007/0059769 and 2007/0059765 and U.S. Pat. Nos. 7,138, 506, 7,070,740, and 6,989,267.

In one aspect, "gene chips" or "microarrays" containing probes or primers for the lincRNA of interest are provided alone or in combination with other probes and/or primers. A suitable sample is obtained from the patient extraction of genomic DNA, RNA, or any combination thereof and amplified if necessary. When a sample of RNA is used, the RNA may undergo the steps of amplification and/or reverse transcription to make a collection of cDNAs corresponding to the RNA sample. The DNA, cDNA or RNA sample is contacted to the gene chip or microarray panel under conditions suitable for hybridization of the lincRNA of interest to the probe(s) or primer(s) contained on the gene chip or microarray. The probes or primers may be detectably labeled thereby identifying expression of the lincRNA of interest. Alternatively, a chemical or biological reaction may be used to identify the probes or primers which hybridized with the DNA or RNA of the lincRNA of interest. The genetic profile of the patient is then determined with the aid of the aforementioned apparatus and methods.

2. Probes and Primers

Probes for use in the methods of the disclosure are nucleic acids that hybridize to the lincRNA of interest and which are not further extended. For example, a probe is a nucleic acid that hybridizes to the lincRNA of interest, and which by hybridization or degree of hybridization to the biological sample of a subject will be indicative of the identity of the expression levels of the gene of interest. Probes for use in the methods can be provided as isolated single stranded oligonucleotides or alternatively, as isolated double stranded oligonucleotides. In particular embodiments, the nucleic acid complementary or identical to an unprocessed or mature lincRNA is a DNA molecule that is single-stranded or comprises deoxyribonucleic acid residues and is single-stranded. In particular embodiments a nucleic acid comprises, is identical to, or is complementary to the sequence of a lincRNA but is not natural, either because it The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand. It is generally appreciated that conditions can be rendered more stringent by the addition of increasing amounts of formamide. For example, under highly stringent conditions, hybridization to filter-bound DNA may be carried out in 0.5 M NaHPO$_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of a lincRNA of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the disclosure will hybridize selectively to nucleotide sequences located about 100 to about 1000 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

The probe or primer may further comprises a label attached thereto, which, e.g., is capable of being detected, e.g. the label group is selected from amongst radioisotopes, fluorescent compounds, enzymes, and enzyme co-factors. In certain embodiments, it will be advantageous to employ probes or primers as described herein in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In one embodiment, the probe or primer or probe is lyophilized. Lyophilization is a dehydration process typically used to preserve or increase the stability of or, alternatively, increase the stability at ambient temperature of compounds, antibodies, and other perishable materials. Lyophilization also makes the material more convenient for transport. Lyopholization works by freezing the material and then reducing the surrounding pressure to allow the frozen water in the material to sublime directly from the solid phase to the gas phase. Reconstitution of lyophilized agents can be performed with a suitable solution, saline or water, for example, prior to use. Methods for lyophilization are well known in the art (See, for example, US publication 2004/0081588 and US publication 2005/0226893 both of which are incorporated herein by reference in their entirety).

In a further embodiment, the primer or probe is conjugated to a solid support. A solid support may include, for example, a bead (i.e. metallic, agarose, sepharose, etc. . . . ), a micro-array, a gene chip, and the like.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids used in the methods of the disclosure can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane. See, e.g., Letsinger et al. (1989) Proc. Natl. Acad. Sci. U.S.A. 86:6553-6556; Lemaitre et al. (1987) Proc. Natl. Acad. Sci. 84:648-652; and PCT Publ. No. WO 88/09810, published Dec. 15, 1988), hybridization-triggered cleavage agents, (see, e.g., Krol et al. (1988) BioTechniques 6:958-976) or intercalating agents (see, e.g., Zon (1988) Pharm. Res. 5:539-549. To this end, the nucleic acid used in the methods of the disclosure may be conjugated to another molecule, e.g., a peptide, hybridization triggered cross-linking agent, transport agent, hybridization-triggered cleavage agent, etc.

The isolated nucleic acids used in the methods of the disclosure can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the disclosure can be prepared according to methods known in the art and described, e.g., in Sambrook et al. (2001) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Modifications to nucleic acids may also include, for example, Acrydite™ Acrydite-modified oligonucleotides covalently react with thiol-modified surfaces or can be incorporated into polyacrylamide gels during polymerization.

A nucleic acid may also be modified with adenylation. T4 RNA Ligase uses ATP to adenylate the 5'-end of a single-strand nucleic acid sequence. This activated adenylated-oligo is then covalently connected (ligated) to the 3'-OH of a second single-stranded sequence. Adenylated oligonucleotides containing a pyrophosphate linkage are substrates for T4 RNA Ligase in the absence of ATP (1). Oligonucleotide can be adenylated for use with RNA-Ligase using chemical adenylation. T4 RNA Ligase will use an adenylated DNA linker with similar efficiency as an adenylated RNA linker.

A further modification/conjugate includes azide. Azide modification may use an NHS Ester functional group to attach an azide moiety at the 5', 3' or any internal position in an oligo. This azide moiety may subsequently be used to attach alkyne modified groups through the click reaction. The internal version of this modification is attached to the oligo through a dT base. Incorporation of the internal version will add a dT nucleotide at that position. To avoid adding an extra nucleotide, replace an existing T nucleotide in your sequence with the required modification.

A further modification/conjugate includes digoxigenin. Digoxigenin is a small hapten that can be conjugated to amino-modified oligos. Anti-digoxigenin antibodies allow capture or detection of a digoxigenin-labeled oligo and can be used in a variety of assay formats much like biotin/streptavidin.

A further modification/conjugate includes cholesteryl-TEG. Cholesterol can be conjugated to oligonucleotides and can facilitate uptake into cells. It has been used as a transfection aid for antisense oligos and siRNAs, both in vitro and in vivo. Cholesterol is a very hydrophobic modification that is best purified using RP-HPLC.

Further modifications/conjugates include I-Linker™, amino modifiers, alkyne modifiers, biotinylation, desthiobiotin-TEG, PC biotin, dual biotin, biotin-TEG, biotin dT, biotin (azide), thiol modifications, and conjugation to dyes such as Alexa Fluor® 488, Alexa Fluor® 532, Alexa Fluor® 546, Alexa Fluor® 594, Alexa Fluor® 647, Alexa Fluor® 660, Alexa Fluor® 750, CY3™, CY5™, CY5.5™, ATTO™

488, ATTO™ 532, ATTO™ 550, ATTO™ 565, ATTO™ Rho101, ATTO™ 590, ATTO™ 633, ATTO™ 647N, Rhodamine Green™, Rhodamine Red™, 5-TAMRA™, WellRED D4 Dye, WellRED D3 Dye, WellRED D2 Dye, 6-FAM, Texas Red®, Lightcycler® 640, and Dy 750.

Further modifications include dark quencher modifications such as, for example, Iowa Black® FQ, Iowa Black® RQ, Black Hole Quencher®-1, Black Hole Quencher®-2, and Dabcyl; spacers such as C3 spacer sphophoramidite, photo-cleavable spacer, hexanediol, triethylenge glycol spacer, hexa-ethyleneglycol spacer, and 1',2'-dideoxyribose modification; and modified bases such as 2-aminopurine, trimer-20, 2,6-diaminopurine, 5-bromo dU, deoxyUridine, inverted dT, inverted dideoxy-T, dideoxy-C, 5-mehthyl dC, deoxyInosine, locked nucleic acids, 5-nitroindole, 2'-O-methyl RNA bases, and hydroxmethyl dC.

Further modifications include addition of a 3'-terminal ribose that can be used to prevent cross-contamination of amplified sequences. Also included are 2' Fluoro bases which have a fluorine modified ribose which increases binding affinity and also confers some relative nuclease resistance when compared to native RNA.

Also included are phosphorothioate bond modifications. The phosphorothioate (PS) bond substitutes a sulfur atom for a non-bridging oxygen in the phosphate backbone of an oligo. This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds throughout the entire oligo will help reduce attack by endonucleases as well.

3. Primers for the Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the lincRNA of interest or fragment thereof and are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

4. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

5. Compositions

The disclosure also includes compositions comprising the nucleic acids described herein for the purposes of diagnostics. Such compositions can include components such as a carrier, a buffer, a salt, an enzyme, a DNA stabilizing molecule and the like. Non-limiting examples include a polymerase (e.g. Taq polymerase), deoxynucleoside triphosphates, divalent cations, water, a buffer (e.g. TAPS, bicine, tris, tricine, TAPSO, hepes, TES, MOPS, PIPES, cocodylate, ssc, MES, succinic acid, etc. . . . ), EDTA, and the like. The compositions may include the nucleic acid described herein with one or more modifications and/or conjugations as described herein.

IV. Methods of Treatment

This disclosure also provides methods for treating patients with leukemia. Method aspects relate to a method for treating a patient with B-lymphoblastic leukemia comprising a) determining the patient has increased expression of a BALIR molecule in blood or bone marrow cells from the patient as compared to a control or reference level of expression; and, b) administering to the patient prednisone, chemotherapy, radiation, or a bone marrow or cord blood transplant, or a combination thereof.

In a further embodiment, the control or reference level is the expression level of the BALIR molecule in non-B-lymphoblastic leukemia cells.

A further aspect relates to a method of treating a patient determined to have or suspected of having B-lymphoblastic leukemia comprising administering prednisone or prednisolone to the patient after the patient is determined not to have an elevated level of BALIR-2 expression compared to the level in a control or reference sample, wherein the sample includes non-leukemic B-cells.

A further method relates to a method of treating a patient determined to have B-lymphoblastic leukemia comprising administering to the patient an effective amount of a pharmaceutical composition comprising an antisense molecule or expression vector as described herein, wherein the expression vector is capable of expressing the antisense molecule. In specific embodiments, the method further comprises administering prednisone, prednisolone, one or more chemotherapeutics, radiation, or immunotherapy to the patient. The pharmaceutical composition may be given in a single dose at one time point, multiple doses at multiple time points, or in multiple doses at a single time point.

A further method aspect relates to a method for treating a lymphoblastic leukemia in a subject in need thereof comprising administering a BALIR inhibitor to the subject. In one embodiment, the lymphoblastic leukemia is B-ALL. In a further embodiment, the BALIR is BALIR 2. In yet further embodiments, the BALIR is a BALIR listed in Table 1. The BALIR inhibitor may be an inhibitory nucleic acid (or expression vector or host cell comprising the inhibitory nucleic acid) as described herein or a glucocorticoid such as prednisolone or prednisone. In certain embodiments, prednisolone or prednisone is contraindicated and is a treatment deemed not to be effective in the treatment of certain leukemias.

Also provided is a method for increasing apoptosis in an apoptotic-resistant cell comprising administering to the cell a composition comprising a BALIR inhibitor. BALIR inhibitors are described herein and include, for example, an inhibiting nucleic acid, an expression vector comprising an inhibiting nucleic acid, and a glucocorticoid. In one embodiment, the inhibiting nucleic acid is an antisense molecule. In a further embodiment, the BALIR is BALIR-2. In another embodiment, the BALIR inhibitor is a glucocorticoid selected from prednisolone and prednisone. It is specifically contemplated that glucocorticoids such as prednisolone and prednisone are not used for treatment or for increasing apoptosis in an apoptotic-resistant cell when increased expression of BALIR-2 is detected.

The term "treating" as used herein is intended to encompass curing as well as ameliorating at least one symptom of the condition or disease. For example, in the case of cancer, a response to treatment includes a reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs. See Johnson et al. (2003) J. Clin. Oncol. 21 (7):1404-1411.

"An effective amount" intends to indicate the amount of a compound or agent administered or delivered to the patient which is most likely to result in the desired response to treatment. The amount is empirically determined by the patient's clinical parameters including, but not limited to the stage of disease, age, gender, histology, sensitivity, toxicity and likelihood for tumor recurrence. The pharmaceutical compositions described herein may be administered in an effective amount.

The term "clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival (DFS), time to tumor recurrence (TTR), time to tumor progression (TTP), relative risk (RR), toxicity or side effect.

The term "likely to respond" intends to mean that the patient of a genotype is relatively more likely to experience a complete response or partial response than patients similarly situated without the genotype. Alternatively, the term "not likely to respond" intends to mean that the patient of a genotype is relatively less likely to experience a complete response or partial response than patients similarly situated without the genotype.

The term "suitable for a therapy" or "suitably treated with a therapy" shall mean that the patient is likely to exhibit one or more desirable clinical outcome as compared to a patient or patients having the same disease and receiving the same therapy but possessing a different characteristic that is under consideration for the purpose of the comparison. In one aspect, the characteristic under consideration is expression level of a lincRNA. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In further another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcomes are considered simultaneously. In one such aspect, a patient possessing a characteristic, such as an increased expression level of a lincRNA, may exhibit more than one more desirable clinical outcomes as compared to a patient to patients having the same disease and receiving the same therapy but not possessing the characteristic. As defined herein, the patient is considered suitable for the therapy. In another such aspect, a patient possessing a characteristic may exhibit one or more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, disease free survival, progression free survival or overall survival is weighted more heavily than tumor response in a collective decision making.

A "complete response" (CR) to a therapy defines patients with evaluable but non-measurable disease, whose tumor and all evidence of disease had disappeared.

A "partial response" (PR) to a therapy defines patients with anything less than complete response that were simply categorized as demonstrating partial response.

"Stable disease" (SD) indicates that the patient is stable.

"Progressive disease" (PD) indicates that the tumor has grown (i.e. become larger), spread (i.e. metastasized to another tissue or organ) or the overall cancer has gotten worse following treatment. For example, tumor growth of more than 20 percent since the start of treatment typically indicates progressive disease. "Disease free survival" indicates the length of time after treatment of a cancer or tumor during which a patient survives with no signs of the cancer or tumor.

"Non-response" (NR) to a therapy defines patients whose tumor or evidence of disease has remained constant or has progressed.

"Overall Survival" (OS) intends a prolongation in life expectancy as compared to naive or untreated individuals or patients.

"Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease.

"Disease free survival" (DFS) refers to the length of time during and after treatment that the patient remains free of disease.

"No Correlation" refers to a statistical analysis showing no relationship between the allelic variant of a polymorphic region or gene expression levels and clinical parameters.

"Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer.

"Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up.

"Relative Risk" (RR), in statistics and mathematical epidemiology, refers to the risk of an event (or of developing a disease) relative to exposure. Relative risk is a ratio of the probability of the event occurring in the exposed group versus a non-exposed group.

The term "determine" or "determining" is to associate or affiliate a patient closely to a group or population of patients who likely experience the same or a similar clinical response.

A "tumor" is an abnormal growth of tissue resulting from uncontrolled, progressive multiplication of cells and serving no physiological function. A "tumor" is also known as a neoplasm.

A. Routes of Administration

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

Administration according to the methods described herein may be by any number of routes including, but not limited to oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, intraosseously or rectal. Further details on techniques for formulation and administration may be found in the latest edition of Remington's Pharmaceutical Sciences (Maack Publishing Co., Easton, Pa.). In certain embodiments bucindolol is formulated for oral administration. In one embodiment, the composition is administered intravenously, intraosseously, orally, intraarterially, intraperitoneally, or by direct injection.

B. Pharmaceutical Compositions

Where clinical applications are contemplated, pharmaceutical compositions will be prepared in a form appropriate for the intended application. Generally, this will entail preparing compositions that are essentially free of pyrogens, as well as other impurities that could be harmful to humans or animals. The pharmaceutical compositions described herein may contain a nucleic acid of the disclosure (i.e. an antisense molecule, an expression vector, etc. . . . ). In certain embodiments, the pharmaceutical composition comprises at least two different antisense molecules described herein.

When the composition comprises an expression vector, it may be an expression vector as described herein. In one embodiment, the expression vector is a viral vector. In a related embodiment, the viral vector is a lentiviral vector, an adenovirus vector, an adeno-associated virus vector, or a herpesvirus vector.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The composition may comprise a delivery system. Various delivery systems are known and can be used to administer therapeutics according to the methods of the disclosure, e.g., encapsulation in liposomes, microparticles, microcapsules, expression by recombinant cells, receptor-mediated endocytosis. See e.g., Wu and Wu (1987) J. Biol. Chem. 262:4429-4432 for construction of a therapeutic nucleic acid as part of a retroviral or other vector, etc.

The pharmaceutical composition may be given in a single dose at a single time point, in multiple doses at multiple time points, in single doses at multiple time points, or in multiple doses at a single time point.

V. Combination Therapy

The pharmaceutical compositions described herein may be used in conjunction with other therapies known for treating leukemia.

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery. The section below describes some adjunct cancer therapies:

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, Ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristine, vinblastine and methotrexate, or any analog or derivative variant of the foregoing.

B. Radiotherapy

Other factors that cause DNA damage and have been used extensively include what are commonly known as .gamma.-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p 97), gp68, TAG-72, HMFG, Sialyl Lewis Antigen, MucA, MucB, PLAP, estrogen receptor, laminin receptor, erb B and p 155.

D. Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

EXAMPLES

I. Materials and Methods

The following materials and methods are included to demonstrate application to experiments below. It should be appreciated by those of skill in the art that the techniques disclosed in the materials and methods which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Patients and Samples.

The patients consisted of 160 children consecutively admitted to the Pediatric Oncologic Department at the University of Padua, Italy, from 2000 to 2008 with the diagnosis of ALL. The enrollment criteria of the study were: newly diagnosed ALL, age range from 0 to 18 years, and written informed consent of the parents following the AIEOP (Italian Association of Pediatric Hematology and Oncology) and the BFM (Berlin-Frankfurt-Muenster) ALL 2000 trial. The diagnosis of ALL was established according to conventional criteria such as morphology, immunophenotyping and molecular genetics. We excluded any cases that were subsequently revealed to be T-ALL based on the above parameters. The Philadelphia chromosome t(9;22) (q34;q11.2), the t(12;21)TEL-AML1, the t(1;19)E2A-PBX and t(4;11)MLL-AF4 were detected by conventional cytogenetic analysis, fluorescent in situ hybridization, or by reverse transcription-quantitative polymerase chain reaction (RT-qPCR) of the fusion genes. For the initial microarray studies, we utilized 20 patients made up of 7 patients t(4;11) MLL rearranged, 6 t(12;21) TEL-AML1 translocated and 7 t(1,19) E2A-PBX translocated. For the validation microarrays, an additional 24 samples with the same translocations were hybridized. For the independent validation by RT-qPCR of the samples, we utilized 100 new samples of ALL de novo without selection criteria collected from 2000 to 2010 at the OncoHematology laboratory of the Pediatric Department at the University of Padua. For each case, we had the following data: genetic marker (28 patients with t(12,21) translocation, 2 patients with t(1;19), 4 patients with t(4;11), 2 t(9;22), and 60 patients were negative for molecular markers), immunophenotype (67 patients were CALL, 12 preB, 7 prepreB, 4 Thym-T and 6 not determined), age (0-18 years), risk stratification by minimal residual disease (following AIEOP protocol (Conter, 2010)), response to prednisone (10 patients were poor prednisone responders, PPR), occurrence of recurrence/relapse, time to recurrence/relapse, overall survival, and time to death. Final analyses were carried out on 93 samples, as 7 samples had to be excluded due to either low RNA quality or T-ALL phenotype upon review of the coded data. All procedures were approved by the local institutional review boards, and the study was considered exempt from review at UCLA.

Microarray Data Analysis.

Microarrays were hybridized at the Caltech microarray core facility using standard techniques. All microarray data analysis was implemented in the R statistics package (R Development Core Team, 2008). A total of 44 Agilent microarrays were collected from two microarray experiments performed in two batches with 20 and 24 microarrays in each run. The data from two microarray experiments were analyzed independently but following the same protocol. The Agilent feature extraction raw data files were loaded into the R environment and analyzed using the R library of the Linear Models for Microarray Data (LIMMA) (Smith, 2004). The raw data were preprocessed for background correction and normalized between arrays using quantile method. The data was then summarized by taking average of the replicates of each gene and log 2 transformed. A linear model was fitted to the expression data using lmFit function and the empirical Bayes (eBayes) method was employed to rank genes for differential expression analysis. The adjusted p-values for genes were obtained after the Benjamini and Hochberg method was applied to the results from the eBayes method.

Supervised class prediction using lincRNA expression profile or coding gene expression profile was carried using the R library of prediction analysis for microarrays (PAM), which is a machine learning program by shrunken centroids of gene expression (Tinshirani, 2002). The expression data from 20 microarrays were used as the training data and the data from 24 other microarrays were used for the class prediction. In brief, the training datasets were trained using the pamr.train program and the training result was evaluated by 10-fold cross-validation. Misclassification error from the cross-validation of training data was examined and the shrinkage threshold values that gave the least classification error were chosen and used to classify the data from 24 microarrays.

Clinicopathologic Data Analysis.

Data analysis was completed using SPSS software. Initially, the existing clinicopathologic parameters were correlated with the continuous qPCR data obtained for each of the BALIRs. For this purpose we used a Pearson's Chi-square as the data was continuous and the outcome variable was dichotomized. We also performed correlational analyses between the various clinicopathologic parameters and internally validated the data set. Next, for survival analyses, we dichotomized BALIR-2 expression into low and high expressors, based on the finding of two clusters of data within the distribution (two-step clustering analysis using SPSS software). This allowed us to compare overall survival in these two subsets of patients, and the cut point was defined based on the point at which the clustering analyses showed a statistically significant difference. For BALIR-2, a two sample non parametric Kolmogorov-Smirnov test was applied to these two clusters which shows that the clusters or groups are statistically significant (two tail asymptotic significance (p-value) almost 0). Similar clustering approaches were performed to dichotomize expression levels for BALIR-1, BALIR-6, and BALIR-11. Correlational analyses failed to show a significant correlation with survival or other clinicopathologic parameters of importance.

Knockdown Vectors.

We designed two complementary "linker" strands containing restriction sites for BamHI (5' intact), XhoI, XbaI, NheI, ApaI and BamHI (3' mutated) as follows: 5'-GATC-CACCTCGAGTATCTAGAATGCTAGCTTGGGC- CCACT-3' (forward) (SEQ ID NO. 11), 5'-GATCA-GTGGGCCCAAGCTAGCATTCTAGATACTCGAGGTG-3' (reverse) (SEQ ID NO. 12). The oligonucleotides were ordered through Invitrogen and modified with 5'-phosphate groups. The complementary strands were annealed by heating to 100° C. and slowly cooling in a water bath. The pHAGE2-CMV-ZsGreen-W vector (previously described in (O'Connell, 2010)) was digested with BamHI (Fermentas) and the linker was ligated in using T4 DNA ligase (Fermentas). Colonies were sequenced (Laragen) to determine the correct orientation and verify the sequence of the insert and mutation of the 3' BamHI site. miRNA-formatted siRNAs were cloned into BamHI and ApaI or XhoI in the P2CZL vector, using the strategy that we have previously described to generate knockdown vectors against protein coding genes (O'Connell, 2009; Rao, 2010).

P6CZUL and P6CZML vectors were created by cloning UBC (provided by Dr. Alejandro Balazs) and MNDU (provided by Dr. Gay Crooks) promoters between the SpeI and NotI sites of the pHAGE6-TRE2-Luc2-DR-W-CMV-Zs-Green vector (provided by Dr. Alejandro Balazs) respectively. Full length BALIR-2 was cloned between NotI and BamHI sites in the P6CZUL and P6CZML vectors.

Cell Culture and Flow Cytometric Analysis.

NALM6 and RS411 human pre B-cell leukemia cell lines were cultured in RPMI-1640 (Cellgro) supplemented with 10% heat-inactivated FBS (Cellgro), 100 U/ml penicillin (Cellgro), and 100 µg/mL streptomycin (Cellgro). 293T cells were cultured in DMEM (Cellgro) with 10% heat-inactivated FBS (Cellgro), 100 U/ml penicillin (Cellgro), and 100 µg/ml streptomycin (Cellgro). All cell lines were grown at 37° C. in a 5% $CO_2$ humidified incubator (Eppendorf). Cell lines were provided by Dr. Gay Crooks and Dr. Kathy Sakamoto. Transduced cell lines were sorted using a BD FACSAriaII cell sorter and BD FACSDiva software. Cells were gated to exclude dead cells, and desired populations were collected.

Apoptosis, Proliferation and Drug Response Assays.

To measure proliferation, cells were cultured for 3-5 days before plating. Reagents were added according to the manufacturer's instructions (Promega CellTiter 96 AQueous Non-Radioactive Cell Proliferation Assay kit) and cells were incubated at 37°, 5% $CO_2$ for 4 hours before absorbance was measured at 490 nm. To measure apoptosis, cells were plated and treated with 100 ng/mL doxorubicin or 250 µg/mL prednisolone in DMSO and incubated at 37° C. and 5% $CO_2$. An untreated group and DMSO-treated group were included as controls. Cells were harvested after 24 hours and lysed with buffer supplied by Biovision. Protein concentrations were normalized after measurement by Bradford assay. Reagents were added according to the manufacturer's instructions (Biovision Caspase-3 Colorimetric Assay kit) and absorbance was measured at 405 nm. To observe the effects of prednisolone on lincRNA expression, untransduced cell lines were plated and treated with either 250 µg/mL prednisolone in DMSO or DMSO alone as a control. Cells were incubated at 37° C. and 5% $CO_2$ for 24 hrs. Cells were collected and RNA was extracted using Trizol reagent (Invitrogen).

Transfection, Lentiviral Production and Transduction.

All lentiviruses were produced by transfecting 293T adherent cells with knock-down vectors as listed in Table 1, using BioT transfection agent (Bioland Scientific). $2.5 \times 10^5$ 293T cells were co-transfected in trans using an advanced generation lentiviral system in 6 well plates for 48 hours as described previously (O'Connell, 2010). At 48 hours, the viral supernatant was collected, filtered and used for spin infection of B-ALL cell lines. $5.0 \times 10^5$ cells were spin-infected at 30° C. for 90 minutes in the presence polybrene (4 µg/mL). Transduced cells were sorted for high ZsGreen expression as described above.

RT-qPCR.

RNA collected from samples was reverse transcribed using qScript reagent (Quanta Biosciences). Real Time quantitative PCR was performed with the StepOnePlus Real-Time PCR System (Applied Biosystems) using PerfeCTa SYBR Green FastMix reagent (Quanta Biosciences). Primer sequences used are listed in Table 1.

RACE and Cloning of lincRNA.

To determine the 5' and 3' transcript ends of the lincRNAs, we performed RACE (Rapid Amplification of cDNA Ends) using FirstChoice RLM-RACE kit (Ambion). Using the sequence information from 5' and 3' RACE products, we cloned full length transcripts into P6CZUL, P6UZCL and P6CZML vectors between the NotI and BamHI sites. Primer sequences used in RACE and cloning are listed in Table 1.

II. Results

The following results provide working examples of embodiments described and claimed herein.

LincRNA Expression Segregates Three Common Cytogenetic Subtypes of ALL.

Figure 6B:
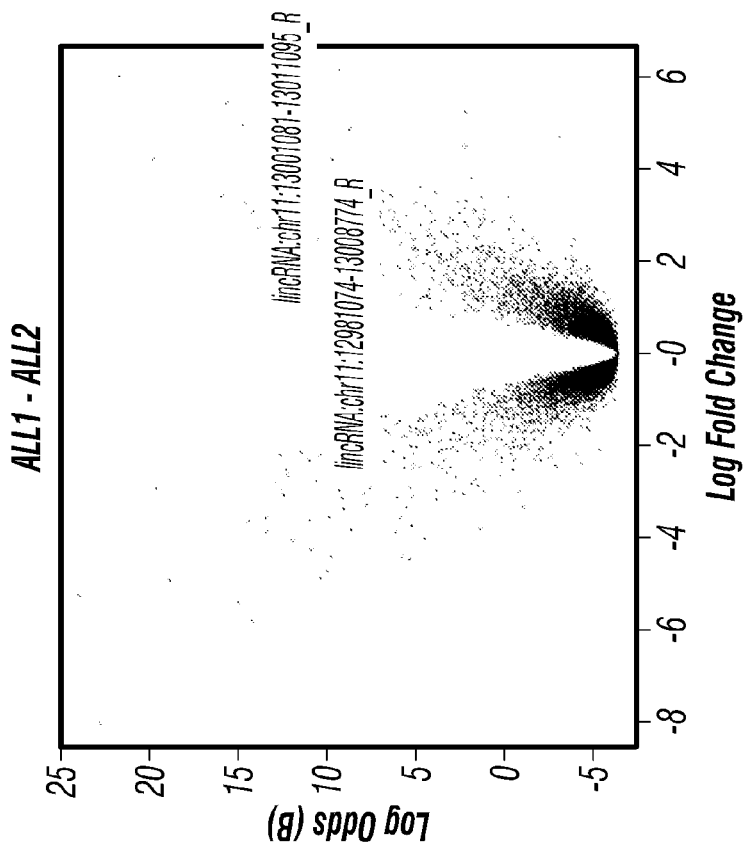
FIGS. 6A-6D—Computational analysis confirms lincRNA differential expression in ALL subtypes. (A) Principal component analysis separates B-ALL cases into three cytogenetic subtypes based on the expression of lincRNAs. (B-D) Volcano plots comparing two subtypes of ALL (ALL1 VS ALL2 (B), ALL1 VS ALL3 (C) and ALL2 VS ALL3 (D)) show that lincRNAs are among the most differentially regulated genes.
Figure 6A:
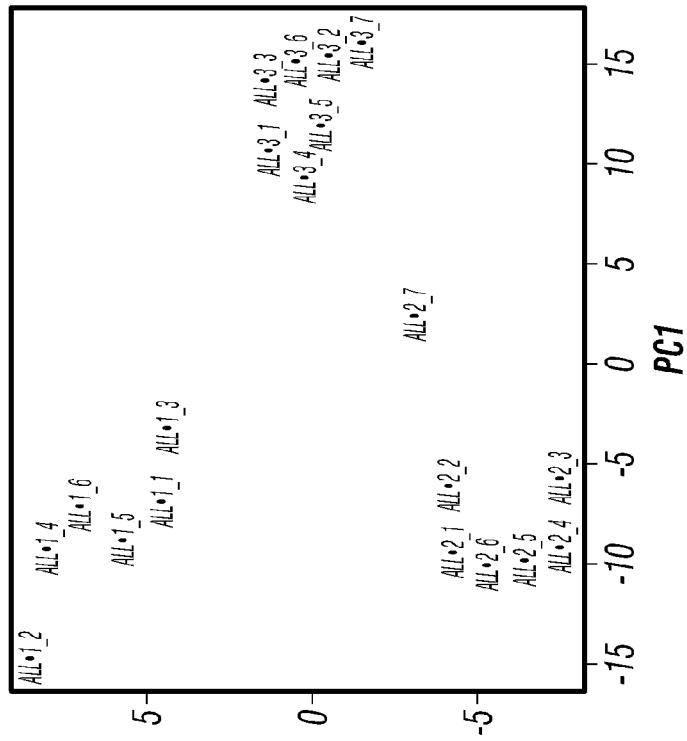
Figures 6C, 6D:
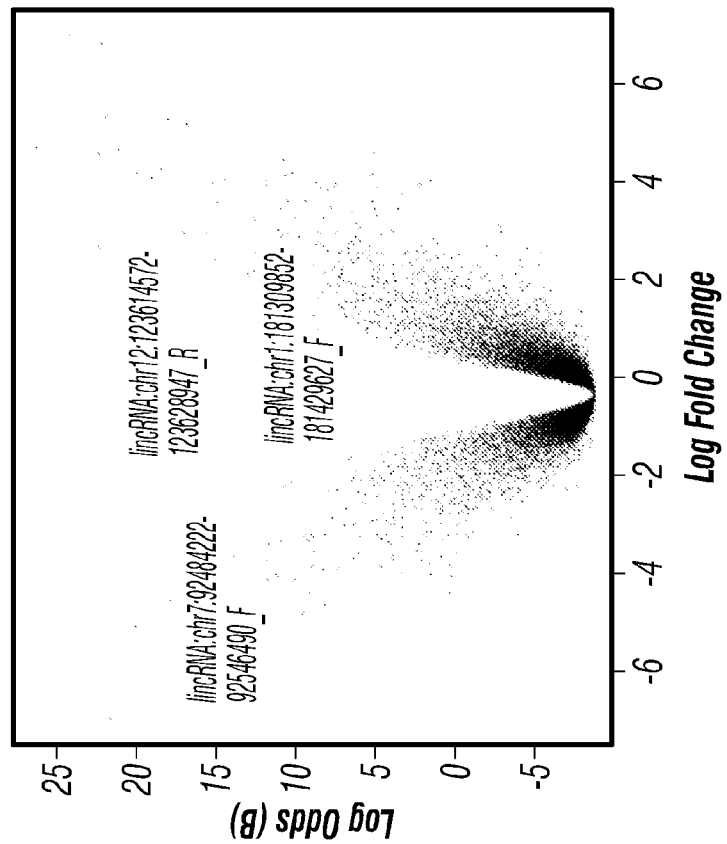

LincRNAs have been ascribed functions in cancer causation and development of the hematopoietic system. To determine whether these RNA molecules are involved in different oncogenic pathways in B-ALL, we undertook a microarray study to define patterns of lincRNA expression in different subsets of B-ALL. For this purpose we utilized the Agilent SurePrint microarray platform constructed by John Rinn and his colleagues (Guttman, 2009; Rinn, 2007; Khalil, 2009). In our initial sample set, we hybridized 20 cases of B-ALL of three different cytogenetic subtypes, namely t(12;21), TEL-AML1 translocated (n=6); t(1;19) E2A-PBX translocated (n=7); and 11q23 (MLL)-rearranged cases (n=7). As expected, when we performed unsupervised hierarchical clustering with significantly regulated protein-coding genes (p-adj≤0.01), the three cytogenetic subtypes separated very distinctively into three subsets (FIG. 1A). Interestingly, when we used and focused exclusively on lincRNAs (p-adj≤0.01), the same relationship held up. The separation of these clusters by lincRNA alone was confirmed by principal component analysis (FIG. 6A). LincRNAs were expressed in distinctive patterns across the 3 different cytogenetic subtypes, as shown by lincRNAs that were differentially expressed with an adjusted p-value of less than 0.01 (FIG. 1B). In addition, lincRNAs were amongst the most differentially regulated genes when each pair of ALL subtypes was compared (FIG. 6B-6D). The top 10 differentially expressed lincRNAs were designated as B-ALL associated long intergenic RNAs (BALIRs) and assigned various numbers, unless they had already been assigned LINC designations at the UC Santa Cruz genome browser. Expression of individual lincRNAs showed some variation on the microarrays within cytogenetic subtypes; four examples are plotted in FIGS. 1C-1F. These are BALIR-1, BALIR-2, BALIR-6, and BALIR-11, respectively.

LincRNA Expression can be Predictive of the Cytogenetic Subtype of ALL.

Figures 2A, 2B, 2C, 2D, 2E, 2F:
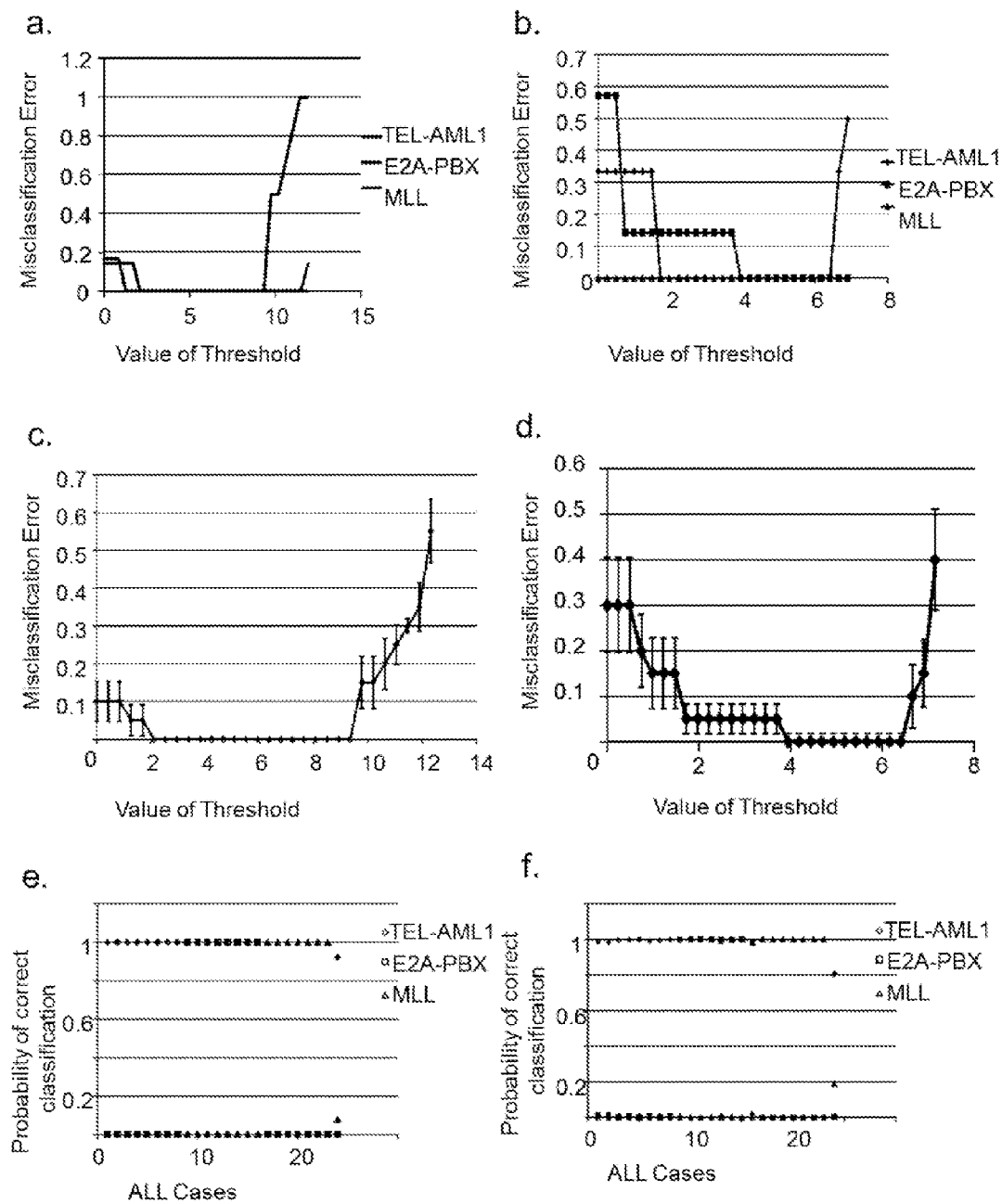
FIGS. 2A-2F—LincRNA expression can predict the cytogenic subtype of ALL. Class prediction of the subtypes of B-ALL using the nearest shrunken centroid method. (A-D) Using 20 microarray data as the training data to identify the subsets of protein coding genes (A, C) or lincRNAs (B, D) that can distinguish B-ALL subtypes. The misclassification error and the number of genes for each threshold were computed using the R library of prediction analysis for microarrays (PAM). Individual (A-B) and cumulative (C-D) cross-validation error of PAM model are shown as a function of the threshold. Error bars show the standard error. (E-F) Prediction results of the 24 independent samples of B-ALL. One of the 8 MLL samples was misclassified as TEL-AML1 when the threshold was set at 4.676 for the coding genes or 3.969 for the lincRNA27 lincRNA.
Figures 3A, 3B, 3C, 3D, 3E, 3F, 3G, 3H:
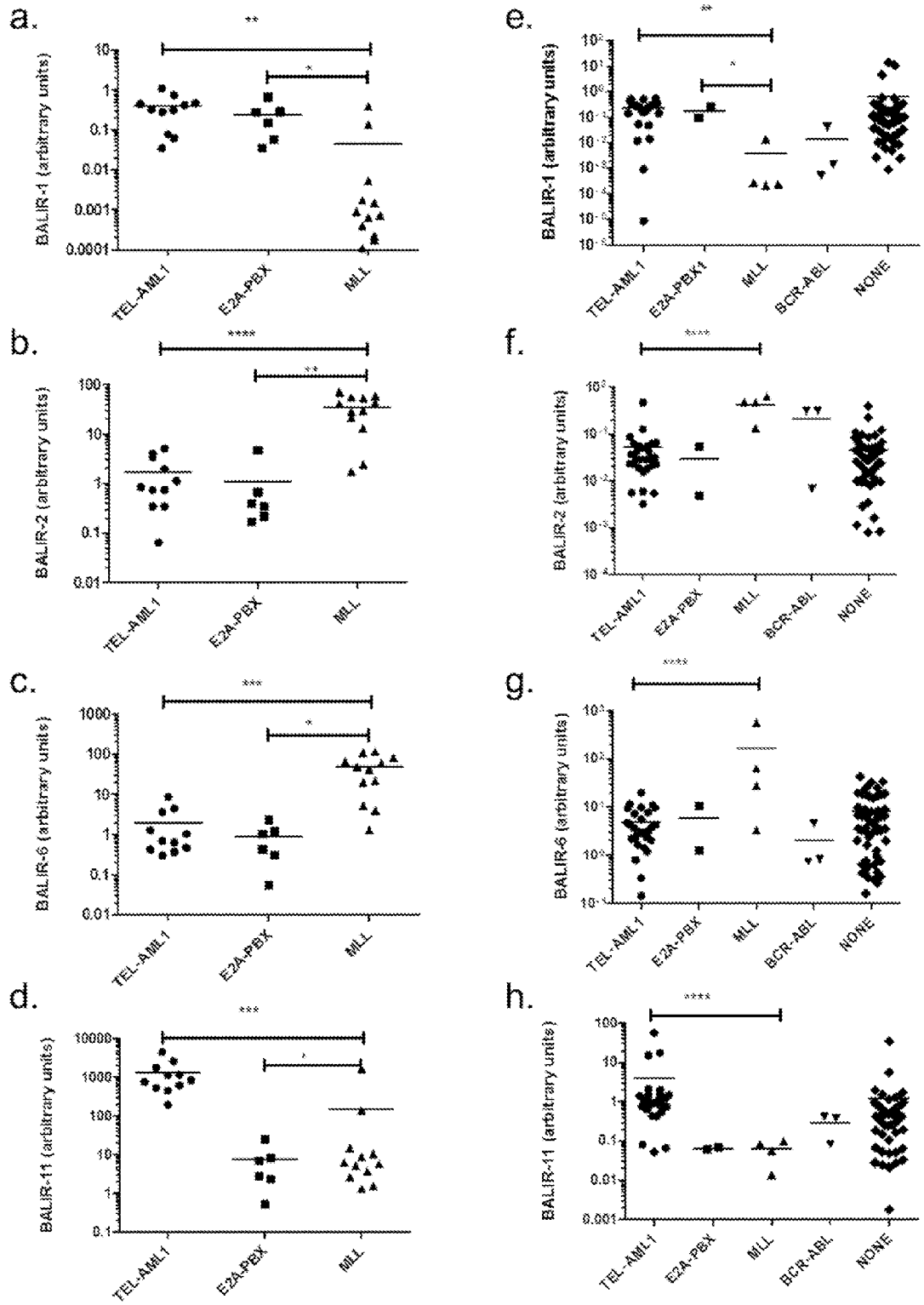
FIGS. 3A-3H—Differential lincRNA expression is confirmed by RT-qPCR. (A-D) RT-qPCR of the original cohort with primers specific for BALIR-1, BALIR-2, BALIR-6 or BALIR-11, normalized to Actin, showing differential expression between subsets based on translocations. TEL-AML1 n=11, E2A-PBX n=6 and MLL n=12. (E-H) RT-qPCR of an independent set of clinical samples, using the same primers as in (A), is showing differential expression between subsets and a range of lincRNA expression in patients with no translocations. TEL-AML1 n=28, E2A-PBX n=2, MLL n=7, BCR-ABL n=3 and none n=56.

Prior studies have demonstrated the strength of using expression profiles to characterize various disease subtypes. For example, early studies showed that gene expression profiles from microarrays were able to distinguish acute lymphoblastic leukemia from acute myeloid leukemia (Tibshirani, 2002; Tibshirani, 2003; Golub, 1999). More recently, profiling of microRNAs has demonstrated that expression of non-coding elements of the genome can be predictive of the histogenesis/cell of origin of a tumor (Lu, 2005). In a similar manner, we wanted to determine whether lincRNA expression was predictive of cytogenetic abnormalities in B-ALL. We used nearest shrunken centroid analysis to train the gene expression profile from 20 microarrays and identify a subset of protein coding genes (FIG. 2A and FIG. 2C) and lincRNAs (FIG. 2B and FIG. 2D) that can efficiently predict cytogenetic subtype in an independent set of B-ALL cases. The 10-fold cross-validation results for each subtype of ALL (FIG. 2A and FIG. 2C) and for the whole training datasets (FIG. 2B and FIG. 2D) were shown as a function of the threshold, a parameter used to reduce the effect of "noisy" gene expression and to automate gene selection for classification (26). The misclassification errors reached minimum (zero) between the thresholds 2.125 to 9.351 with the gene numbers of 1112 to 4 for protein-coding genes and 3.939 to 6.401 with the gene numbers of 27 to 4 for lincRNAs (FIG. 2A-2D).=We then proceeded to examine the classification of 24 independent samples of B-ALL using the thresholds that produced the minimum error rate. Here, we found that when the threshold was set at 4.676 and the number of protein coding genes used to predict class was decreased to 113, one case of ALL became misclassified; whereas one could use 27 lincRNAs at the threshold 3.969 before the same case was misclassified (FIG. 2E-F). Among these 27 lincRNAs were BALIR-1, BALIR-2, BALIR-6 and BALIR-11 which were differently expressed in the different cytogenetic subtypes as seen in FIGS. 1C-1F. The result indicates that, with a lower number of lincRNAs, the cytogenetic type of the B-ALL can be predicted with accuracy similar to that predicted by a larger number of protein-coding genes. This may indicate that lincRNAs are better at predicting the cytogenetic class of the B-ALL, which would be an interesting finding in light of the proposed roles of lincRNA in regulating transcriptional programs.

Differential lincRNA Expression is Confirmed by RT-qPCR in Both the Original Samples and in an Independent Cohort.

Figures 5A, 5B, 5C, 5D, 5E:
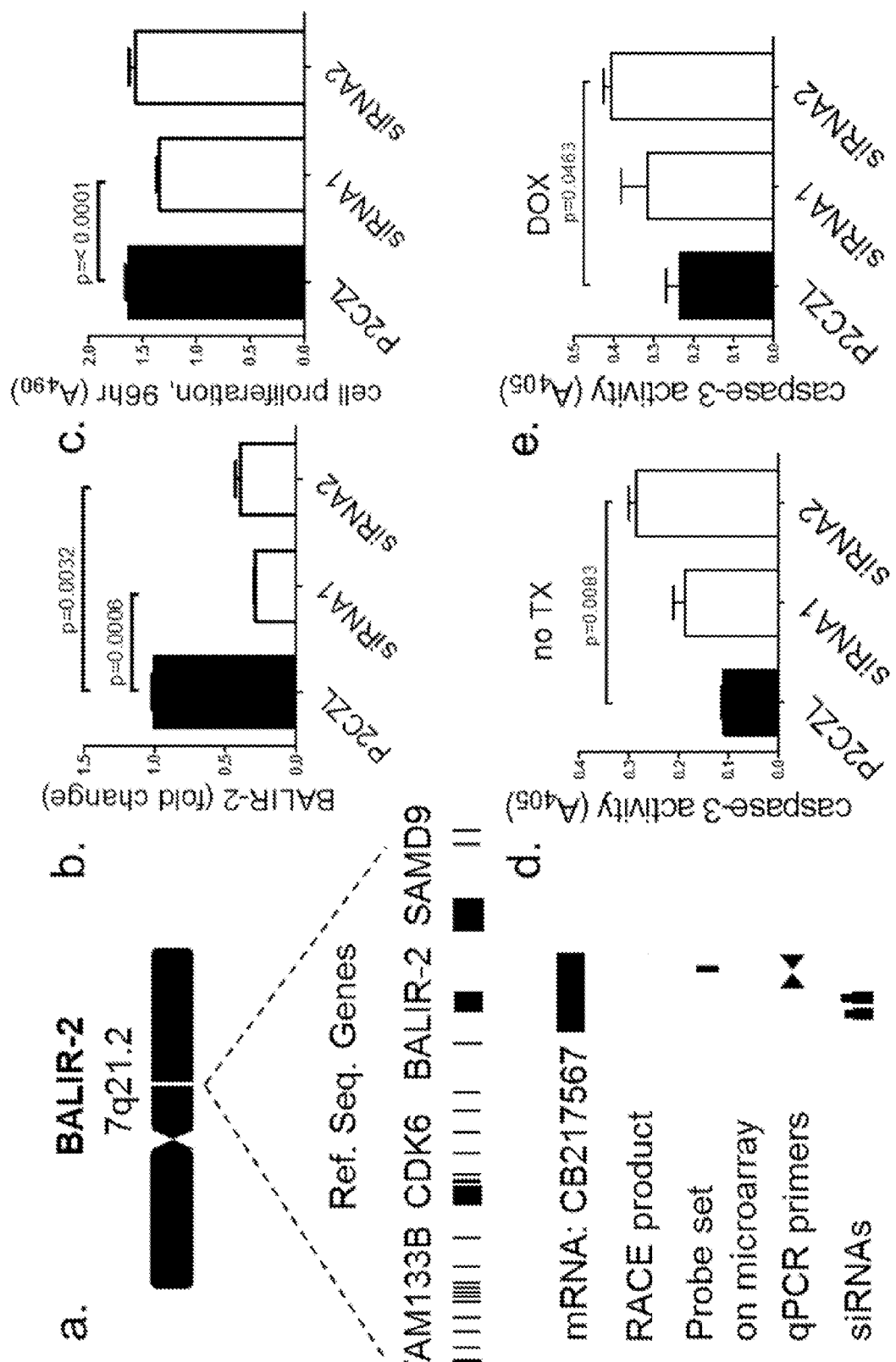
FIGS. 5A-5H—BALIR-2 shows a functional role in B-ALL cell lines. (A) Map showing the position of BALIR-2 in the genome, including the locations of neighboring genes (exons shown in green), corresponding annotated mRNA, probe set on microarray, qPCR primers and siRNAs targeting the lincRNA. (B) siRNA-mediated knockdown of BALIR-2 in RS411 cell line, shown by RT-qPCR (normalized to Actin). (C) Reduction of cell proliferation in RS411 stably transduced with siRNA1 against BALIR-2, measured by MTS assay. (D-G) Increased apoptosis in RS411 stably transduced with siRNA2 against BALIR-2, measured by caspase-3 activity. Treatment groups include no treatment (D), 100 mg/mL doxorubicin (E), DMSO (F) and 250 mg/mL prednisolone in DMSO (G). (H) Reduction in BALIR-2 expression in RS411 treated with prednisolone.
Figures 7A, 7B, 7C:
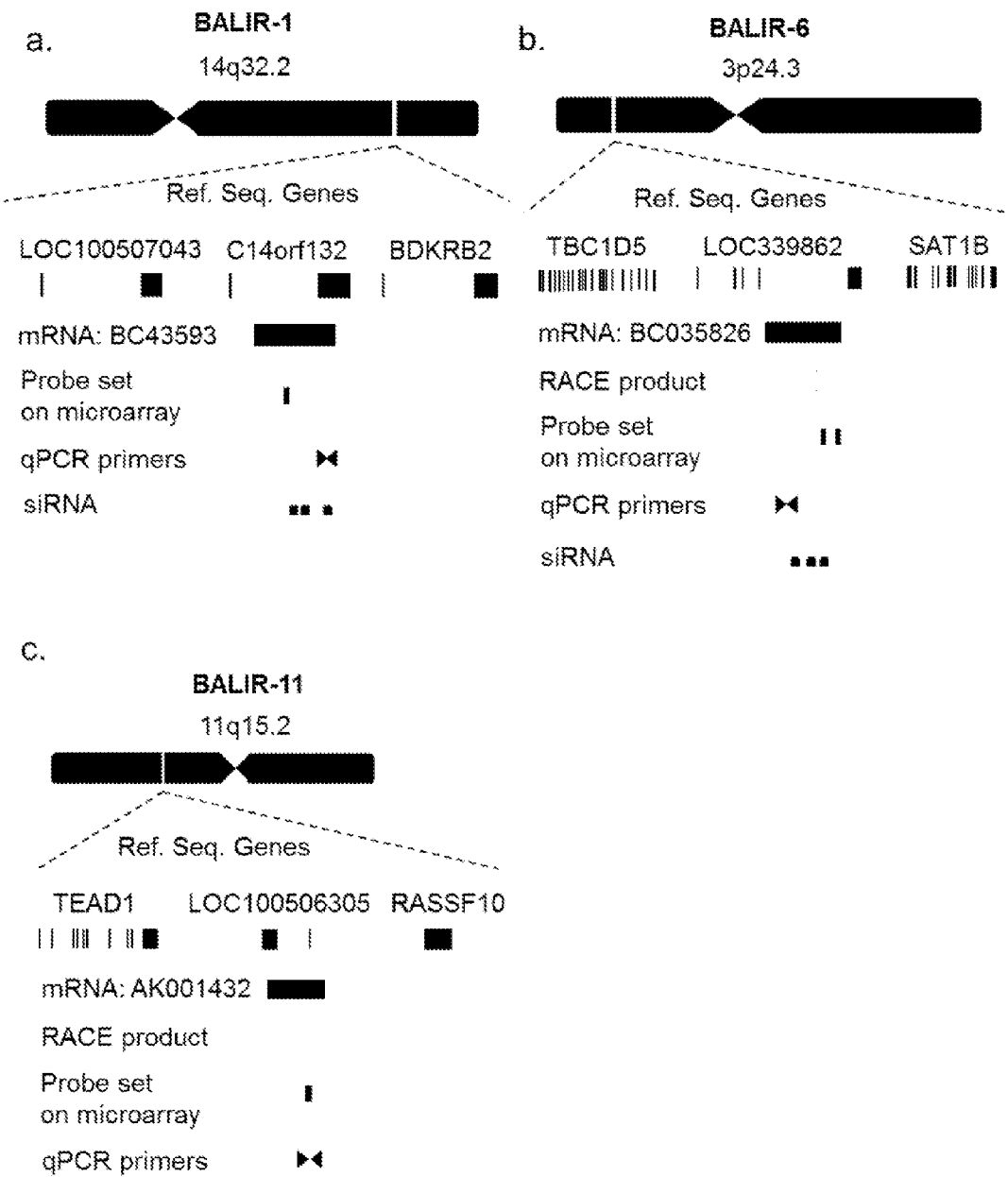
FIGS. 7A-7C—LincRNA positional information. (A-C) Maps showing the positions of BALIR-1 (A), BALIR-6 (B) and BALIR-11 (C) in the genome, including the locations of neighboring genes (exons shown in green), corresponding annotated mRNA, probe set on microarray, qPCR primers and siRNAs targeting the lincRNA (BALIR-1 and BALIR-6 only).

To confirm the findings of the microarray, we next performed individual RT-qPCR reactions to assess the expression patterns of four individual lincRNAs in a subset from the original cohort of B-ALL samples, selected based on RNA quality and availability (FIG. 3A-D), and an independent set of 93 B-ALL samples that were not enriched for any particular translocation (FIG. 3E-H). These four lincRNAs were amongst the 27 discriminant lincRNAs that we defined via PAMR analysis (FIG. 2). Furthermore, these lincRNAs were well-annotated in the genome, i.e., showed multiple ESTs or mRNA transcripts that mapped to the location of the probeset(s) on the microarray, and were conserved in human and mouse genomes (FIG. 7 and FIG. 5A). We assessed the expression of BALIR-1 (14q32.2), BALIR-2 (7q21.2), BALIR-6 (3p24.3) and BALIR-11 (11q15.2). Multiple qPCR primer sets were designed using NCBI Primer-BLAST and tested; those with the most consistent behavior across technical replicates and serial dilutions were chosen (see Table 1, qPCR primers). As can be seen, the qPCR results confirmed that lincRNA expression was most consistently different in the subset of cases with MLL translocation, which is associated with a bad prognosis. For all 4 lincRNAs that we assessed by qPCR, we confirmed that MLL-translocated cases showed significantly different expression levels as opposed to cases with either TEL-AML1 translocations or E2A-PBX1 translocation. Moving on to an independent set of cases, we found that the relationships held up overall, in that MLL-translocated cases showed significantly different lincRNA expression compared with TEL-AML1 translocated cases, and statistically significant differences or a trend towards differential expression was seen between E2A-PBX1 translocated cases and MLL-translocated cases. In this large cohort of cases, there were a significant number of samples that did not harbor any translocations (labeled NONE in FIG. 3E-H). We noticed that there was a large variability of lincRNA expression in these B-ALL cases. Since this heterogeneous group of ALL has an overall intermediate prognosis, we reasoned that it was possible that lincRNA expression may further be used to refine the prognostication of outcomes in these patients.

LincRNA Expression is Correlated with Clinicopathologic Parameters in a Large Set of Cases of ALL.

Figures 4A, 4B:
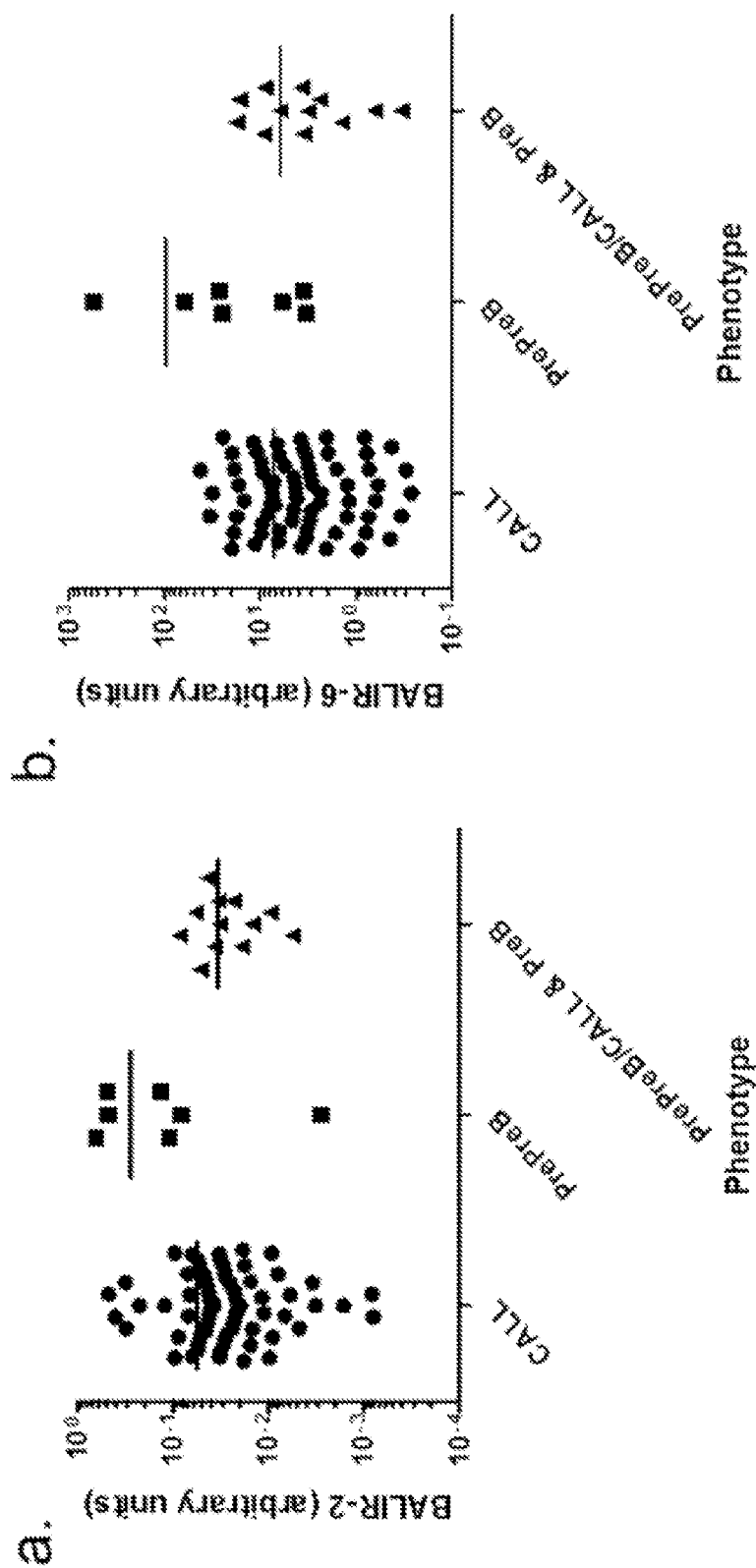
FIGS. 4A-4D—LincRNA expression correlates with clinicopathologic parameters. BALIR-2 (A) and BALIR-6 (B) expression show a significant variation based on B-ALL immunophenotype (1-way ANOVA, $p<0.0001$ for BALIR-2 and $p<0.0004$ for BALIR-6). CALL n=68, PrePreB n=7, PrePreB/CALL & PreB n=12. (C) Analysis of BALIR-2 expression data and response to prednisone treatment shows that BALIR-2 expression is significantly higher in B-ALL patients that are not responsive to prednisone compared to those who do respond to prednisone. (D) Kaplan Meier survival analysis for two groups of BALIR-2 shows that high BALIR-2 expression was associated with poor overall survival (overall survival (OS) high=62.5% (n=82), OS low=91.5% (n=8), log-Rank test, p=0.005). The two groups are based on two step cluster analysis using SPSS software.
Figures 4C, 4D:
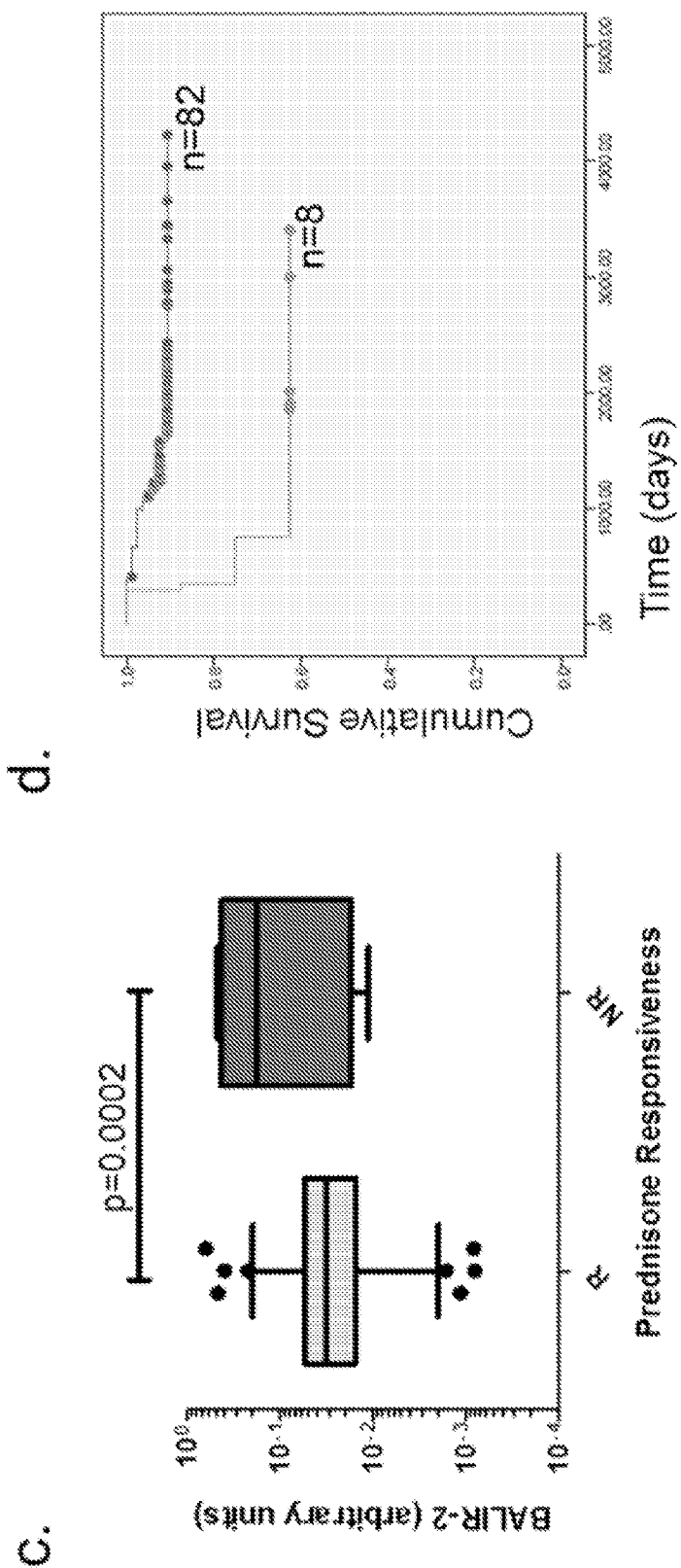
Figure 8A:
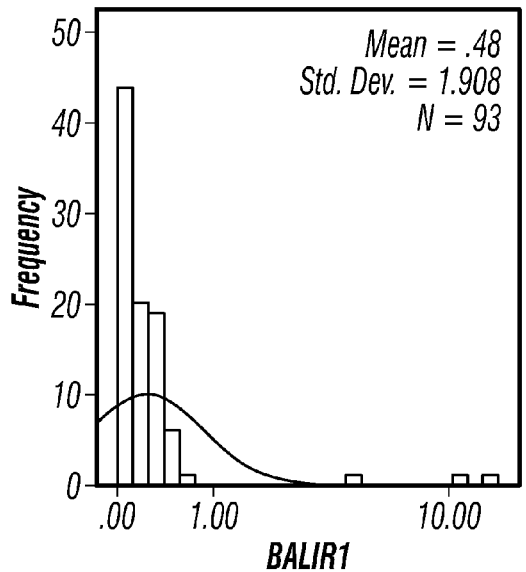
Figure 8B:
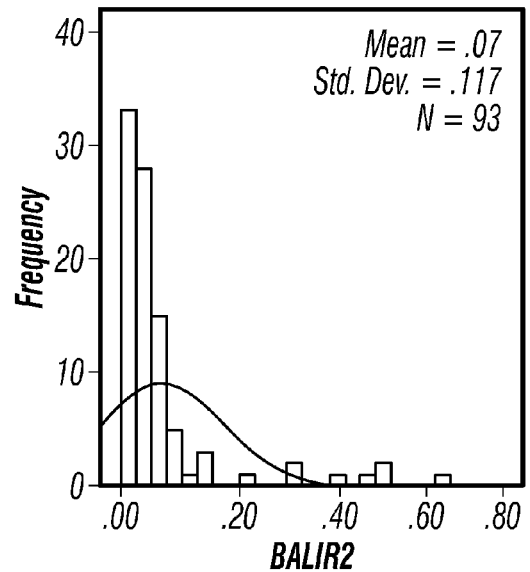
Figure 8C:
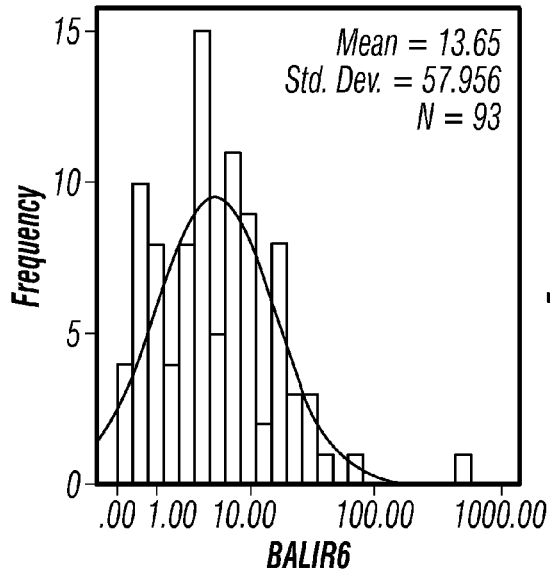
Figure 8D:
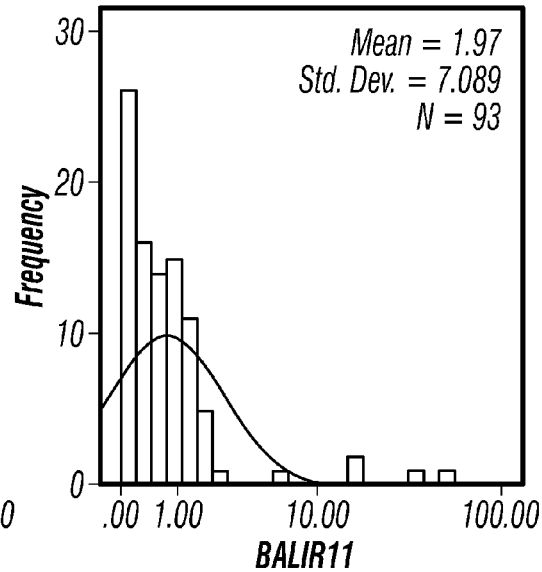

To examine the possibility that lincRNA expression is predictive of patient outcomes, we performed statistical analyses on available clinicopathologic parameters associated with these cases. We then proceeded to calculate whether expression of lincRNAs was significantly different between the various clinicopathologic subtypes of B-ALL (FIG. 4). Interestingly, BALIR-2 showed a significant variation in expression level depending on the immunophenotype of the B-ALL cells (FIG. 4A, 1-way ANOVA, p<0.0001) (Bene, 1995). Similarly, BALIR-6 showed significant variance in the expression level based on the immunophenotype (FIG. B, 1-way ANOVA, p=0.0004). We also looked at responsiveness to drug treatment in the patient samples, finding that BALIR-2 expression was significantly higher. in B-ALL patients that were unresponsive to prednisone as opposed to those who had a response to prednisone (FIG. 4C, two-tailed p>0.0002). When the data of BALIR-2 expression was examined more closely, there appeared to be two clusters within the dataset and the two clusters could be separated based on statistical considerations (FIG. 8B). We then dichotomized BALIR-2 expression using a cut point as described in the methods section. Graphing overall survival using low or high level of BALIR-2 expression showed that high BALIR-2 expression was associated with inferior overall survival in these patients (FIG. 4D; Kaplan Meier survival analysis; log-Rank test, p=0.005,). Although BALIR-2 expression did correlate with translocations, it should be noted that certain cases with high expression were not translocated. When we attempted multivariate logistic regression, BALIR-2 was not established as an independent prognostic variable. This may be due to insufficient numbers of cases with high BALIR-2 expression, and it may require a larger cohort of patients to better define the exact relationship of prognosis with BALIR-2.

Knockdown of Expression of a Dysregulated lincRNA, BALIR2, Results in Growth Inhibition and Increased Apoptosis.

Figures 5F, 5G, 5H:
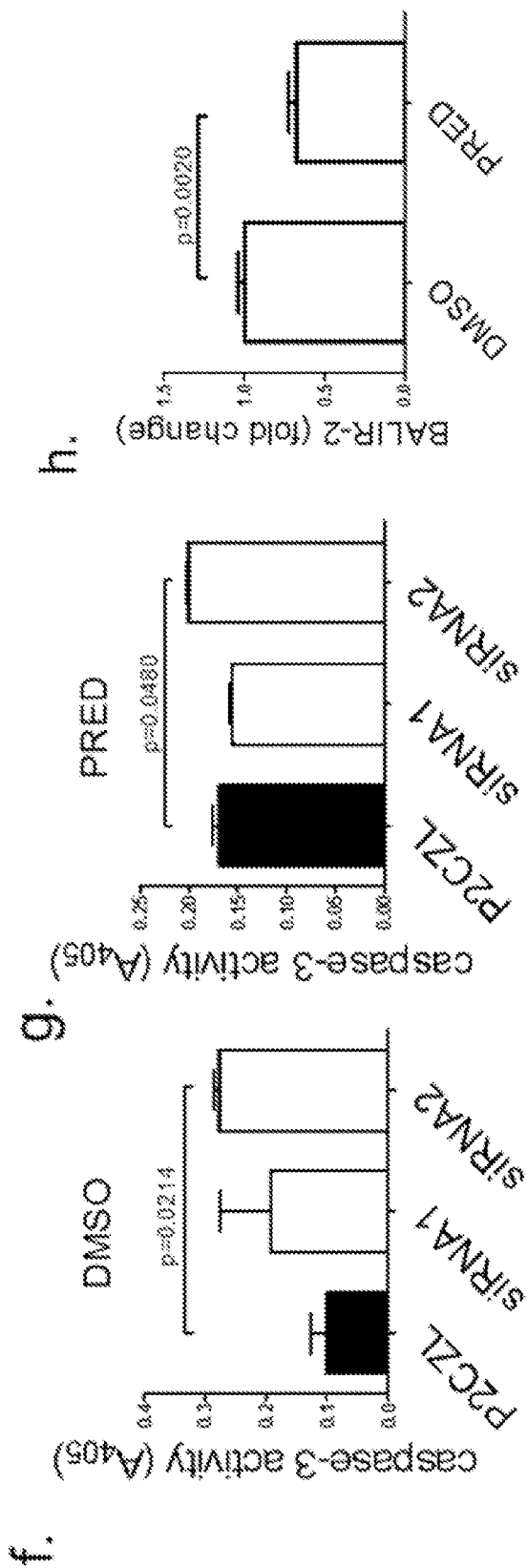
Figures 9A, 9B, 9C, 9D, 9E:
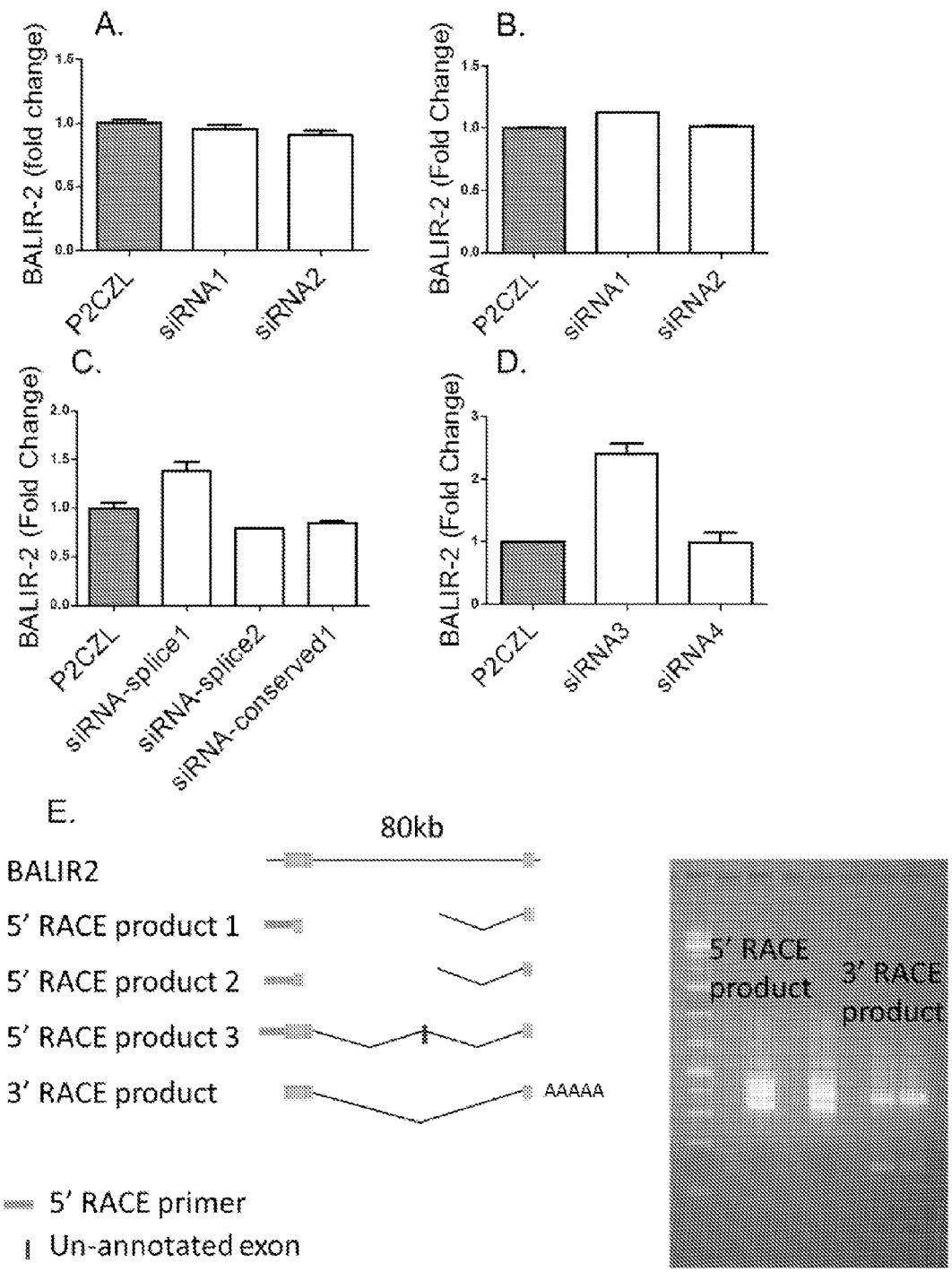
FIGS. 9A-9D—Additional siRNA against BALIR-2. siRNA that do not knock down BALIR-2 include siRNA1 and siRNA2 in NALM6 cell line (A), human-miR155-formatted siRNA1 and siRNA2 in RS411 cell line (B), siRNA against splice sites and highly conserved (down to zebrafish) region of BALIR-2 in RS411 cell line (C), and siRNA3 and siRNA4 in RS411 cell line (D).
FIG. 9E—Molecular characterization of BALIR-2. 5' RLM-RACE and 3' RLM-RACE products are aligned with the reference sequence of the BALIR-2. 5' and 3' end are identified by the presence of the 5' RLM-RACE primer and poly A sequence, respectively. Interestingly an unannotated novel exon is identified from one of the 5' RACE products.
Figures 10A, 10B, 10C, 10D, 10E, 10F:
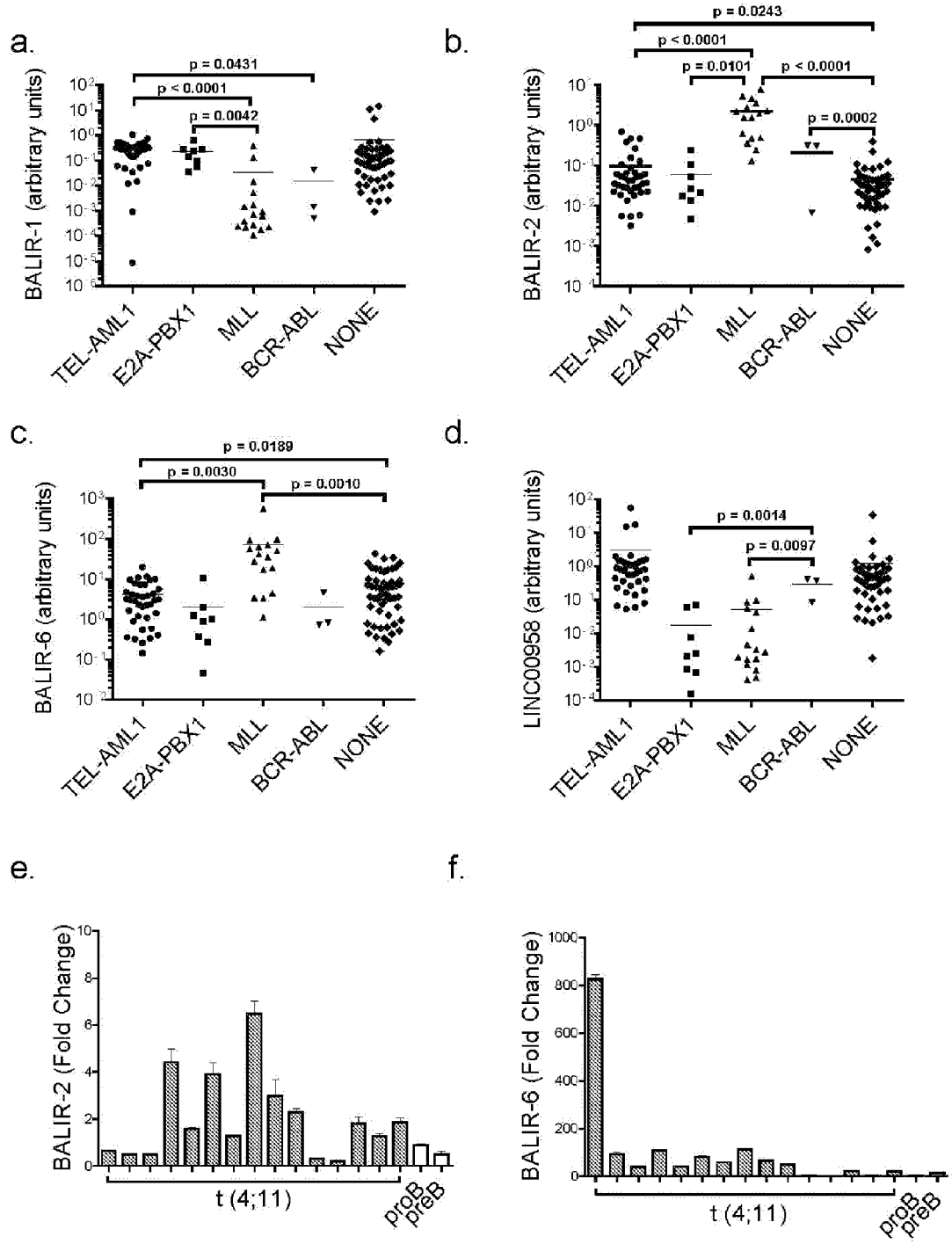
FIGS. 10A-10F—Differential lincRNA expression is confirmed by RT-qPCR. (A-D) Expression levels of BALIR-1, BALIR-2, BALIR-6 or LINC00958, respectively, normalized to Actin. For these analyses 36 samples from the set of cases used for microarray and 89 new samples were used based on the availability of good-quality RNA. RT-qPCR was performed with specific primers for these lincRNAs, showing differential expression between the three cytogenetic subtypes of B-ALL used for the initial microarray experiments and an independent cohort of clinical samples. Number of cases used in this analysis: TEL-AML1-translocated, n=38; E2A-PBX-translocated, n=8; MLL-translocated, n=16; BCR-ABL-translocated, n=3 and karyotypically normal cases, designated as none, although we did not assess all known translocations by FISH and PCR; n=53. (E-F) Expression of BALIR-2 (E) and BALIR-6 (F) in t(4;11) samples (n=15) when compared to normal human pro-B (CD34+, CD10+, CD19+) and pre-B cells (CD34-negative, CD10+, CD19+, IgM-negative). BALIR-2 expression was higher in 10/15 samples ($p \leq 0.01$) when compared to normal pro-B cells and higher in 11/15 samples ($p \leq 0.01$) when compared to normal pre-B cells. BALIR-6 expression was higher in 12/15 samples ($p \leq 0.01$) when compared to normal pro-B cells and higher in 11/15 samples ($p \leq 0.01$) when compared to normal pre-B cells.
Figures 11A, 11B, 11C, 11D:
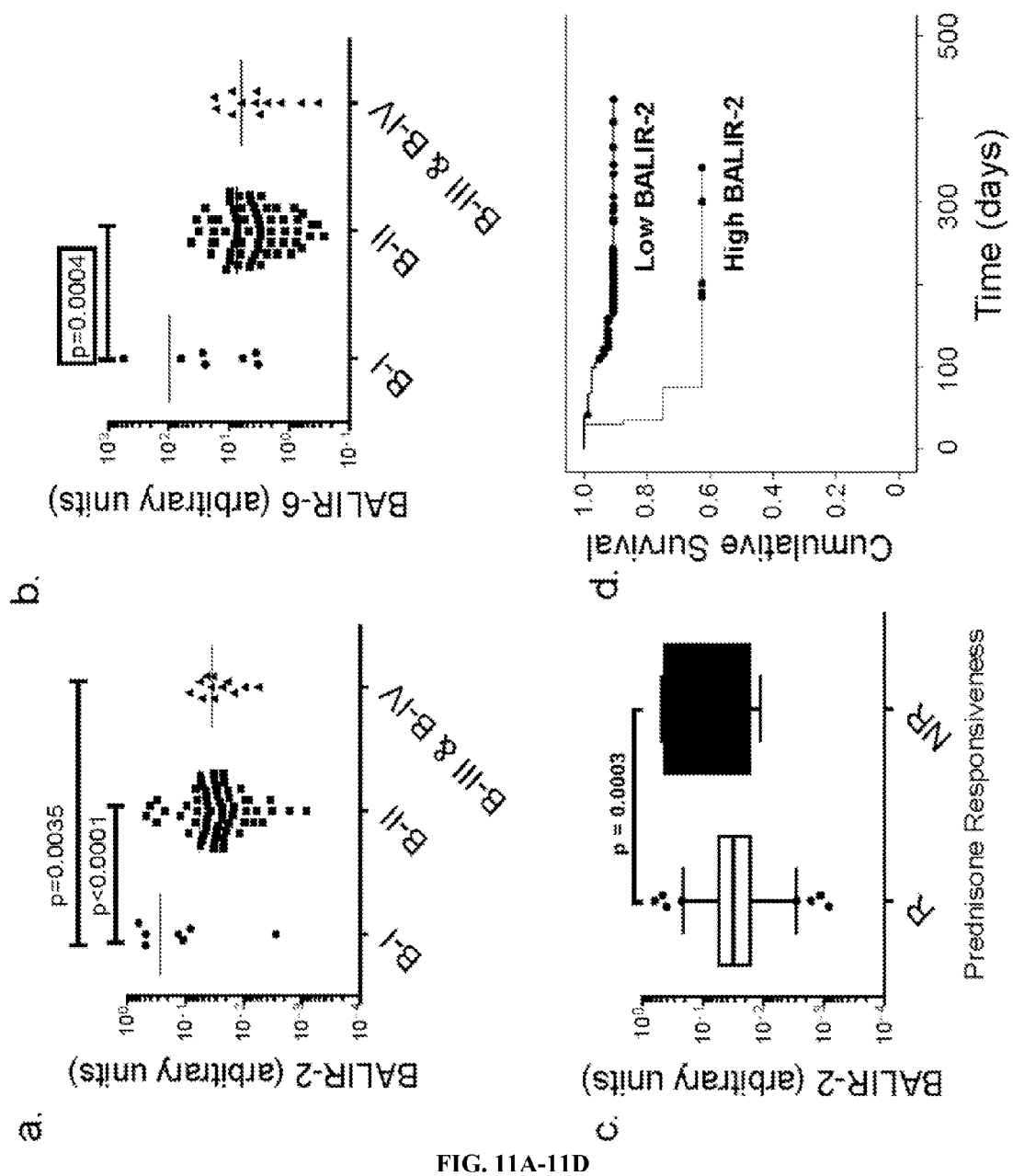
FIGS. 11A-11D—LincRNA expression correlates with clinicopathologic parameters. BALIR-2 (A) and BALIR-6 (B) expression show a significant variation based on B-ALL immunophenotype[30] (1-way ANOVA, p<0.0001 for BALIR-2 and p<0.0005 for BALIR-6). Number of cases used in this analysis: B-I, n=7; B-II, n=64; B-III and B-IV, n=12. (C) Analysis of BALIR-2 expression data and response to prednisone treatment shows that BALIR-2 expression is significantly higher in B-ALL patients that are not responsive (NR) to prednisone compared to those who do respond to Prednisone®. Number of cases used in this analysis: Responsive, n=81; Non-Responsive, n=8. (D) Kaplan Meier survival analysis for two groups of BALIR-2 shows that high BALIR-2 expression was associated with poor overall survival (overall survival (OS) high=62.5% (n=8), OS low=91.5% (n=82), log-Rank test, p=0.005). The two groups were dichotomized based on two step cluster analysis using SPSS software.
Figures 12C, 12D, 12E, 12F:
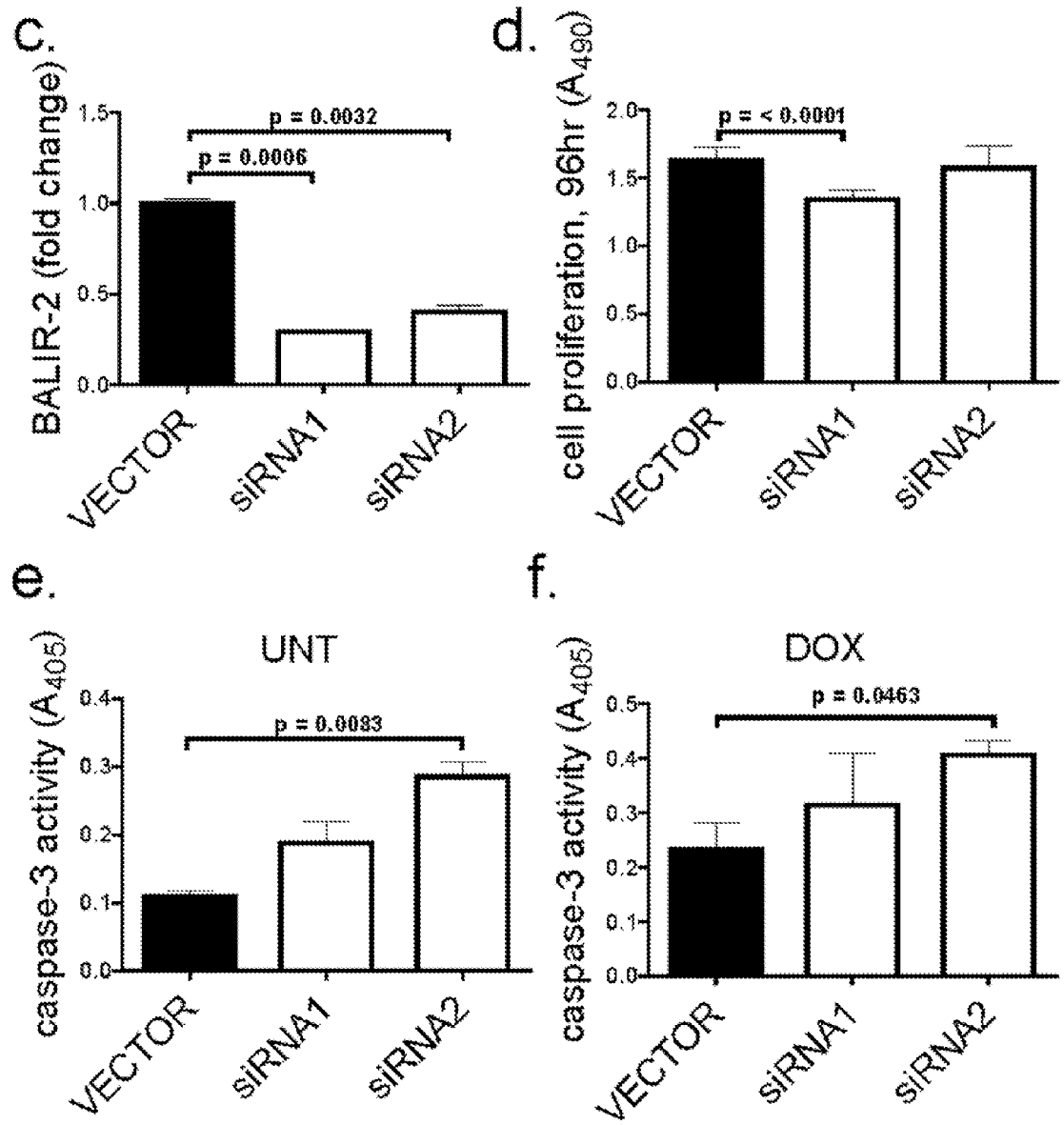
Figures 12G, 12H, 12I, 12J:
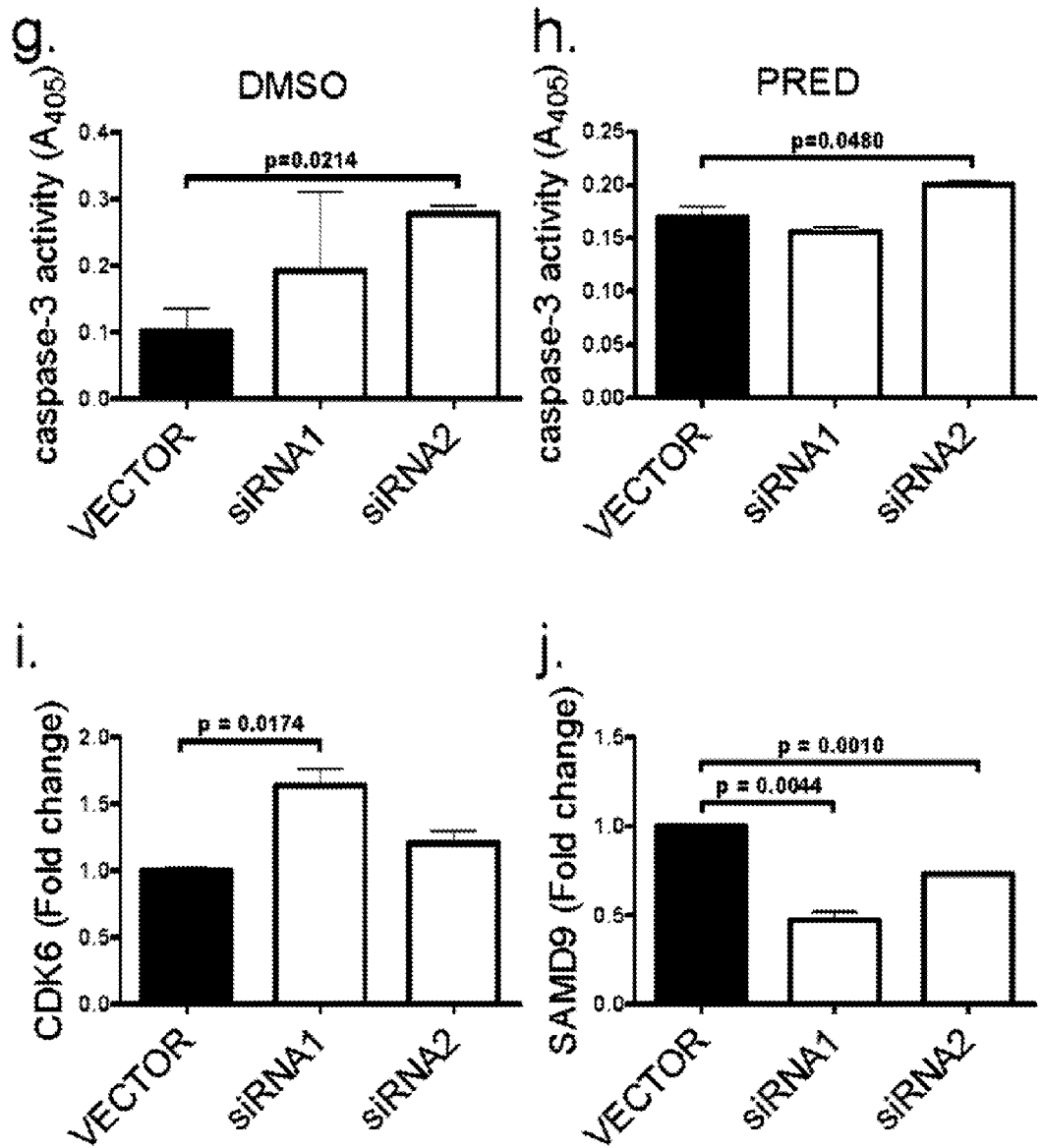

Given the correlation of BALIR-2 with overall survival and with response to prednisone treatment, we decided to investigate it further. First we characterized its chromosomal location, which is at 7q21.2. The neighboring genes of BALIR-2 are FAM133B, CDK6, and SAMD9. This block of genes is syntenic in mice and humans and is conserved in mammals. There is an mRNA that was annotated in the UCSC genome browser that is localized to this region, CB217567 (FIG. 5A). To confirm the transcript, we carried out 5'RACE and 3'RACE using RNA extracted from B-ALL cell line RS411 as the starting material. We confirmed that the 5' end of the sequence indeed matched up with the annotated mRNA; however, there appears to be an alternate splice form with an additional previously unannotated exon (FIG. 9E). 3' RACE confirmed the transcript as being relatively small, approximately 500 base pairs (see Table 1 for full-length sequence). Based on the criteria of Rinn et al, this transcript is predicted to be non-coding. The full length sequence of BALIR-2 does not have a continuous open reading frame (ORF) as predicted by the Transeq algorithm (www.ebi.ac.uk/Tools/st/emboss_transeq/). Short ORF length (<100 bp) and the absence of a translation initiation site in the predicted ORFs also indicate a low likelihood of translation (Niazi, 2012). Given the data with regards to the prednisone response in the patients, we treated RS411 and NALM6 cell lines with prednisolone (the active metabolite of prednisone). Remarkably, we found a 30-50% decrease in expression of BALIR-2 following treatment (FIG. 5H). Next, we wanted to know whether the knockdown of BALIR-2 resulted in any functional changes in the B-ALL cell lines. siRNAs designed using the stem loop structure of miR-155 and targeting BALIR-2 were cloned into a modified lentiviral vector (P2CZL) using miRNA-formatted flanking and loop sequences as we have previously described (O'Connell, 2010). The lentiviral constructs were used to transduce B-ALL cell lines and showed knockdown in the RS411 cell line (FIG. 5B). RS411 cells stably expressing siRNA against BALIR-2 showed significantly increased apoptosis as measured by caspase-3 activity at baseline and after treatment with either doxorubicin at 100 ng/mL or with prednisolone at 250 µg/mL (FIG. 5D-G). Doses were determined by titration within the range of concentrations seen in the literature (Vangipuram, 2012; Tissing, 2007). In addition, cell proliferation was reduced in cells stably transduced with BALIR-2 siRNA1, as shown in FIG. 5C. Taken together, these results support the concept that BALIR-2 plays a role in the survival of B-ALL cells and that knockdown could be utilized therapeutically.

TABLE 1

| | | | SEQ ID NO. |
|---|---|---|---|
| RT-qPCR primers | | | |
| BALIR-1 | FOW | 5' GGGACCTGGCCCCTCACCAA 3' | 1 |
| | REV | 5' AGGACTGGGCACATGGAAAAAGGT 3' | 2 |
| BALIR-2 | FOW | 5' AGCAGCAAAGCAAAGCCTGGGA 3' | 3 |
| | REV | 5' CACGGCGTGGCAGCTTTCAG 3' | 4 |
| BALIR-6 | FOW | 5' CGTGTGCTGGGGAAGGCACTG 3' | 5 |
| | REV | 5' CCAGGCTCAGAGCAACACAGGGA 3' | 6 |
| BALIR-11 | FOW | 5' GCTGGAGTGTGTGTGAGTGAACCA 3' | 7 |
| | REV | 5' GCTGAGTCTCTCCACTCAGGGGG 3' | 8 |
| ACTIN | FOW | 5' CATGTACGTTGCTATCCAGGC 3' | 9 |
| | REV | 5' CTCCTTAATGTCACGCACGAT 3' | 10 |
| LINC00958 | FOW | 5' GCTGGAGTGTGTGTGAGTGAACCA 3' | 48 |
| | REV | 5' GCTGAGTCTCTCCACTCAGGGGG 3' | 49 |
| FOS | FOW | 5' GGGGCAAGGTGGAACAGTTAT 3' | 50 |
| | REV | 5' AGGTCATCAGGGATCTTGCAG 3' | 51 |
| JUN | FOW | 5' TCCAAGTGCCGAAAAAGGAAG 3' | 52 |
| | REV | 5' CGAGTTCTGAGCTTTCAAGGT 3' | 53 |
| BIM | FOW | 5' TAAGTTCTGAGTGTGACCGAGA 3' | 54 |
| | REV | 5' GCTCTGTCTGTAGGGAGGTAGG 3' | 55 |
| CDK6 | FOW | 5' TAAGTTCTGAGTGTGACCGAGA 3' | 56 |
| | REV | 5' GCACACATCAAACAACCTGACC 3' | 57 |
| SAMD9 | FOW | 5' ATGGCAAAGCAACTTAACCTTCC 3' | 58 |
| | REV | 5' CCATTCACGTCTTGTTCAGTCA 3' | 59 |
| SGK1 | FOW | 5' CATATTATGTCGGAGCGGAATGT 3' | 60 |
| | REV | 5' TGTCAGCAGTCTGGAAAGAA 3' | 61 |
| SERPINE1 | FOW | 5' ACCGCAACGTGGTTTTCTCA 3' | 62 |
| | REV | 5' TTGAATCCCATAGCTGCTTGAAT 3' | 63 |
| Balir-2 | FOW | 5' CGCTGGTGATGTCTGTTGTC 3' | 64 |
| | REV | 5' GAGGCCTTGCTTTCACTGAG 3' | 65 |
| L32 (mouse) | FOW | 5' AAGCGAAACTGGCGGAAAC 3' | 66 |
| | REV | 5' TAACCGATGTTGGGCATCAG 3' | 67 |
| Fos | FOW | 5' CGGGTTTCAACGCCGACTA 3' | 68 |
| | REV | 5' TGGCACTAGAGACGGACAGAT 3' | 69 |
| Jun | FOW | 5' TTCCTCCAGTCCGAGAGCG 3' | 70 |
| | REV | 5' TGAGAAGGTCCGAGTTCTTGG 3' | 71 |
| Bim | FOW | 5' CGACAGTCTCAGGAGGAACC 3' | 72 |
| | REV | 5' CCTTCTCCATACCAGACGGA 3' | 73 |

TABLE 1-continued

| | | | SEQ ID NO. |
|---|---|---|---|
| Cdk6 | FOW | 5' TCTCACAGAGTAGTGCATCGT 3' | 74 |
| | REV | 5' CGAGGTAAGGGCCATCTGAAAA 3' | 75 |

Cloning Primers for P2CZL

| | | | |
|---|---|---|---|
| linker | FOW | 5' GATCCACCTCGAGTATCTAGAATGCTAGCTTGGGCCCACT 3' | 11 |
| | REV | 5' GATCAGTGGGCCCAAGCTAGCATTCTAGATACTCGAGGTG 3' | 12 |
| BamHI site | FOW | 5' ATCGGCTGAGTCGACGGATCCCTGGAGGCTTGCTGAAGGCTGTATGCTG 3' | 13 |
| XhoI site | FOW | 5' ATCGGCTGAGTCGACCTCGAGCTGGAGGCTTGCTGAAGGCTGTATGCTG 3' | 14 |
| | REV | 5' ATCGCAATTGCTCGAGTGGGCCATTTGTTCCATGTGAGTGCTAGTAACAGGCCTTGTGTC 3' | 15 |
| XbaI site | FOW | 5' ATCGGCTGAGTCGACTCTAGACTGGAGGCTTGCTGAAGGCTGTATGCTG 3' | 16 |
| | REV | 5' ATCGCAATTGTCTAGATGGGCCATTTGTTCCATGTGAGTGCTAGTAACAGGCCTTGTGTC 3' | 17 |
| NheI site | REV | 5'ATCGCAATTGGCTAGCTGGGCCATTTGTTCCATGTGAGTGCTAGTAACAGGCCTTGTGTC 3' | 18 |
| ApaI site | REV | 5'ATCGCAATTGGGGCCCTGGGCCATTTGTTCCATGTGAGTGCTAGTAACAGGCCTTGTGTC 3' | 19 |

Primers for sequencing P2CZL

| | | | |
|---|---|---|---|
| P2CZL seq 1 | FOW | 5' TGGCACCTGACCGAGCACG 3' | 20 |
| P2CZL seq 2 | FOW | 5' TGACCCGCGAGGACCGC 3' | 21 |

RACE primers

| | | | |
|---|---|---|---|
| BALIR2-3'RACE-1 | FOW | 5' AGCAGCAAAGCAAAGCCTGGGA 3' | 22 |
| BALIR2-3'RACE-2 | FOW | 5' GCAGCAAAGCAAAGCCTGGGA 3' | 23 |
| BALIR2-3'RACE-3 | FOW | 5' CATGCCAACCTAATCTGTGTTAAAATGC 3' | 24 |
| BALIR2-3'RACE-4 | FOW | 5' GCATATGAAGGTCTTGACCTGAGAAAACC 3' | 25 |
| BALIR2-5'RACE-1 | REV | 5' CACGGCGTGGCAGCTTTCAG 3' | 26 |
| BALIR2-5'RACE-2 | REV | 5' TCACGGCGTGGCAGCTTTCAG 3' | 27 |
| BALIR2-5'RACE-3 | REV | 5' GATCAATTTAAGGTAAGTGGCAGGC 3' | 28 |
| Balir-2 3'RACE-1 | FOW | 5' GGTAACCAGGGCAAGGAAATGCAA3' | 76 |
| Balir-2 3'RACE-2 | FOW | 5' GCAAACAGTAGAATCATGCCAACGT3' | 77 | miR-155 formatted siRNA oligos

| | | |
|---|---|---|
| BALIR2-siRNA1 | 5'GAAGGCTGTATGCTGAGATTAGGTTGGCATGATTCTGTTTTGGCCACTGACTGACAGAATCATCAACCTAATCTCAGGACACAAGGCCTG3' | 29/39 |
| BALIR2-siRNA2 | 5'GAAGGCTGTATGCTGTTTACTGAAATCTCCTAGGTGGTTTTGGCCACTGACTGACCACCTAGGATTTCAGTAAACAGGACACAAGGCCTG3' | 30/40 |
| BALIR2-siRNA3 | 5'GTAGGCTGTATGCTGTAAGGTAAGTGGCAGGCATTTGTTTTGGCCACTGACTGACAAATGCCTCACTTACCTTATGTATGATGCCTG3' | 31/41 |
| BALIR2-siRNA4 | 5'GTAGGCTGTATGCTGTTTCACGGTGTGGCAGCTTTCGTTTTGCCTCCAACTGAGAAAGCTGACACCGTGAAATGTATGATGCCTG3' | 32/42 |
| BALIR2-siRNA1-human155f | 5'GTAGGCTGTATGCTGAGATTAGGTTGGCATGATTCTGTTTTGGCCACTGACTGACAGAATCATCAACCTAATCTTGTATGATGCCTG3' | 33/43 |
| BALIR2-siRNA1-human155f | 5'GTAGGCTGTATGCTGTTTACTGAAATCTCCTAGGTGGTTTTGGCCACTGACTGACCACCTAGGATTTCAGTAAATGTATGATGCCTG3' | 34/44 |

TABLE 1-continued

| | | SEQ ID NO. |
|---|---|---|
| BALIR2-siRNA-splice1 | 5'GAAGGCTGTATGCTGCAGAGTCTGATTACCTGCTCCGTTTTGGCCACTGACTGACGGAG CAGGATCAGACTCTGCAGGACACAAGGCCTG3' | 35/ 45 |
| BALIR2-siRNA-splice2 | 5'GAAGGCTGTATGCTGCCAAATAGCTTGCAGTGCTGTGTTTTGGCCACTGACTGACACAG CACTAAGCTATTTGGCAGGACACAAGGCCTG3' | 36/ 46 |
| BALIR2-siRNA-conserved | 5'GAAGGCTGTATGCTGATATGCCAAATAGCTTGCAGTGTTTTGGCCACTGACTGACACTG CAAGATTTGGCATATCAGGACACAAGGCCTG3' | 37/ 47 |
| mBalir2-siRNA1 | 5'GAAGGCTGTATGCTGAAATGGTTTCCTCAGGTCAAGGTTTTGGCCACTGACTGACCTTG ACCTGGAAACCATTTCAGGACACAAGGCCTG3' | 78/ 79 |
| mBalir2-siRNA2 | 5'GAAGGCTGTATGCTGTAAGGTAAGTGGCAGGCGCTTGTTTTGGCCACTGACTGACAAGC GCCTCACTTACCTTACAGGACACAAGGCCTG3' | 80/ 81 |
| mBalir3-siRNA3 | 5'GAAGGCTGTATGCTGATTTAAGGTAAGTGGCAGGCGGTTTTGGCCACTGACTGACCGCC TGCCTTACCTTAAATCAGGACACAAGGCCTG3' | 82/ 83 |
| BALIR RACE sequences | | |
| RACE Sequence BALIR2 | 5'AGTCGCGTCGGGCCTCCCGAGGGGGCTGCGAGTGTCAGTCGGCTCTCCGCACGTGTCCG CGGCCTCGCGGAGCAGCACTGCAAGCTATTTGGCATATGAAGGTCTTGACCTGAGAAACC ATCTTGGATAACTGCAGCAAGGAAAAGGAAAAATGCAACACCTAGGAGATTTCAGTAAACA GTAGAATCATGCCAACCTAATCTGTGTTAAAATGCTTGGAATGTGGGAGCCGCTGATGATG CCTCTTGTCTGTGTGTCTGACTGAATCCTTTCTTTTCTCAGAGCAGCAAAGCAAAGCCTGG GAACCAGGCCAAATGCCTGCCACTTACCTTAAATTGATCAGCCACTTTGAGATTAAAACCC CTGAAAGCTGCCACGCCGTGAAAACAAGGCCTCCTTCACATTAAAGGCAAATTGCGACTTT GAAAAAAAAAAAAAAGAAAAAAAAAAAAAAGTACTCTGCGTTGTTACCAC3' | 38 |
| RACE Sequence mBalir2 | 5'CGCAGCAAAGCCAAGCCTGGGAACCAGGCCAAGCGCCTGCCACTTACCTTAAATTGATC AGCCACTTTGAGATTAAAACCCTGAAAGCTGCCGCTCAGTGAAAGCAAGGCCTCTTTCAC ATTAAAGGCAAATTGCGACTGTGGGTTTGCTGTGATCGCCCTCTCTCTCTCTCTCCTTT TTTCCCCCTATTTTACCCGTTTTTTTCAGTGTGGACTTTTTTCTCTCTCCTCTTTCCATTT ATGCTTCCATGTAGAAGCCAATAGTTATAGCATCTTAGCCAAGCATTCATTAAGGTTTATA AGAACAAAATTTATGGTTATTTAGAAGTTGGCACAGAGATCAATTGTTGCTAGAAAAAAAA AAGAAAGAAA3' | 84 |
| Additional BALIR sequences | | |
| BALIR-1 mRNA | GCCTAGTAGAGATCTGGAGCCAGAAGCCCAGAGACAGCCGAGTGCGCCGTGCGGTCTCCGG ACGCTCGCTGCTCAGCCCGATCCCCGCCAACTGTGCAGGCGGCTGACCCGCAGCGGCAGCG GCAGCAGCGAGGACTCGAGCGCTGGCTGCAGCGACACCATGGATCTCTCCTTTATGGCCGC GCAGCTGCCCATGATGGGGGAGCTTTCATGGACTCGCCCAACGAGGACTTCAGCACCGAG TACTCCCTGTTTAACTCCTCTGCCAATGTCCACGCGGCTGCCAATGGCCAGGGCCAGCGG AAGATCCTCCTCGGTCCTCCAACGACGCCGTCTTGCTATGGATTGCCATCATAGCTACGCT GGGGAACATCGTGGTGGTGGGCGTGGTGTATGCCTTCACCTTCTGAGGACGGCACACCCTG CACCACCATGGGGTGAGGCTTGGCACGTAGCTCTGACTTGCTGTCGGCCTTTGGCTTCTCC TGTGTTCTAGAACCAGGAGTTTTGACCAGGGGCGGCGGCCGTCCTTCTGGAATTTCTCCCC AGCAGCCCTGATTTCAAATATCCCATGTTGTGGTCAAGCTGAGTCAGAAGACATGGAAGTA TGGGCCTCCTGCCCCTAGAGGCATGACGGGGCAAGGCCTTCAGAGGGCAGATTGGGGATCC TTGAAACTACATTCCAGGAACATGGGACCAGATGAGCAGCTAGTTAAGTTTAAAACATAG ACATGATTTGATGATCGCTTGCTGGTGGTAAATAATCACTCGTGTGACTTGTTTTTATGCA AACTTATCGAACCTAGGGCGTGGGGTGCTGGGCAAGAGCAGCCCTCAGAACTTCAGTGTT CCTGACCCAATTCTGGTTTCACATTCAGTCCCTTGGCCATCTAGTAGGGCATTGGATGTT CCTAGTTTGACTTTGAAATGGCACCTTTGCCACCAGACACCTGGTCCCTTCCAAGACCCAA GTGCATTGGGAGACCCAGGGATGGGGGTTACTGGTAATAGGTGGGGTTTCTGGGGGTGTT GTTGGTGGTTTTTATCTCCTGGTCGGACTTTCTCTTCTTTTTAAGAAGAGGAGAGGATGTC TTTAAGAGCTAGATGTGCCAGGCAGTGGACTCTTCAGGCCACCCACGTGAGAATGCTGTTT CTTCTCTGAGGAATCGTGGAATTTTAAAGATGAACAAGATTCACATCCACTGAATTATTCA ACGGATGGGTCAGAAAGGGGGTGATTTGCCTGTGGTCACCAGGCAGGTTTGTGGAGGAGT CGGAACAGAAAGATGTGTCCTCACTCTCAGCTCACTGAGCTCTCTGCCCCAACTAAGCACT TCCCTGAGGAGGTTGCTGAGAAGCTGCCCTCAGGAGAATGTCCAGGCATCTTGAAGGTGGG TGCGAGATTGGCAGGCTGCTCAGATACCCGTCCTTTACATTCAGTGTGGATACCGTGCATT CTCCTGAAGCTGTGAAAGTGCTTCTGCCCAAGCCACTTCCTTAAATTCTGAAATATCAGCA TCTGGGGTCCTGGCAAGCAAGGAAGCTTCCAAGTAAAAACCAGAGAGAAGGGCACACTTTT CTTCTTCATTAGGGAATCTTATTGCACAGGAACCACCCCACCCCCCACCCCCACACCTT CCCAAGGCAGCATCCCAGTGCAGATAGAGTGGGAAAGGTCCCAGAAGGGGGCTCACTCACC TCTAGGCCCAGAGAGGCTTTCTCCTCACTTTATACACTGCAAAAACAGAAGAATTGTGTCA ATAACACCCTCTGTAGTGGAGAAACTTAAAAAGCTGGTTAGGAAGCTCGTGTATATTTA GAGACAATTACAAGAAAGCTGGACTTGCCGCTGTGGTCTCAGGAGAAATGAGTGTTCTTGA TGACAGGCAAAGGGACATCTTAGTTGTCCAGAAGCGGCACTCTTCCCTGGAAGCCGCCATG TTAATAGGATTACTAGCCTGGCTCCAGACAGTGCCTGCTCATGGCTGCAGTTCTTACCGA TCACATCTGTCACTGCCACCGTATATCATCTGCCAGTGCATCAGCTTAAGGGGAGGTCACG | 85 |

TABLE 1-continued

| | SEQ ID NO. |
|---|---|
| AGTGCAAAAGAACCTGACCCTTGACAATGAGGGAGAAGGGACATGGACCACCTGTCTGGAA | |
| TTCCTGGAATCACTGGCAGGGTGGAGGCTGGGCTGGGGAGTTAGCCGCGGTGTGCGTGAAT | |
| GGCTCTGTCTCCAGCAAGTCTCTCTCCATCAAACCCCAGGTCTGCCCCATAAGCAAGATCT | |
| TTAACAGATGGATGTCTCCATGAGAAAACCCAAGGCGAGAAGCCCAGAGCCATGGCGGGGT | |
| TGCTTGACGTCCTCATGGAGTCACTCTGCCCCACATGCTCAAATCTTCCCTCTGGCCCCAC | |
| ATCCCTAGGAGGGCCTGACCCCTGTAAAGATACAGGAGGCAGCTCCCTGGCCTCCAAATGG | |
| CCCATGGAGATGGCAGTCGGGAGACAGGGTTCTGTGTTTGCTGCGGTGAAGGGAGGAGAAG | |
| GCAGGAGGAAAAAGGATGGCTTCTAGCCCTGAAGAGGACTCCAGCATCCCAGGCACCCGGT | |
| GCTTCTGGCTGCAGTTTTCCCTATGGAGGCCCCTCAGCCTCCAGCCCTAACATAAATGTCG | |
| GTTAAATTCAGTTTTCAAGCCTCTCTCCCTTTTCAGTGTCAGAGCAGTAGATGGTCCAGGG | |
| CATTGGAGGCCTCGACCACTCTGCATTGCAGATTACAGTGACTTCCTCGGGGTTGCCCCAT | |
| CTTGGTCTCCTGTGGTTTCTTCATCAGCTTTTTTTTACCAGCATCTCTCAAATAACAATG | |
| AAGATAGATATGCCCATTAGTGTCTGATTAAGGAGCAAAGGCTGGATTTCTGGCCACAGCG | |
| AGCTGCACTCTCCCTCCTGCCTCAGCCGGGGTCCGTCTTAGCAGTTTGGAAAGGGGAAAAA | |
| GATGCCGGTCCTCACTGCTTAAGTTTTGTGTCCAGGTGCCACTAGACTTGCATGCACACTA | |
| ACTCCTTACAATCACCACACAGCATCATCGCCCCAGTGCACAGATGAGGAACCAGAGGCTC | |
| AGAGGAGTGAAGTTGCCTTCCTGAGGTCACACAGCATGAAAGTGATGAGCTAGGATTTGAA | |
| TCTGGGAAGTTGGGCTCTAGAGCCAGACTGTACTGCCTTCTGCCACACTGTACTGCCTTCT | |
| GTGACTGGGTGGCACCTCCAGGGCACATTTACACAAGGCCCTGAATCTGCAGAGGCTGTTT | |
| CTCAAGATGCCCGTCATGGTGTGGCCTGGGCCAGCTCTGGCTTCCACAGGTCCCTGACTGT | |
| CCTCAGAGTGGAACATGCTCAACCTCCCGCCCACTGCTCTCTCTGCCCAGATTTCAGGG | |
| GTGCCGGTCCCCAAGGCCTGCCCCCTTCTTTAAGACTGAACTCAAGTCTCCTTGGAAGGCC | |
| CCGGTGAAGCTCCCAGAGACTGGTTTTCTTGGGATGCAGGCAGAAGGGGACCCTCCCTGGC | |
| CAACACCCAGGAGCCCAGCAGAAGCACCCACACGTAGAAAGAGGCTCACTACAGCCAGAAG | |
| TGCAGAGTCAGAGTCCTGGGACCATCTTGTTCTGCAAGGTGACCCCAGGCTCCCCAGGACA | |
| GGGGAGAGGGATCGTCCTCATTCAGACTCTAGCTGGGGCCTCTGTACTGGCTTCTCCTTGG | |
| GTGGGGTTGCCTGTTACATAGCTGTGCCTCAGAGAAAGGGTCCTGCATTTTCTGGAATGTT | |
| CTCTGTGCTTACCCCTCTGTGTGCCCCTCCATTGCTCCTCTACAAGCAATTAGGTGATTCA | |
| AAAGAGCAACTTAGGCTGGGTGCAGTGACTCACACCCGTAATCCCGGCACTTTGGGAGGCC | |
| GAGGCGGGCAGGGACAGGAGTTCAAGACCAGCCTGGCCAACATGGTGAAACCCTGTCTCTA | |
| CAAAAAATACAAAAATTAACCAGACATTGTGGCATGTGCCTGTAATCCCAGCTACTCAGGA | |
| GGCTGACACAGGAGAATTGCTTGAACCAGGAGGCGGAGGCTGCAGTGAGCTGAGATTGTGC | |
| CACTGCACTCCAGCCTGGGCAACACAACGAGACTCTGTCTCAAAAAAAAAAAAAAGAAAAG | |
| AAAAAAAAAAAGAGCAACTTACTGCTTTGTGAGGTTGTGAGTGGCCACCACTGAAGGTCTTT | |
| GAGAAGAGGCCAGACGCCGCTGTAGCCAGGCCTGTCTTAAGAGGACTTGTGCTTCCAGGGA | |
| CCCAGGCAGGATGATGGCGCAGCTCTTCCTACTCCAAGCCAACGCTGTCCTTCCCCTTTCC | |
| CATGAAATCAAGGTCAAGAGGCAAATAAGACTCCCTGCTCCACTCTACCCCCCAGAGAGAA | |
| ATGATTCTCGCTCCTTTCAGATCCCCCAGGATCTGAGGGAGAAAGGATGGGAGGAGGGGCA | |
| GCAGCATTTCGCTGGAAAGGCAGCAGATGCTTTTCCAGCCCCGGTTCAGCTGGAAGGCTTG | |
| GAGGCCGGCCAGACCACTCTGGCGTCTCCTGAAGTGGGTCCCTGGAGACCGAAGAGGCTCA | |
| GTGGAGTCTGTCTGTTGTCAGCACTGCTGCCTGATCCCTGCAAGACAAATGGCACTTTCCT | |
| TCTTCAGAAGCATCATCTGCCTTCATTATTAGCAGTAATATTATTCCCAGTTATTATTCTT | |
| ACCGGTGCCAGTTTTGCACATCTTTTTGTTGCTCTATTTGTGTCTCATTTACTTCTCAAAT | |
| TGCCCCTGGGGGCAGGAATGAGGATGCAGAGAGATGCACGTTAATTACTGTCGCATTTTTC | |
| TGTGGAGAAAACTGAGGCCAGGGCTGAACGCTCACAGCTAAGGAGCTGTGATTCAGACCCA | |
| GTTCTGTCAGCTCTAGAGGCACCCTGCATCATGCCCACCAGGGTGATCCCCCTGGGATGGA | |
| CCATCTCGGGATATGAGGCCTCGGAGGCTGGGGTTGAGATTTGGTCCTGAAGAGCTTATAG | |
| CCAGATTGCCACATTCAAGTGTAAGTCCAGGAAAGGGGCAGGCGGCAGTGCACAGGGATTT | |
| ATCAGTTCCAGAACCTCACAGTGATAAGAGGCTTTAGAGAGCATCTAATCGAGACCTTTAA | |
| TTTTTCGGGGAGAGCAGCTGAGGCCGTGTGGAAAATTAGTGGAGAGCTGACAAGTGTCTGG | |
| GCTCCTGGCCCAGGGGTCCGTGGTCCAGCACGTTGTGCGTTCAGTGGGAAGCAAAGGGCTT | |
| GCCCGGGATTACCTGCCCCAGCCCCGAGGTGGGTTGTGCTCCCTGCAGCTGCCATCGGCCC | |
| GCTTTGCTTCGTCCTGGCAGATGCCCAGTGATTGTCCCCGAGCAAGTGCCAGGGTTGGGCT | |
| GAGCTGCTATGCAGGGAGGCCCAGGGAGTTCTGCTCAGGGAGCCAAAGGGAACAGCCAGA | |
| TCCTGAATGTTCTATGTTCACCTGCCCCAGCCCCACCCACCCTGGCCCACTCCACAGGCCC | |
| CTGACCATGGTCACTCACGGAGAGGGATGGAGGAGAAGGTGGTTGAACTGAGTACTGAGAA | |
| CCCAGAGGACAGAGCCCACAGCTTCCAAGCAGGAAAAGGGACCTCTCTGAAAAATCTGGAT | |
| AACCAGAATTATCACAGCACCCTCTCATTCCCAGCGCGTCCTTCTGAGCTCAGACCTTGAG | |
| CATTTACTGGGTTTCTTTTTGAGGAAGAGGGAAAGTGACAAAGGACAAAACAATGCAAATC | |
| TTCATGACTGAAGACGATCAAAGACTCCCTGGAGCGAGAAAACAGTTACTGCCAGAAGCAG | |
| AATGGAAGAGCCAAAAAGTACAAAATGGACGCCATAAATTCTGAAATAAAAGTGTATGA | |
| TGTGTTCTGAGTCACTGTAGAAGTCATGCATTTATTATCAAGATAGAAAAGAGCAGAGAAT | |
| GACGTGGACATTGGTCCTCGGAGAGGCTGCATAGGTGGTGCGGTCCCCGGGGGATTCTGGA | |
| TGCTGGTCTTTTGACCGTGGCGGCAGCCTCGCGCCTGCCCGGATGGCTCCATCCAGACATT | |
| TGGCAAGGCTGTCATCTGCTCTTGGGTCCTTTTTCAAGCTGATTTCCTGCCTCCCCAAGAG | |
| GAGGTTTGAGCCCCATTCTGCCTTGGAAATAAATCCTGACAGATGTGCACAGCATATTTGC | |
| AGGGAATTTGCAGGCCTCGATTATTGGGGAATCAGAGCCCATTCCACACCGAGCCCCATC | |
| CACGTGGCTGAGCAACACCCCTGTGTCCCCTGTATCTGTCTCACTGGCTGTCTTTCTGCCA | |
| GTTTCTTAAAGAACCACACCATTACTGCATTTGCCGTTCGAAGCGTTGTCCCAACAATGCA | |
| GATGGTTCTGACAAGGGTCTATATGCTGGCAGAAGGGAGCTTCCAACCTTTTAACTTGAGG | |
| AAAATGAATCTCTGACAGGCTTGAGAGTGTTGCCAGGTGGAGCTTTTCAGGAGACAGGGGT | |
| CTTGAGCCCAGGACACCTAACTATCGAGTTTTCACTAGGAGACTTAGTGGTGGCTTTCATG | |
| AGGCCAGTCGTTCTCAAGGAAGGGCTGGGGGCATCAGCAATGTCTGGAGACATTTTTGAT | |
| TCTCACAGCTTGGTGGGGACTGCTATTGGTATCTCATGGGTGGAGGCCAGGGATGCCACCG | |
| AACATCCTACAATGCACAGGGCAGCCCCCCACAAATAAGAATTATCCAGCCCCAAATGCC | |
| AATAGTGCCGAGGTCAGGGGACCCTGTGCTGGCCATCCTATCTCTGATTCTGAAACTATGC | |

TABLE 1-continued

| | | SEQ ID NO. |
|---|---|---|
| | ATGCTTTCCACTTTTCCCCATTTGTGAGTCATTGAGTAAATTAAAGCTCTTCTGAGCAGCA GCAGTGATCATGGTCACTGCCCTGCGTTCAAATAATGCGAGCTGAGGACAGTGATCTGCAA CTCCCAGCATGTCATGTGGTCTCTTAGAAATCCATGTGACTGTTTCCACCATCTTGGGCAT TTGTGGGGACCCCCAGACTGGAGGGAGAAAGCCCTACAAAGTGGATGGGAGTGTGGGGCTG AACTTTTCCCTACCCTTAACTTTGTGTCTCTGGGACCTCCAGGGACCTGGCCCCTCACCAA TGCATATGAAGAGTATGCTTGGGGAAGAGCTTAGGAATGGGGTGGGCATGGGAGTGCTGGG TAGCAGCCTTTGAGCAAATCTGCATCTTCTCTTATTTCTGACCTTTTTCCATGTGCCCAGT CCTATTTCTGCCAGTTGAAGGCATACTAATATTCTTTATACTATTTAATCTTTTGCAGAAA CCTTACTATTATAACTTGCTACTCTCCAGATACCAATTCTTCATGCCGAGAGCATCGGAAA TGTTTTTGTGTCTTACTGATGTTTTCATGATCAACTTGTAATGTAAGCAGTTGACTTCATA AAAGGTATTTTAACTATTCTTGGAGTCCTTTGCTACCCAAGCACCTGGTTTCACCATGCGA TCACTGACTTCTCTACAGTGAAGACTCTTTCTTAATAAAGGATTTCGCTGTGCTCTTTTGA TTAAAAATATCTAACCTTAAAAGACGT | |
| BALIR-6 Isoform 1 | CCACGCGTCCGGGACTGAGCACTGGGAGACTCCAATGGGGAGAAGGGGAGGAACAAGCAAA AAGATGGAGAAAAAGCTACCACCAGTGACCTAGGAGAACCAGGGGGCTGGCATCCTGCAGC CACATGCACATGGAAGATCACTTTGATTGCCATGTGGAGAGTGAACTGTGGGAGGACCCCA GTGGAGGCAGGAAGACTAAACCAGAAGACAGTCACCGTAGTCCAGATAAGAGATGCATATG TTATCAATCGCCATGTGAAGAAGATGCTTGCTTCCCCTTTGCCTTCTGCCATGATTGTGAG TTTCGCGAGGCCTCCACAGCCATGCTTCCTGTACTGCAGAACTGTCTTCGATTAGATATTA CTTCTTCTGAACAATCTTCCTTGATGACCCAGCTACTTTACATCTTCTGGATGGAATCCTC TCTTTGCTCTAATGGCATGGTGTGCAGAAGTCAGCTGTGAAAAGGAGGAATGAAAGCAAGT GAAGGATGCCCTTCATAAGGAACAAGCGATCTCTCTAAAACCAATCCTAGAGTATGGCTTC AGATTCTGCTCCCATTTCTCAATGATTATGAGTTTTGTGCCACATCTTCTCCCCCTTTATC CCTACAATATTTGCATTTCATGTTTTTATTCTCTTACTGCCTGAGCAATTTGAAACTCTCA TATTTAGGCAATTCCCAGATCTCGTTCTTAAAGCATTGTGATTCCCTTTCAGCTTTTCAGA GGCACGTGTGCTGGGAAGGCACTGAGTCCTCCCTGTCAATCCAATTTGTGATAAGGATTT CCCCAGGTGCACCCATTCCATAGTCCCTGTGTTGCTCTGAGCCTGGTTGGCATCCTTTTGG GAAGCATTTGTATTGCTTTTTCATCTCAGAAAAGATACTCTAGTCACAAACCAGTCATCTG CCTGTTAAGCTGTATTTAGAACAAATCACTCCGAAGCAAAACAACGATGACAACAACAAAA GAGCCACACTTATTTCTTTCTAGACTTTTAACAAAATGTTTGATGTTGTGGAGATTTCCAA ACAATTAATGTGAAATTGGGTACTGTTGTTCACATGATTTATTTACCATATATAGAGAATT CAGCTGGAGTGCTACTGTCAATGATGCTCCCAATGAAATTTCAGCAGAGAGTTGGAAAATC AGCAAATTGTTTATTTCAAAGAGGAATTACATTTTCAAAGGATAAAAGTTAATAGGAGTC ATAGTGCTCAAAAACCACACGATATAGGAAAACCTACCCCACTCCACCAAAGGGCACATCT TGCTTTGAACACTTGATTTCATATTAACAGTTCATGAGTTATTCAAAGCAGGGGAATCCCT GCAGGTTGGGAAATATCCTAGTGCTTTTCATAGCCTTCCATGTCATGGATCAGGGACACAC ACTTGTGCACATGTGTGCACAGACACAAAACAGAGAGAATGCTTAACAGGAGCACATTTTA CAAAAGTGAGATCCCAGGCCTGGAAAATCCCAAACTCTTATAAATTTTACAAATCCAAAAT GGAATATTCAAAAAGAACTCAACCTGTTTCTCTTGAGTAACTTTTCAGACTCTCATTACAG GCCCCATGAGGTCAGTCAGATTTCTGTTCTACAGGATACTGCAAAAAGAGACCAGAAATTT AAAAAGGAGTGATGGTACCACACAAAATAGTAAAAATGAAATAGGAAGGTGTGAAGTTAG ATCCTTGATTTATGTGTGGAAAGCTAGTGCCAAGAATATTGTTATGGGCCTGGCTCCTAGA GGCAAGATTTGTTAGCAAACTGTCTCTAAATATTTATGCTCAGCTAAATAATTGCTAAATA ATTCCGGATCCCAGCTGGAAATCTAGGATCAGGACTAGCCTAAATTAGTAGATCTATGTGA TAGTATATTGGTATTTTATCCAGAAAGTACTTGCTCAATGATAGTTCAACTTCAGCATAT AATTCATATACTTTTTATAAAAGCCTTTTCATGGCATTACATAGAAGGCCTTTCCTTGGAAA TATTTCCATAAAATAAACAAAGCACTTAAATCAGTCCATTCAATAGCATTTGTTTTAGGAT TATTAAAGAAATACAGAGTTTTGACTTCCGCAGTGTGCTAACATGGATTATTCTTTCATTT GCTGATCCTTGTATGTGCAGTAGGATGTTGAAAGTGGGGGTGGTGGCAGCATATTTCTACA TCACCTTGGACTTTACCTTTCTGAGAATCAACATAGGTTTCTAACTTTTTTTATGGCCCTG ACTGGTGCTTCAGTAAACCCACGAATAAAAGCAGTACTCCAATCTGCAGAGACTCTAGAAG AAAATACTTTCTATGAACC | 86 |
| BALIR-6 Isoform 2 | TTTCTTCATACTATCCAGAGCTCCAAACTTTGTAGGAAGCCAGAAGCGTCTCCTTTGTTGA ACAGTGCCAAAATAGCAGCTCTATCCTTTCCTCTCCTCTTTCTGATTCCAGTCAATATG TGTTATGGAGTCTGTGGTCTCCACAAGGCCTTGGGATAGGCATCCAAAGGAAGATCACTTT GATTGCCATGTGGAGAGTGAACTGTGGGAGGACCCCAGTGGAGGCAGGAAGACTAAACCAG AAGACAGTCACAGTAGTCCAGATAAGAGATGCATATGTTATCAATCGCCATGTGAAGAAGA TGCTTGCTTCCCCTTTGCCTTCTGCCATGATTGTGAGTTTCGCGAGGCCTCCACAGCCATG CTTCCTGTACTGCAGAACTGTGAGTCAATTAAACCTCTTTTCTTCATAAATTACCCAGTCT CTGGTAGTTCTTTATAGCAGTGCAAGATGGACTAATACACCACCTAAGTGATGTATTTGTT GCTCCAGCTCTATATATACCTAATTTGTACATCACCTGGGACCTTGCTTTTCTTTGAGTTA AATGATTTTATATGTTAACTACTCTACTTTAATGATCACAATTTATCATATACTTTTTCAG CATCTCAATAAAAGAAATTTTTTCGAAA | 87 |
| BALIR-6 Isoform 3 | CTTTCTTCATACTATCCAGAGCTCCAAACTTTGTAGGAAGCCAGAAGCGTCTCCTTTGTTG AACAGTGCCAAAATAGCAGCTCTGAAGATCACTTTGATTGCCATGTGGAGAGTGAACTGTG GGAGGACCCCAGTGGAGGCAGGAAGACTAAACCAGAAGACAGTCACAGTAGTCCAGATAAG AGATGCATATGTTATCAATCGCCATGTGAAGAAGATGCTTGCTTCCCCTTTGCCTTCTGCC ATGATTGTGAGTTTCGCGAGGCCTCCACAGCCATGCTTCCTGTACTGCAGAACTGTGAGTC AATTAAACCTCTTTTCTTCATAAATTACCCAGTCTCTGGTAGTTCTTTATAGCAGTGCAAG ATGGACTAATACACCACCTAAGTGATGTATTTGTTGCTCCAGCTCTATATATACCTAATTT GTACATCACCTGGGACCTTGCTTTTCTTTGAGTTAAATGATTTTATATGTTAACTACTCTA CTTTAATGATCACAATTTATCATATACTTTTTCAGCATCTCAATAAAGAAATTTTTTCGA AA | 88 |

TABLE 1-continued

| | | SEQ ID NO. |
|---|---|---|
| BALIR-11 mRNA | CTCTCTCTCTCTCCTGCTGCATTGTGAAGAAACTGCTTGCTTCCCTCTCACCCTCTGCA<br>GTTTCCTGAGGCCTCCCCAGCCATGCGGAACGCTGTAGACCAAGACCTGGAATTAACACAT<br>CAGAAGATTCTATGGGGAAACCCATTTAAAAATAGGATGCATTTTTTTCTTTTCTGCACAG<br>GGAGAAAGTTTAAGCTCTCCTCACTATGAGTTTTCAAGTATAAAAGACTTTTTCTTCCACG<br>ATTTTGAGAACAACTGAGGACTCTTGTGACCAGGACAACAGGGAAGCTTGCAGCAAGATAG<br>CTCCAGGTTGGATTCATGCTTCGCACCCCAAGGGCTGCCAGCCAGAGAGGAGGAGAAGCAA<br>TCACTCCTGCAGTTTCTGAACACTACACAGACGCCAGGTAGCTTCTTCAGGAGAACAGCCC<br>TCTGAGGAGGCAGGAAGAGGAGGCTTATCTTTCAGCAGCCGGAGCTGCTGAGATCTCTGGG<br>CAGATTAAGCTCTCTCTAATGGATGGGCTCCAGCCTGGCACATTCAGTGGAGAGGGATCCA<br>CTCATCCATCATCAACATAATATGGTCCTCCCTGCACTTCACAGTGTCCTCTTGCTATTGA<br>AAAGGCTTTTTTGCCTTCTCAAGTTTCTTTGTCAACAGTCTACAGGAAGAAGCTCAGGCCG<br>CCACCGGCAGAGGTGAATGCAAGCTCACGTTTTATTTCTGACTGCTTAATCATTGCCTCGA<br>TCACTGCTCAAGCTCTGCCTTTGTTTCCAAAGGTTACCTGTGGGAAAACTTCTTTTTCTAT<br>GCTGAAATTAATAGGGAGGCAAAGATGAGTCCACTGATAAGCAGAGCCTTAAAACTCACAT<br>AGAGAAACAACTTTGCTGGAGTGTGTGTGAGTGAACCACTAAGGAATCAGATAGTGTGATG<br>GCAGTTATCATTGCAGGTTAAGACATTTCTACAAATATTTCGACATCTCCATATACTCACT<br>CCTTTCCCCCCTGAGTGGAGAGACTCAGCTACCCAGAGAGGAAGCTCAAAAAAAACAGAAG<br>CTTCAAACAAACAACCAACCAAAAAAAAAAAAAAACTGTGGGTTCATCAGAGGTGGTAGGGA<br>AGACAAAACATGGGAGGAGCAGCTGGGCACGGTGGCTCAAGCCTGTAATCCCAGCACTTT<br>GCGAGGCTGAGGTGGGTGGATCACCTGAGGTCAGGAGTTCGAGACCAGCCTGGCCAACATG<br>GTGAAACCCCATCTCTACTAAAAATACAAAAAATTAGCCGGGCGTTGTGGTACGCACCTGT<br>AATCCCAGCTACTCCGGAGGCTGAGGCAGCAGAATCGCTTGAACCCAGGAGGCAGAGGTTG<br>CAACGAGCCAAGATCGCACCATTGCACTCCAGCCTGGGCAACAAGAGCGAAACTCCATCTA<br>AAAAAAACAAACAAGCAAACAAACAAAAAACACGGGAGGAGCAATAAAAAGGAATCCATGC<br>TTTGATTTTTTTTTTAGTGAGAGGAAGGGAAGGCTGCTGCCTCTCACTTCTCCCTGTTTT<br>GTTGTTCTTTTAAGTAGCATGTGTCACTCTGT | 89 |
| BALIR-11 Potential isoform | CCTTTGTTTCCAAAGGTTACCTGTGGGAAAACTTCTTTTTCTATGCTGAAATTAATAGGGA<br>GGCAAAGATGAGTCCACTGATAAGCAGAGCCTTAAAACTCACATAGAGAAACAACTTTGCT<br>GGAGTGTGTGTGAGTGAACCACTAAGGAATCAGATAGTGTGATGGCAGTTATCATTGCAGG<br>TTAAGACATTTCTACAAATATTTCGACATCTCCATATACTCACTCCTTTCCCCCCTGAGTG<br>GAGAGACTCAGCTACCCAGAGAGGAAGCTCAAAAAAAACAGAAGCTTCAAACAAACAACCA<br>ACCAAAAAAAAAAAAAAC | 90 |

BALIR-2 Regulates Apoptosis by Modulating the Glucocorticoid Receptor Signaling Pathway.

Figures 13A, 13B, 13C:
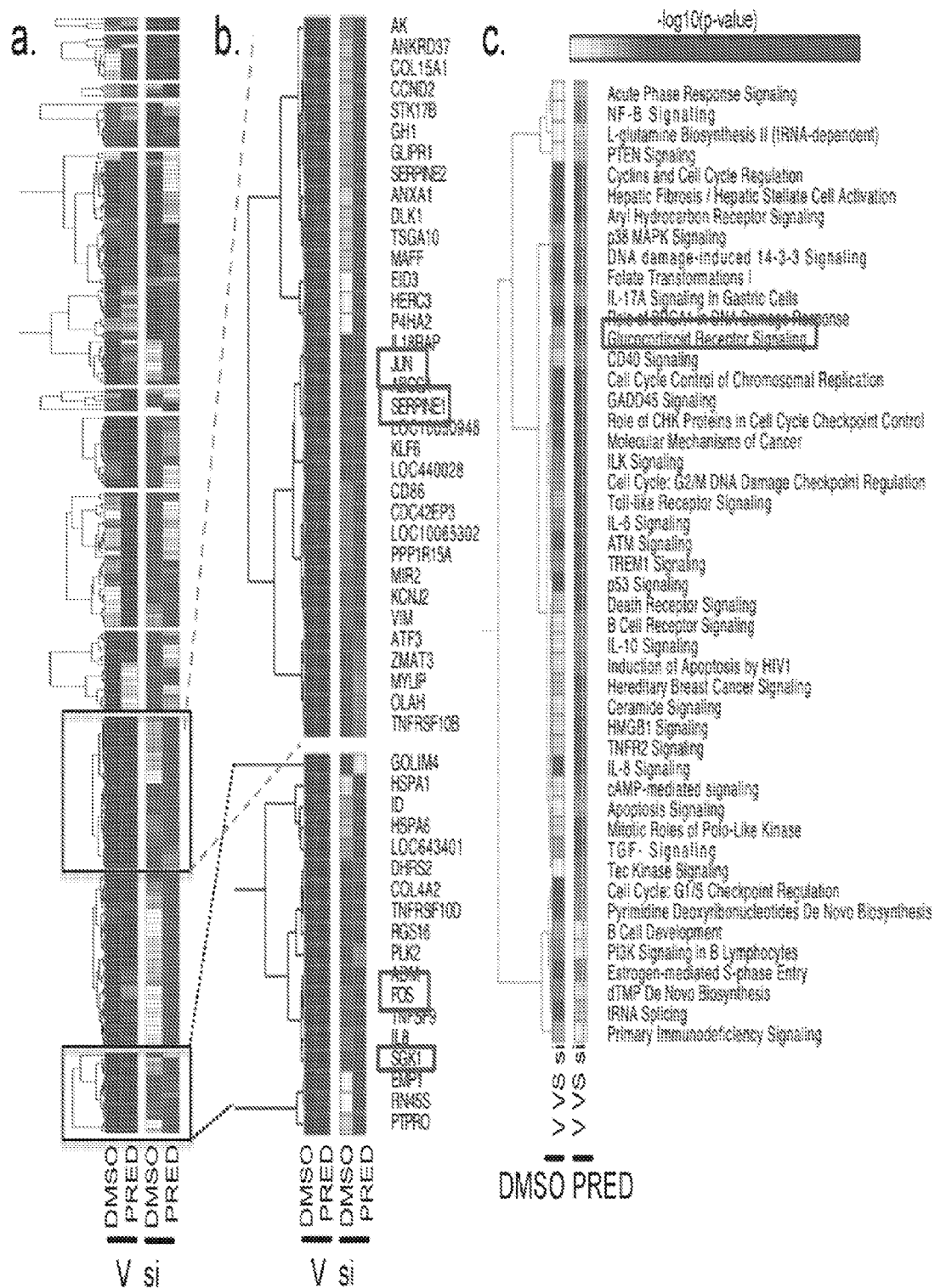
FIGS. 13A-13K—BALIR-2 plays a role in the glucocorticoid response pathway. (A) Hierarchical gene clustering of microarray data from RS4;11 cells treated with or without siRNA2 against BALIR-2 and with or without prednisolone. Abbreviations, V, Vector; si, siRNA 2 against BALIR-2; DMSO, Dimethylsulfoxide (used to solubilize prednisolone); PRED, prednisolone. (B) Two clusters of genes significantly over-expressed in siRNA2 treated cells include genes involved in glucocorticoid response (FOS, JUN, SGK1 and SERPINE1) (C) Functional analysis of genes differentially expressed in siRNA2 treated cells shows significant enrichment of various canonical pathways, including Glucocorticoid Receptor Signaling. (D-F). RT-qPCR confirmation of microarray results, confirming knockdown of BALIR-2 (D), and upregulation of FOS (E) and JUN (F). (G). RT-qPCR analysis of the pro-apoptotic regulator BIM, which is downstream of JUN in the glucocorticoid receptor pathway. (H-K). Prednisolone treatment of RS4;11 cells results in downregulation of BALIR-2 (H), with upregulation of FOS (I), JUN (J) and downstream activation of BIM (K). Overall, the effects of the siRNA are similar to those induced by prednisolone treatment. RT-qPCR confirmation was performed at least three times on independently derived cell lines, and showed overall similar results.
Figures 13D, 13E, 13F, 13G, 13H, 13I, 13J, 13K:
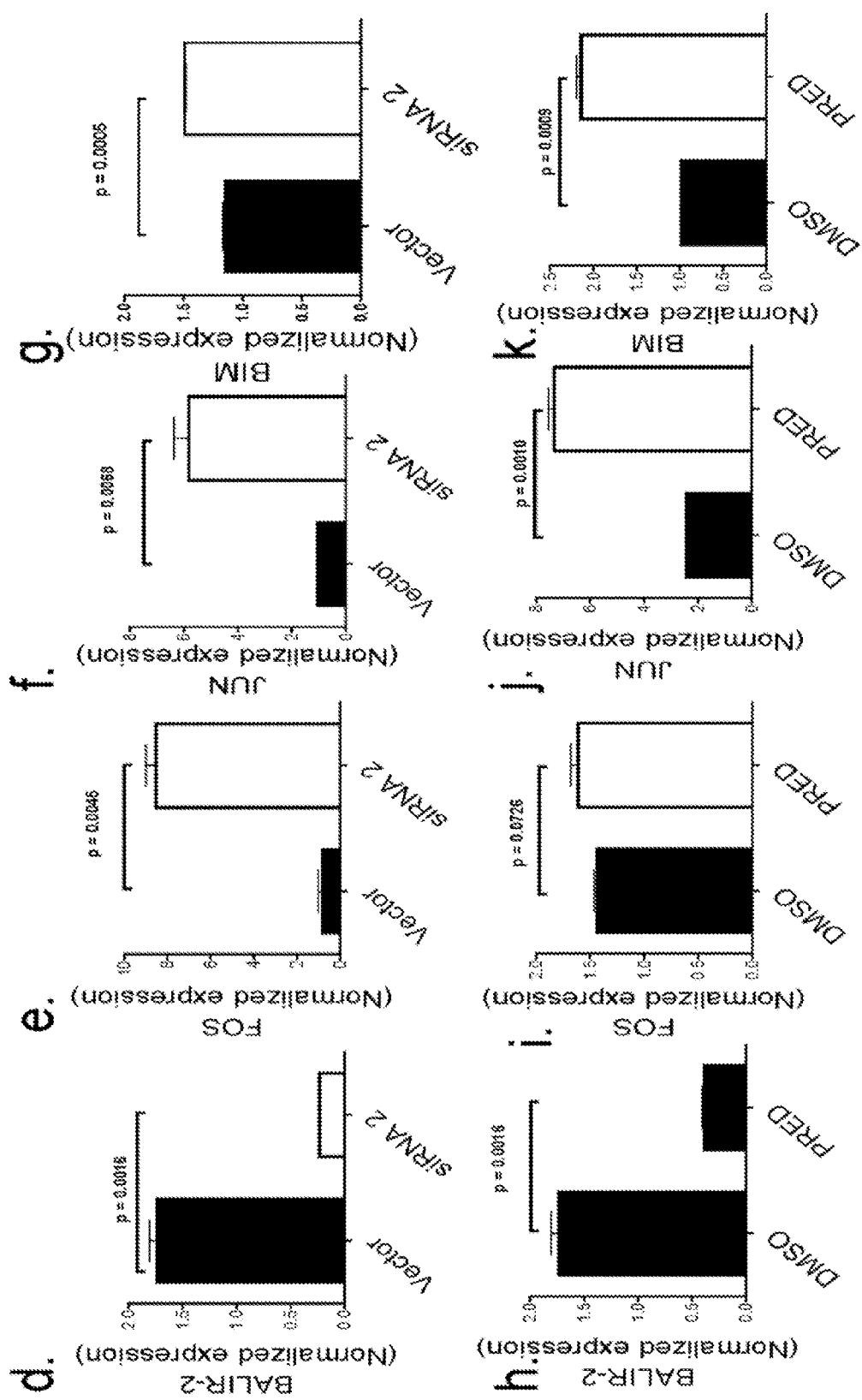
Figures 18A, 18B, 18C, 18D, 18E, 18F:
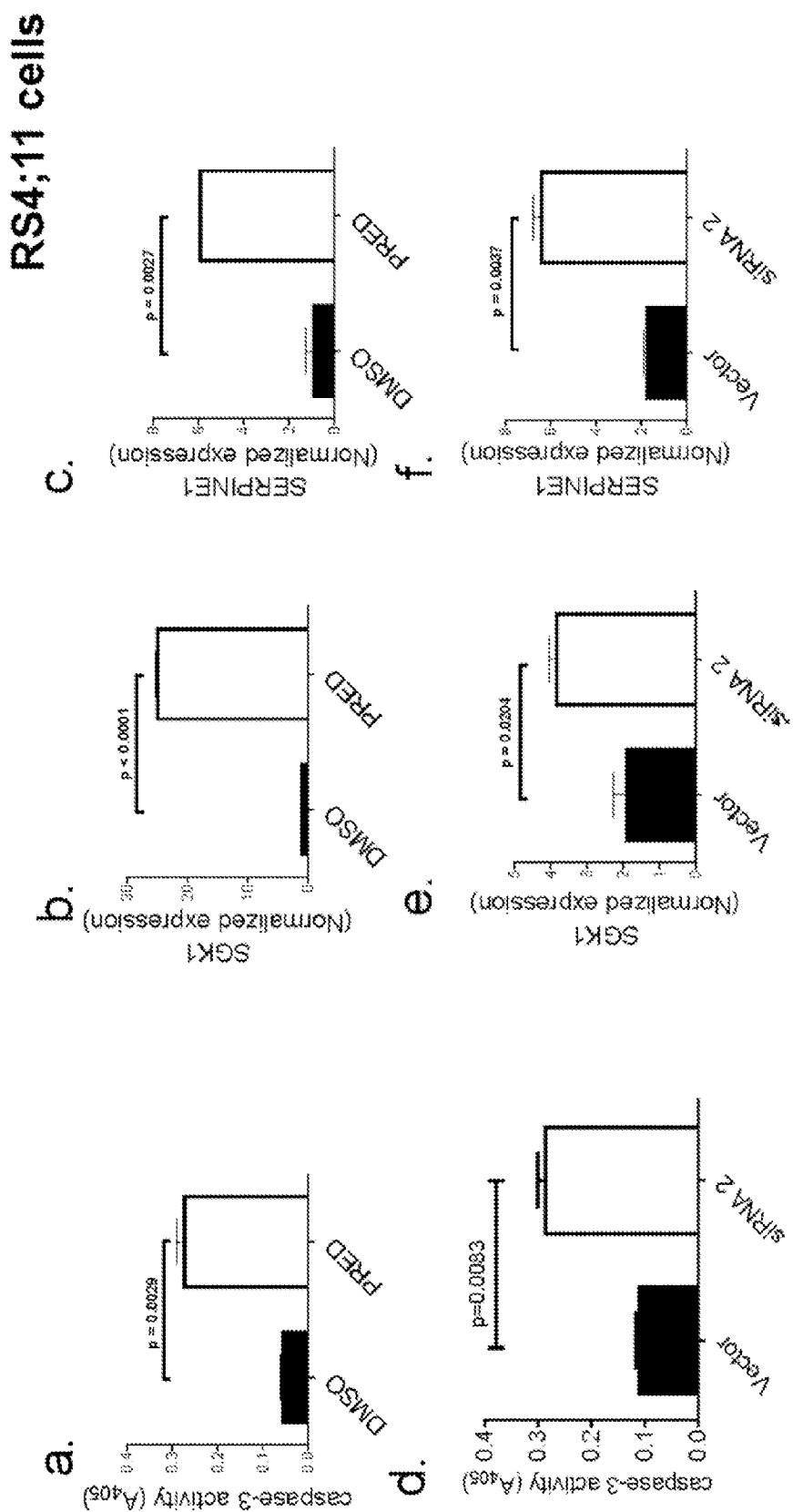
FIGS. 18A-18R—Critical glucocorticoid responsive genes show altered expression after knockdown of BALIR-2 in both human and mouse cell lines, mirroring the effects of glucocorticoid receptor engagement. (A-F) Caspase-3 activity (A) and the expression of glucocorticoid response genes SGKI (B), SERPINEI (C), in RS4; 11 cells treated with prednisolone. Similarly, knockdown of BALIR-2 by siRNA2 (E) demonstrates a similar increase in the expression of SGKI (F) and SERPINEI (G). Caspase-3 activity and the expression of mouse glucocorticoid response genes Fos (H), Jun (1), and Bim (J) are altered in 70Z/3 cells treated with prednisolone. (K) Knockdown of BALIR-2 by siRNA-like sequence against the splice junction (44) in Reh cell line, shown by RT-qPCR (normalized to Actin). (L) Increased apoptosis in Reh cells stably transduced with siRNA against the splice junction of BALIR-2, measured by caspase-3 activity. (M) Reduction of cell proliferation in Reh cells stably transduced with siRNA against BALIR-2, measured by MTS assay. (N-R) Expression of glucocorticoid response genes, SERPINEI (N), SGKI (0), FOS (P), JUN (Q), and JUNS's target BIM®, and upon siRNA mediated knockdown of the lincRNA.
Figures 18G, 18H, 18I, 18J:
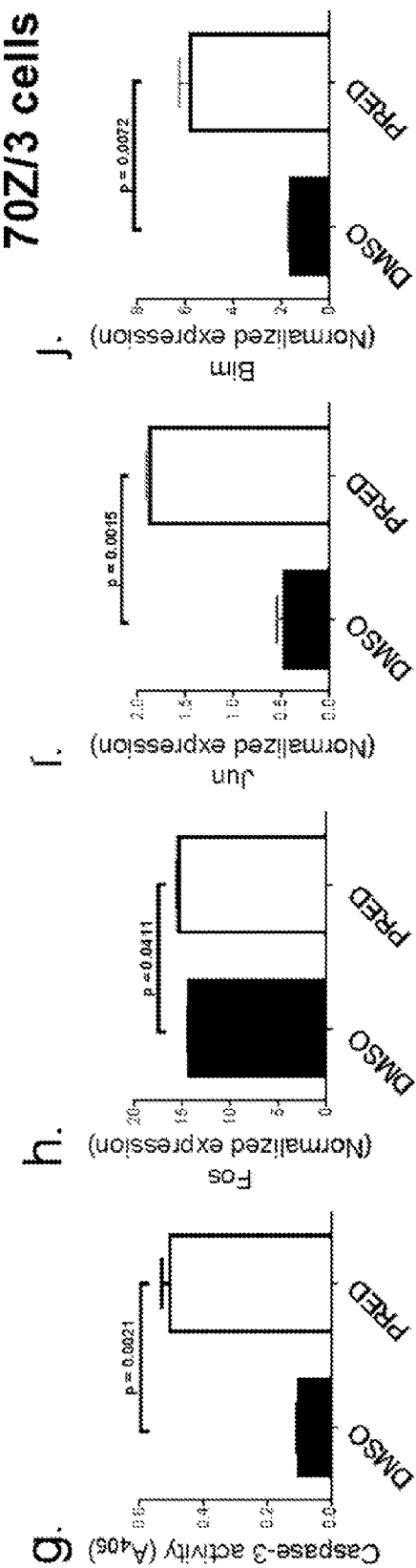
Figures 18K, 18L, 18M, 18N:
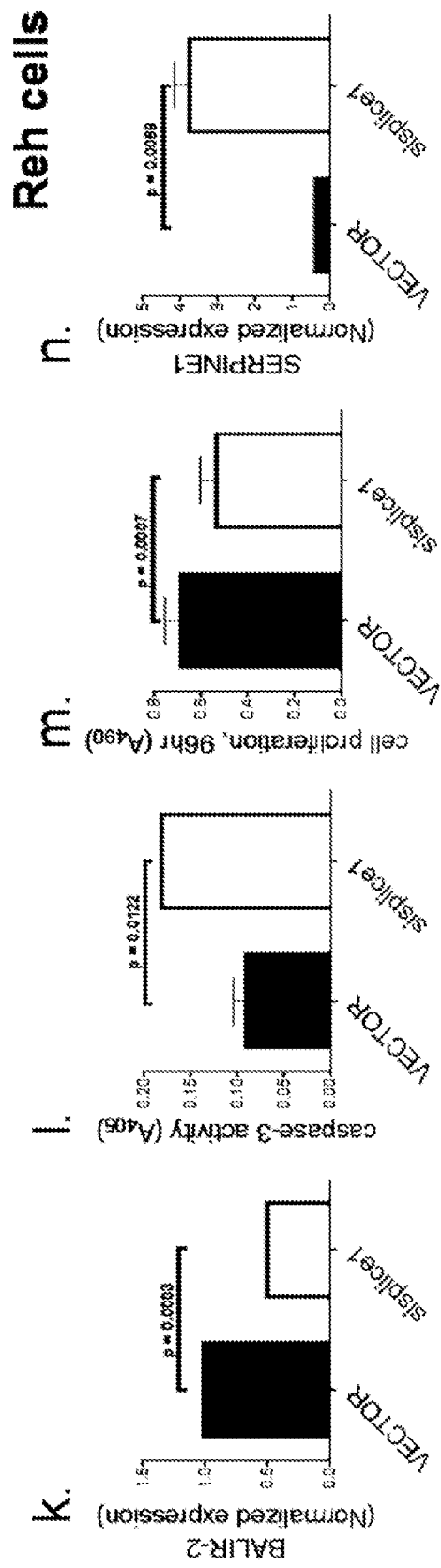
Figures 18O, 18P, 18Q, 18R:
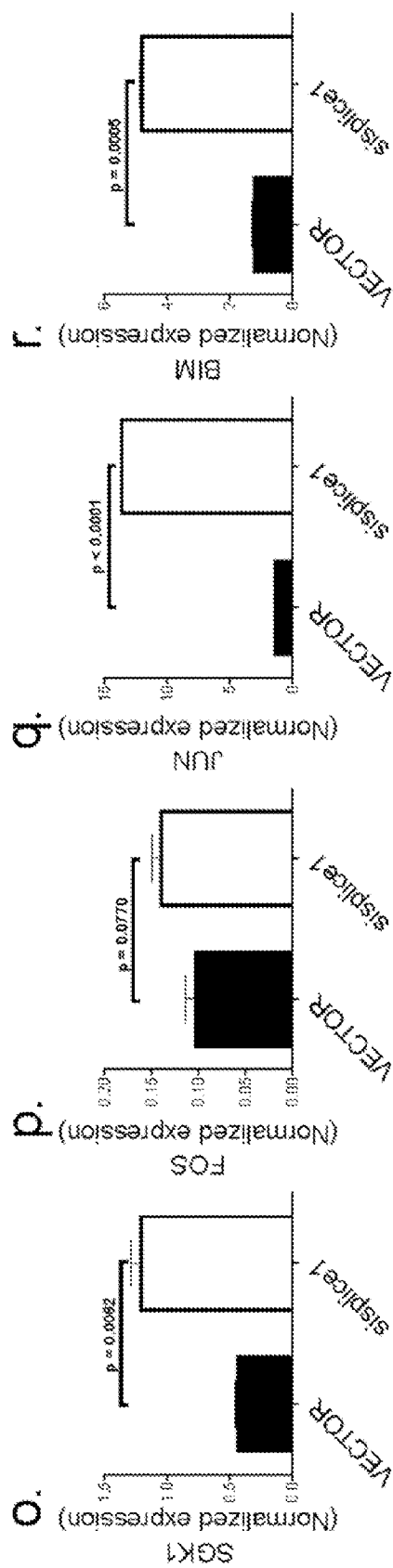

To examine the mechanism by which BALIR-2 affects proliferation and apoptosis in B-ALL cell lines, we examined gene expression in RS4;11 cell lines stably transduced with siRNA2 (which showed the greatest degree of knockdown against BALIR-2), with and without prednisolone treatment. Unsupervised hierarchical clustering analysis identified clusters (FIG. 13A-B) of genes that were upregulated in the siRNA group, both with and without prednisolone treatment. Several of these clusters consist of genes involved in the glucocorticoid receptor signaling pathway, confirmed by functional annotation results (2-4 fold increases in FOS, HSPA6, SGK1, IL8, JUN, SERPINE1, CDKN1A and ICAM1 in siRNA group, both with and without prednisone treatment; FIGS. 13B and 13C). We confirmed knockdown of BALIR-2 and upregulation of FOS, JUN, SGK1 and SERPINE1 (FIG. 13D-F and FIG. 18E-F) by RT-qPCR. Most interestingly, we determined that BALIR-2 itself was repressed by prednisolone treatment (FIG. 13H). As expected, prednisolone treatment resulted in induction of apoptosis and increased expression of FOS and JUN (FIG. 18A and FIG. 13I-J). We also observed upregulation of the pro-apoptotic protein BIM in both knockdown and prednisolone-treated cells, which is a downstream target of JUN and an important mediator of glucocorticoid-induced apoptosis of lymphocytic cells (Heidari, et al, 2012) (FIGS. 13G and 13K). Overall, these findings demonstrated parallel effects of prednisolone treatment and BALIR-2 knockdown, suggesting that they regulate related pathways.

The Function of BALIR-2 is Conserved in Human and Mouse Cells.

Figures 14A, 14B, 14C, 14D, 14E, 14F:
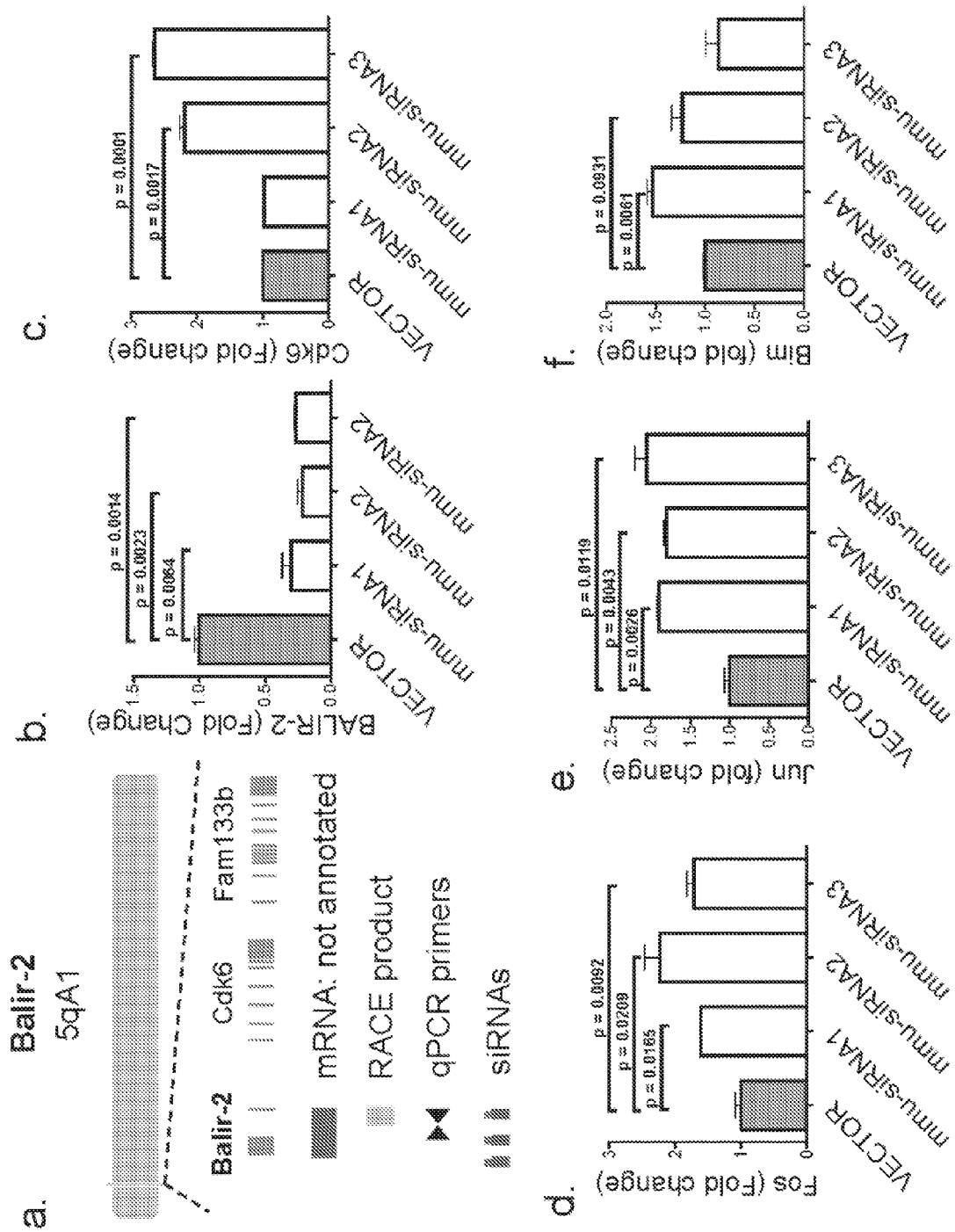
FIGS. 14A-14H—The mouse homolog of BALIR-2, Balir-2, shows a functional role in mice B-ALL cell lines. (A) Map showing the position of Balir-2 in the genome, including the locations of neighboring genes (exons shown in green), un-annotated mRNA, RACE product confirmation, qPCR primers and siRNAs targeting the mouse lincRNA. (B) siRNA-mediated knockdown of Balir-2 in 70Z/3 mouse cell line, shown by RT-qPCR (normalized to L32). (C) Expression of Balir-2 surrounding gene Cdk6 upon siRNA mediated knockdown of the mouse lincRNA. (D-F) Expression of glucocorticoid response genes Fos (D), Jun (E) and its target Bim (F), upon siRNA mediated knockdown of the mouse lincRNA. Expression was analyzed by RT-qPCR and Western blot. (H) Balir-2 expression is decreased in 70Z/3 cells upon prednisolone treatment for 6 hrs.
Figures 14G, 14H:
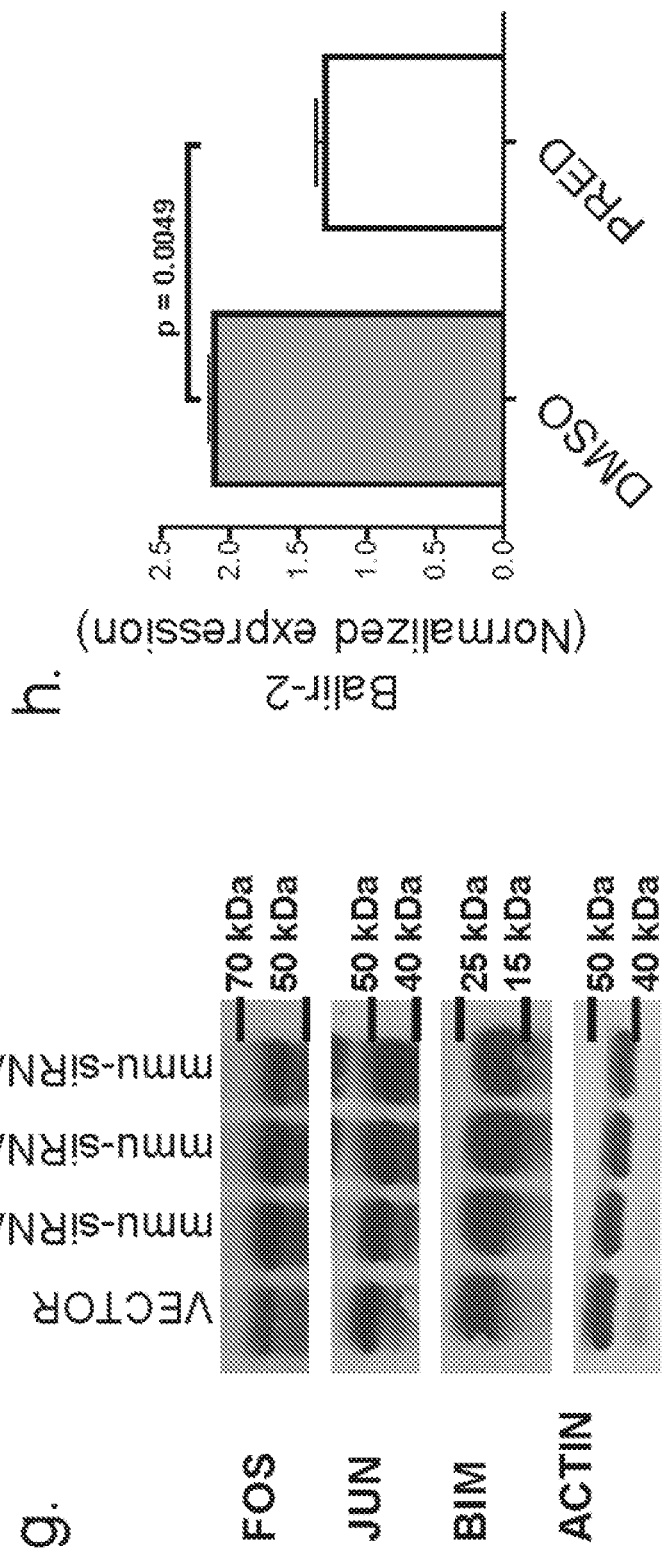
Figures 15A, 15B, 15C, 15D, 15E, 15F, 15G, 15H:
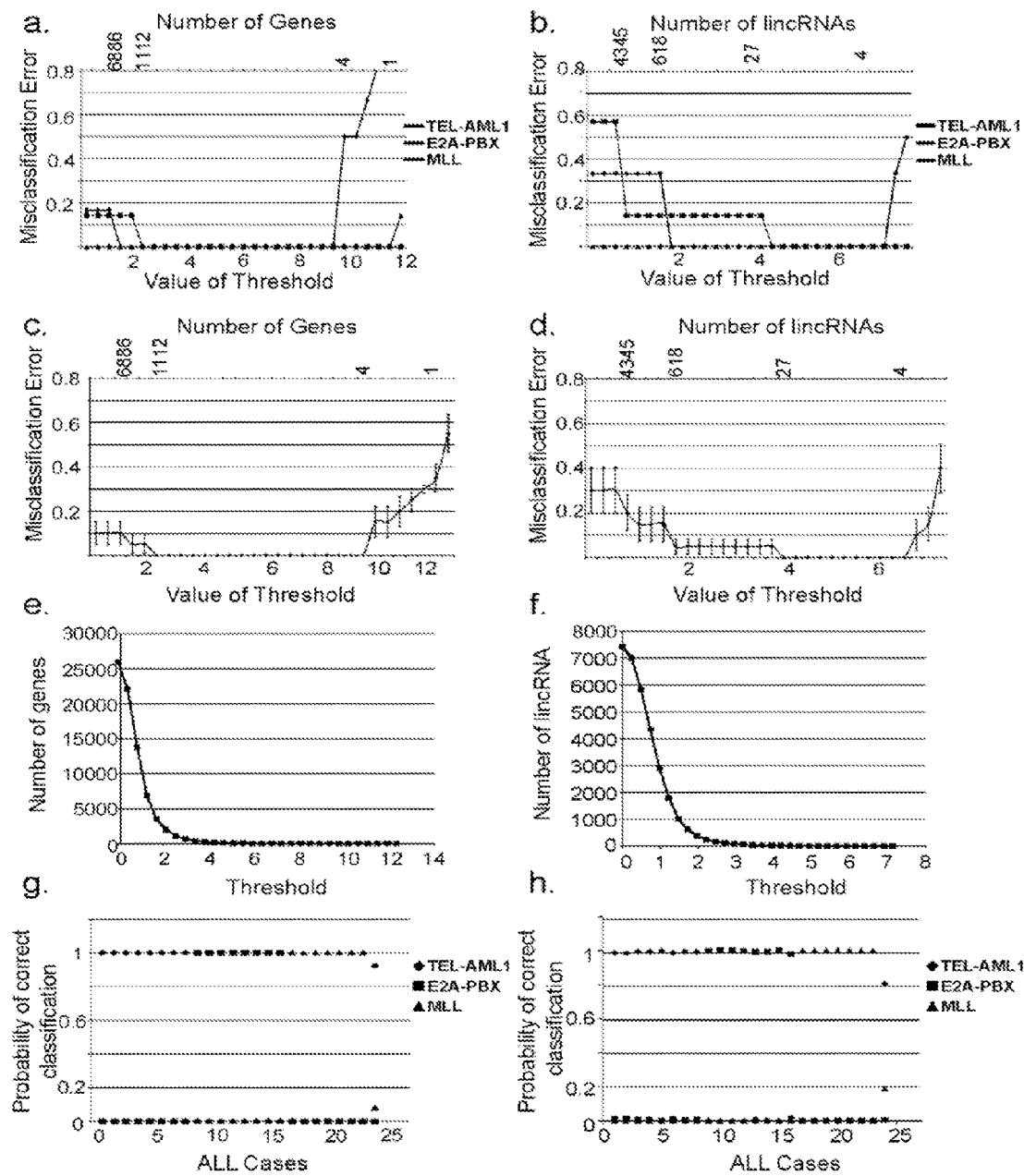
FIGS. 15A-15H—LincRNA expression can predict the cytogenetic subtype of B-ALL. Class prediction of the subtypes of B-ALL using the nearest shrunken centroid method. (A-D) Using the initial 20 cases as training data, subsets of protein coding genes (A, C) or lincRNAs (B, D) can distinguish B-ALL subtypes. The misclassification error and the number of genes for each threshold were computed using the R library of prediction analysis for microarrays (PAM). Individual (A-B) and cumulative (C-D) cross-validation error of PAM model are shown as a function of the threshold. Error bars show the standard error. (E-F) Scatter plot showing the number of genes as a function of the threshold. Number of protein-coding genes ranges from 1112 to 4 for the thresholds of 2.125 to 9.351 (E) while number of lincRNAs was only 27 for the thresholds of 3.939 to 6.401 (F). (G-H) Prediction results of the 24 independent samples of B-ALL. One of the 8 MLL samples was misclassified as TEL-AMLI when the threshold was set at 4.676 for protein coding genes or 3.969 for lincRNAs. This analysis showed that the misclassification errors reached a minimum between the thresholds 2.125 to 9.351 (corresponding to gene numbers of 1112 to 4) for protein-coding genes and 3.939 to 6.401 (gene numbers of 27 to 4) for lincRNAs, respectively. We then proceeded to examine the classification of 24 independent samples of B-ALL using the thresholds that produced the minimum error rate. When the threshold was set at 4.676 (number of protein coding genes=113), one case of ALL became misclassified; whereas one could use 27 lincRNAs at the threshold 3.969 before the same case was misclassified.
Figures 16A, 16B, 16C, 16D, 16E:
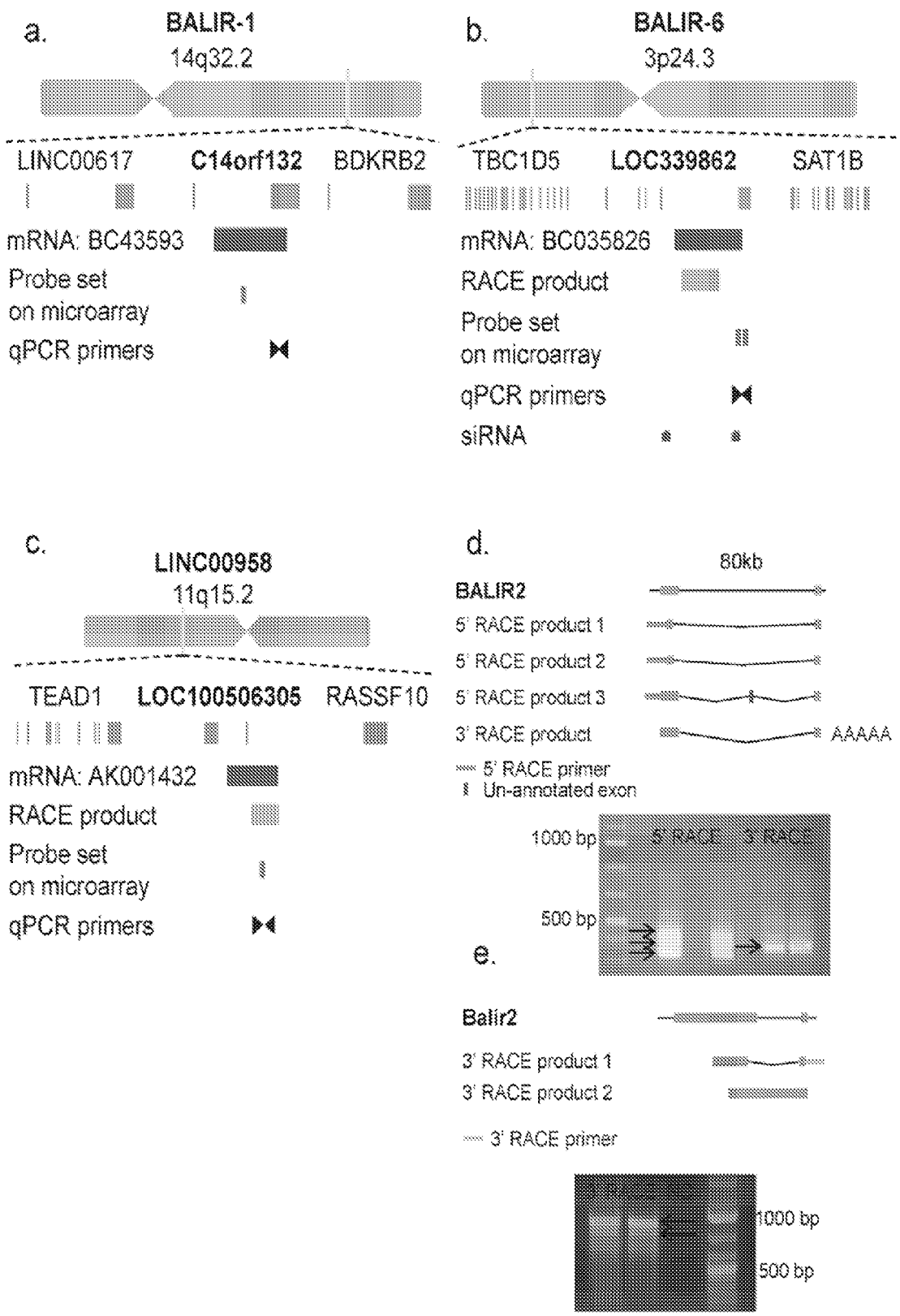
FIGS. 16A-16E—LincRNA positional information and molecular characterization of BALIR-2. (A-C) Maps showing the positions of BALIR-1 (A), BALIR-6 (B) and LINC00958 (C) in the human genome, including the locations of neighboring genes (exons shown in green), corresponding annotated mRNA, RACE product confirmation (BALIR-6 and LINC00958 only), probe set on microarray, Qper primers and siRNAs targeting the lincRNA (BALIR-1 and BALIR-6 only). (D-E) Diagrams showing the BALIR-2 loci with annotated exons (in green) and the RACE sequence products obtained from the human (D) and mouse homolog of BALIR-2 (E). 5' and 3' RACE primers are shown in blue and yellow. Newly discovered exon shown in red. RACE gel confirmation is shown on the bottom of the each diagram.
Figures 17A, 17B, 17C, 17D, 17E, 17F, 17G:
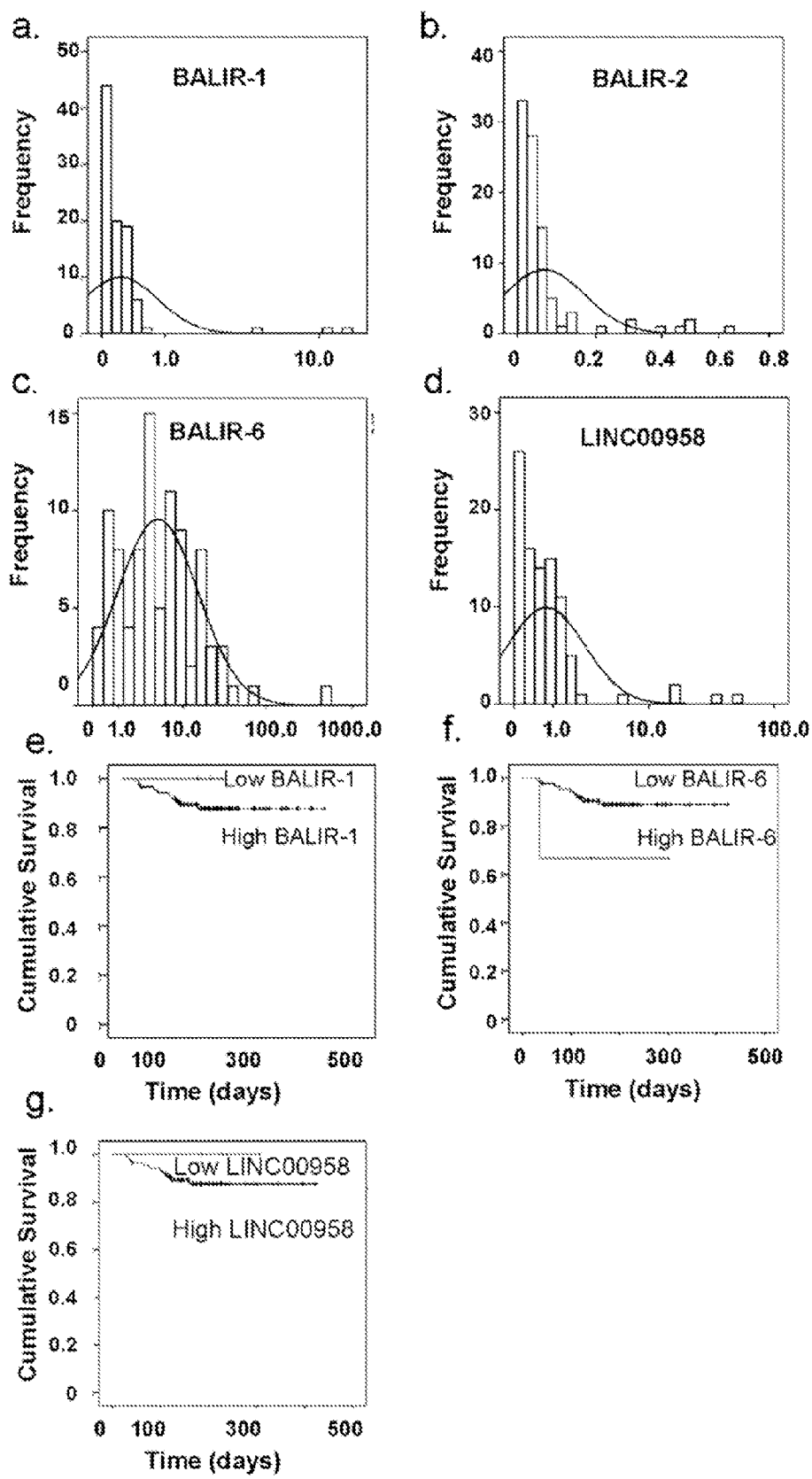
FIGS. 17A-17G—Two step cluster analysis identified two clusters of expressors. (A-D) Histogram showing the distribution of BALIR-1 (A) BALIR-2 (B), BALIR-6 (C) and LINC00958 (D) expression. Two step clustering analysis identified two clusters (high and low expression) of data within the distribution. Bars indicate the frequency of cases within each bin (n=90) (E-G) Kaplan Meier survival analysis for the high and low expression groups of BALIR-1 (E, overall survival (OS) high=I 00%, OS low=88.5%), BALIR-6 (F, OS high=66.7%, OS low=89.7%) and LINC00958 (G, OS high=100%, OS low=88.4%).
Figure 19:
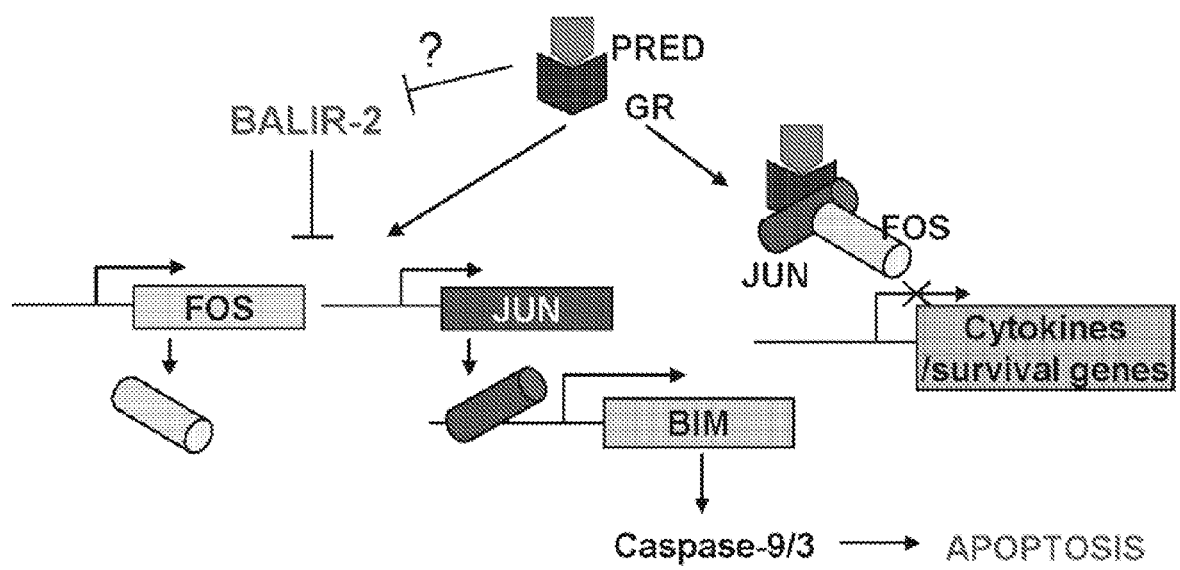
FIG. 19—Proposed mechanism of action of BALIR-2 in the glucocorticoid response pathway. BALIR-2 inhibits expression of FOS and JUN genes. Upon prednisone treatment BALIR-2 is inhibited, releasing the block on FOS and JUN. JUN is expressed and in turn activates expression of BIM which is a well-known proapoptotic gene.

To assess functional conservation of BALIR-2, we mapped and characterized murine Balir-2 to 5qA1, and the murine transcript demonstrates 90% homology to the human sequence (FIG. 14A). RACE was performed and two products were identified at this locus (FIG. 16E). We generated miRNA-formatted siRNAs (Rao, et al., 2010) against the mapped murine transcript and confirmed decreased expression in the murine pre-B cell line 70Z/3 (FIG. 14B). As in the human, we observed increased expression of Cdk6, which is immediately adjacent to Balir-2 in the mouse genome (FIG. 14C). Similar to what we observed in human cell lines, Balir-2 knockdown led to an upregulation of Jun and Fos in all three of the cell lines with upregulation of Bim in two out of three cell lines (FIG. 14D-F). We further confirmed the upregulation of these proteins by western blot analysis (FIG. 14G). As in human cells, prednisolone treatment led to downregulation of Balir-2 concomitant with increased apoptosis, and upregulation of Jun, Fos and Bim (FIG. 14H and FIG. 18G-J) in 70Z/3 cells, mirroring our observations from the RS4;11 line. We also examined the effects of BALIR-2 expression in a second human B-ALL cell line, Reh (FIG. 18K-R), utilizing a novel method to target the transcript. Based on the method of Ulitsky et al, we generated a siRNA-like sequence within our miRNA formatted vector, targeting the splice junction of the BALIR-2 transcript (Ulitsky, et al., 2011). Knockdown of BALIR-2 resulted in increased apoptosis, decreased cell proliferation and significant upregulation of SGK1, SERPINE1, FOS, JUN, and BIM (FIG. 18K-R), as seen previously in RS4;11 and murine 70Z/3 cells. Our data indicate that BALIR-2 plays a key role in regulating the glucocorticoid receptor signaling pathway, thereby regulating the cellular response to prednisolone treatment (A putative schematic mechanism is presented in FIG. 19).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Affymetrix/Cold Spring Harbor Laboratory, *Nature*. 457: 1028-1032, 2009.
Alnemri, E. S., et al., *Cancer Res*. 52:491-495, 2002.
Baltimore, D., et al., *Nat Immunol*. 9:839-845, 2008.
Bene, M. C., et al., *Leukemia*. 9:1783-1786, 1995.
Borowitz, M. J., and Chan, J. K. C. *WHO Classification of Tumours of Haematopoietic and Lymphoid Tissues*. 168-175, 2008.
Carninci, P., et al., *Science*. 309:1559-1563, 2005.
Carrieri, C., et al., "Long non-coding antisense RNA controls Uchl1 translation through an embedded SINEB2 repeat." *Nature*. advance online publication, 2012.
Casale, F., et al., *Int J Oncol*. 22:123-128, 2003.
Cesana, M., et al., *Cell*. 147:358-369, 2011.
Cheng, J., et al., *Science*. 308:1149-1154, 2005.
Conter, V., et al., *Blood*. 115:3206-3214, 2010.
Costinean, S., et al., *Proc Natl Acad Sci. USA* 103:7024-7029, 2006.
Dinger, M. E., et al., *Genome Research*. 18:1433-1445, 2008.
Golub, T. R., et al., *Science*. 286:531-537, 1999.
Gong, C., et al., *Nature*. 470:284-288, 2011.
Guttman, M., et al., *Nature*. 458:223-227, 2009.
Guttman, M., et al., *Nature*. 477:295-300, 2011.
Heidari, et al, *Cell Death Dis*. 3:e349, 2012.
Hu, W., et al., *Genes & Development*. 25:2573-2578, 2011.
Huarte, M., et al., *Cell*. 142:409-419, 2010.
Kapranov, P., et al., *Science*. 296:916-919, 2002.
Kapranov, P., et al., *Science*. 316:1484-1488, 2007.
Karreth, F. A., et al., *Cell*. 147:382-395, 2011.
Khalil, A. M., et al., *Proc Natl Acad Sci USA*. 106:11667-11672, 2009.
Klein, U., et al., *Cancer Cell*. 17:28-40, 2010.
Lu, J., et al., *Nature*. 435:834-838, 2005.
Ng, S.-Y., et al., *EMBO J*. 31:522-533, 2012.
Niazi, F., and Valadkhan, S. *RNA*. 18:825-843, 2012.
Nordlund, J., et al., *Leukemia*. 26:1218-1227, 2012.
O'Connell, R. M., et al., *J Exp Med*. 205:585-594, 2008.
O'Connell, R. M., et al., *PLoS ONE*. 5:e12009, 2010.
O'Connell, R. M., et al., *Proc Natl Acad Sci USA*. 106:7113-7118, 2009.
Paralkar, V. R., and Weiss, M. J. *Genes & Development*. 25:2555-2558, 2011.
Prensner, J. R., et al., *Nat Biotech*. 29:742-749, 2011.
R Development Core Team. R Foundation for Statistical Computing, 2008.
Rao, D. S., et al., *Immunity*. 33:48-59, 2010.
Rinn, J. L., et al., *Cell*. 129:1311-1323, 2007.
Salmena, L., et al., *Cell*. 146:353-358, 2011.
Sheik Mohamed, J., et al., *RNA*. 16:324-337, 2011.
Smith, G. K. *Statistical Applications in Genetics and Molecular Biology*. 3, 2004.
Tibshirani, R., et al., *Proc Natl Acad Sci USA*. 99:6567-6572, 2002.
Tibshirani, R., et al., *Statistical Science*. 18:104-117, 2003.
Tissing, W. J. E., et al., *Blood*. 109:3929-3935, 2007.
Tripathi, V., et al., *Mol Cell*. 39:925-938, 2010.
Ulitsky, I., et al., *Cell*. 147:1537-1550, 2011.
Vangipuram, S. D., et al., *Tumour Biol*. 33:2173-2183, 2012.
Wang, Z., et al., *J Biol Chem*. 278:23861-23867, 2003.
Yu, W., et al., *Nature*. 451:202-206, 2008.
Zhang, B., et al., *Cell Reports*. 2:111-123, 2012.

The invention claimed is:

1. An isolated DNA molecule that comprises a sequence that is identical or complementary to a region of at least 15 contiguous nucleotides in SEQ ID NO:38 (BALIR-2), wherein the region comprises contiguous nucleotides from two exons of the BALIR-2 gene.

2. The isolated DNA molecule of claim 1 wherein the nucleic acid molecule comprises a sequence that is 100% identical or complementary to a region of at least 20 contiguous nucleotides in SEQ ID NO:38.

3. The isolated DNA molecule of claim 1, wherein the nucleic acid molecule comprises a sequence that is at least 90% identical or complementary to a region of at least 150 contiguous nucleotides in SEQ ID NO:38.

4. A method of evaluating blood or bone marrow cells from a patient with leukemia or suspected of having leukemia comprising measuring expression in blood or bone marrow cells of at least one B-lymphoblastic leukemia lincRNA (BALIR) molecule and comparing the expression to a control or reference level(s) of expression in blood or bone marrow cells, wherein measuring expression involves a DNA molecule comprising or complementary to at least 15 contiguous nucleotides from two exons of SEQ ID NO:38.

5. The method of claim 4, further comprising measuring expression of at least or at most 2, 3, or 4 additional BALIR molecules and comparing the expression to a control or reference level(s) of expression.

6. The method of claim 4, wherein the control or reference level of expression is the level of expression of the BALIR molecule in non-leukemic blood or bone marrow cells.

7. The method of claim 5, wherein the additional BALIR molecules are BALIR-1, BALIR-6, or, BALIR-11.

8. The method of claim 4, wherein the BALIR molecule is BALIR-2 and the measured expression level of BALIR-2 is determined to be increased compared to a control or reference level of BALIR-2.

9. The method of claim 4, further comprising determining the level of expression of one or more measured lincRNAs in Table 1 is increased relative to the control or reference level of the lincRNA.

10. The method of claim 4, wherein measuring expression comprises generating complementary DNA (cDNA) of the BALIR molecule or any other lincRNA.

11. The method of claim 4, wherein measuring expression comprises an assay involving amplification and/or hybridization of a nucleic acid molecule.

12. The method of claim 4, wherein measuring expression involves polymerase chain reaction (PCR).

13. The method of claim 12, wherein measuring expression involves real time quantitative polymerase chain reaction (RT-qPCR).

14. The method of claim 4 further comprising generating a cDNA of the BALIR molecules or any other lincRNAs to be measured and incubating the cDNA with primers under conditions to provide amplification of the BALIR molecules, any other lincRNA, and/or their complements.

15. The method of claim 4, further comprising isolating nucleic acid molecules from the blood or bone marrow cells, wherein the nucleic acid molecules include lincRNA.

16. The method of claim 4, wherein expression is measured in situ.

17. The method of claim 4, further comprising evaluating the blood or bone marrow cells.

18. The method of claim 4, further comprising evaluating the cytology of blood or bone marrow cells.

19. The method of claim 4, further comprising evaluating cells obtained from the patient's spinal fluid to identify leukemia cells.

20. A method for treating a patient with B-lymphoblastic leukemia comprising
   a) administering to the patient prednisone, chemotherapy, radiation, or a bone marrow or cord blood transplant, or a combination thereof after the patient is determined to have increased expression of BALIR-2 in a process involving a DNA molecule comprising or complementary to at least 15 contiguous nucleotides from two exons of SEQ ID NO:38.

* * * * *